US012747235B2

(12) United States Patent
Cecere et al.

(10) Patent No.: US 12,747,235 B2
(45) Date of Patent: Sep. 29, 2026

(54) TRIAZOLYL DERIVATIVES AS $GABA_A$ α5 PAM

(71) Applicant: Hoffmann-La Roche Inc., Little Falls, NJ (US)

(72) Inventors: Giuseppe Cecere, Basel (CH); Guillaume Décoret, Eschentzwiller (FR); Katrin Groebke Zbinden, Liestal (CH); Maria-Clemencia Hernandez, Delémont (CH); Henner Knust, Rheinfelden (DE); Andreas Koblet, Bottmingen (CH); Andres Miguel Olivares Morales, Binningen (CH); Emmanuel Pinard, Linsdorf (FR); Valerie Runtz-Schmitt, Rixheim (FR)

(73) Assignee: Hoffmann-La Roche Inc., Branchburg, NJ (US)

( * ) Notice: Subject to any disclaimer, the term of this patent is extended or adjusted under 35 U.S.C. 154(b) by 420 days.

(21) Appl. No.: 18/054,651

(22) Filed: Nov. 11, 2022

(65) Prior Publication Data

US 2023/0135093 A1 May 4, 2023

Related U.S. Application Data

(63) Continuation of application No. PCT/EP2021/062388, filed on May 11, 2021.

(30) Foreign Application Priority Data

May 13, 2020 (EP) .................................... 20174309

(51) Int. Cl.

| | |
|---|---|
| ***C07D 413/14*** | (2006.01) |
| ***C07D 401/14*** | (2006.01) |
| ***C07D 403/06*** | (2006.01) |
| ***C07D 403/14*** | (2006.01) |
| ***C07D 491/107*** | (2006.01) |

(52) U.S. Cl.

CPC ......... *C07D 413/14* (2013.01); *C07D 401/14* (2013.01); *C07D 403/06* (2013.01); *C07D 403/14* (2013.01); *C07D 491/107* (2013.01)

(58) Field of Classification Search

CPC .. C07D 413/14; C07D 401/14; C07D 403/06; C07D 403/14; C07D 491/107; C07D 491/10; A61P 25/18

See application file for complete search history.

(56) References Cited

U.S. PATENT DOCUMENTS

| | | | | |
|---|---|---|---|---|
| 8,697,696 B2 * | 4/2014 | Gabriel | A61P 25/04 | 514/342 |
| 8,742,097 B2 * | 6/2014 | Hernandez | C07D 403/14 | 544/131 |
| 2016/0115155 A1 * | 4/2016 | Larsen | C07D 403/12 | 514/252.05 |

FOREIGN PATENT DOCUMENTS

| | | |
|---|---|---|
| JP | 2015-521643 | 7/2015 |
| JP | 2013-543852 | 12/2019 |
| WO | 2012/062687 A1 | 5/2012 |
| WO | 2014/001280 A1 | 1/2014 |
| WO | 2014/001282 A1 | 1/2014 |
| WO | 2019/192633 | 12/2019 |

OTHER PUBLICATIONS

International Search Report with written opinion—PCT/EP2021/062388 mailed Jul. 5, 2021, pp. 1-11.

Preliminary Report on Patentability—PCT/EP2021/062388 Issued Nov. 15, 2022, pp. 1-13.

* cited by examiner

*Primary Examiner* — Robert H Havlin

(74) *Attorney, Agent, or Firm* — Robert C. Hall

(57) ABSTRACT

The invention provides compounds having the general formula (I) or (II)

(I)

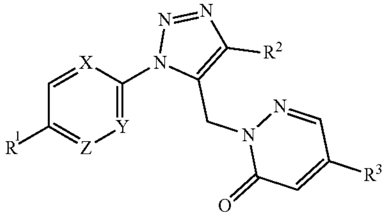

(II)

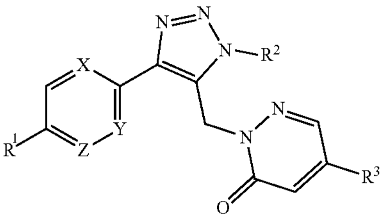

wherein $R^1$, $R^2$, $R^3$, X, Y and Z are as described herein, compositions including the compounds and methods of using the compounds.

3 Claims, No Drawings

TRIAZOLYL DERIVATIVES AS $GABA_A$ α5 PAM

CROSS-REFERENCE TO RELATED APPLICATIONS

This application is a continuation of International Application No. PCT/EP2021/062388 filed on May 11, 2021, which claims priority to European Patent Application No. 20174309.3 filed on May 13, 2020, the disclosures of which is incorporated herein by reference.

BACKGROUND OF THE INVENTION

Receptors for the major inhibitory neurotransmitter, gamma-aminobutyric acid (GABA) are divided into two main classes: (1) $GABA_A$ receptors, which are members of the ligand-gated ion channel superfamily and (2) $GABA_B$ receptors, which are members of the G-protein linked receptor family. The $GABA_A$ receptor complex which is a membrane-bound heteropentameric protein polymer is composed principally of α, β and γ subunits. $GABA_A$ receptors are ligand-gated chloride channels and the principal mediators of inhibitory neurotransmission in the human brain.

There are 19 genes encoding for $GABA_A$ receptor subunits that assemble as pentamers with the most common stoichiometry being two α, two β and one γ subunit. $GABA_A$ subunit combinations give rise to functional, circuit, and behavioral specificity (Sieghart, 2006; Vithlani et al., 2011). $GABA_A$ receptors containing the α5 subunit ($GABA_A$ a5) are of particular interest due to their restricted pattern of expression and unique physiological and pharmacological properties (Sur et al., 1999; Mohler, 2011). The $GABA_A$ a5 subunit-containing receptors are preferentially localized in the hippocampus, prefrontal cortex, nucleus accumbens and amygdala, which are key regions believed to be involved in the neuropathology and pathophysiology of a variety of CNS disorders.

Hippocampal hyperactivity as result of reduced $GABA_A$ α5 expression or GABAergic deficit or other conditions, is the common hallmark of a variety of CNS disorders characterized by cognitive decline (memory and executive functions). In such a disease state, a $GABA_A$ α5 positive allosteric modulator (PAM) and not a negative allosteric modulator (NAM) may be an effective treatment for the cognitive impairment associated with such diseases.

Multiple lines of evidence suggest that an imbalance between excitatory/inhibitory neurotransmission arising from dysfunction of GABAergic signaling system, the main inhibitory neurotransmitter system in the brain, to be at the core of the pathogenesis a variety of CNS disorders, including ASD (Autism Spectrum Disorder). Given the distribution of $GABA_A$ α5 receptors, they are very attractive targets for restoring levels of intracortical inhibition and consequently the (E/I) circuit balance in these conditions.

No approved pharmacological treatment exists for the core social communication and repetitive deficits of ASD, and this disorder continues to be an area of high unmet medical need. Current approved treatments for associated symptoms of ASD are limited to the antipsychotics (Risperidone and CNE/06.04.2021 Aripiprazole) indicated for the treatment of irritability associated with ASD symptoms. Emerging evidence suggests that the GABAergic system, the main inhibitory neurotransmitter system in the brain, plays a key role in the pathophysiology of ASD (Dhossche et al., 2002; Pizzarelli and Cherubini, 2011; Robertson et al., 2016).

Both genetic and imaging studies using positron emission tomography study (PET) and magnetic resonance spectroscopy (MRS) suggest alterations in GABAergic signaling in ASD. $GABA_A$ receptor binding has been reported to be dramatically reduced in the superior and medial frontal cortex of patients with ASD using [$^{123}$I]-iomazenil PET (Mori et al., 2012). Also, a pilot [$^{11}$C]-RO154513 PET study found reduced binding of this tracer suggesting lower levels of $GABA_A$ α5 receptor in ASD (Mendez et al., 2012). MRS studies found altered GABA levels in ASD (Gaetz et al., 2014; Rojas et al., 2014) and in particular some recent studies showed reduced GABA and altered somatosensory function in children with ASD and (Puts et al., 2016; Robertson et al., 2016). In line with these observations, postmortem reduced expression of $GABA_A$ receptor subunits including GABRB3 (DeLorey, 2005; Abrahams and Geschwind, 2008) and the GABA synthesizing enzymes, glutamic acid decarboxylase (GAD) 65 and 67 were found in parietal and cerebellar cortices of patients with autism (Fatemi et al., 2002). Importantly, a reduction of GABAergic inhibitory activity has been proposed to result in hyperexcitability observed in ASD, including the high incidence of seizures and auditory-tactile hypersensitivity (Rubenstein and Merzenich, 2003; Frye et al., 2016). The altered GABAergic function may reduce the threshold for developing seizures as demonstrated by the high comorbidity of epilepsy in ASD, occurring in up to one-third of affected people. Finally, enhancement of $GABA_A$ receptor activity by non-selective BZDs have been shown to ameliorate behavioral deficits in mouse models of ASD, however very narrow therapeutic margins were observed due to sedation mediated by the $GABA_A$ α1 subtype (Han et al., 2012, 2014; Soto et al. 2013). These findings support the notion that rebalancing of GABAergic transmission via $GABA_A$α5 receptors can improve symptoms in ASD without the side effects of non-selective benzodiazepines.

SUMMARY OF THE INVENTION

The invention relates to organic compounds useful for therapy or prophylaxis in a mammal, and in particular to $GABA_A$ α5 receptor positive allosteric modulators (PAMs) for the treatment or prophylaxis of $GABA_A$ α5 receptor related diseases and diseases or conditions which can be treated by the modulation of $GABA_A$ α5 receptor activity, such Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder.

The invention provides a novel compound of formula (I) and (II), or pharmaceutically acceptable salts thereof, (I)

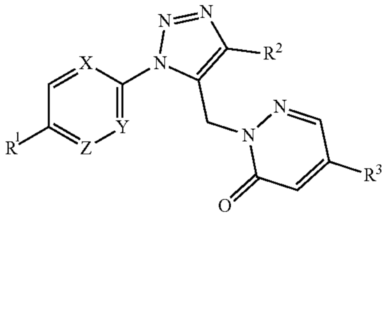

-continued (II)

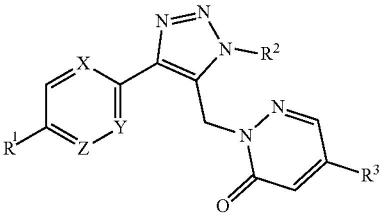

wherein

X is selected from i) N, and ii) $CR^{18}$;

Y is selected from i) N, and ii) CH;

Z is selected from i) N, and ii) CH;

$R^1$ is selected from i) $C_{1-6}$-alkyl, ii) H, iii) halo-$C_{1-6}$-alkyl, iv) $C_{1-6}$-alkoxy, v) halo-$C_{1-6}$-alkoxy, vi) hydroxy-$C_{1-6}$-alkyl, vii) $C_{3-8}$-cycloalkyl, and viii) halogen;

$R^2$ is selected from i) H, ii) $C_{1-6}$-alkyl, and iii) halogen;

$R^3$ is selected from i) $C_{3-8}$-heteroaryl optionally substituted with $R^6$, $R^7$ and R, ii) amino substituted on the nitrogen atom by one or two substituents independently selected from $R^4$ and $R^5$ iii) $C_{3-8}$-heterocycloalkyl optionally substituted with $R^9$, $R^{10}$ and $R^{11}$, iv) $C_{3-8}$-aryl substituted with $R^6$, R and R, v) halo-$C_{1-6}$-alkoxy, vi) hydroxy-$C_{1-6}$-alkyl, and vii) halo-$C_{1-6}$-alkyl;

$R^4$ is selected from i) H, and ii) $C_{1-6}$-alkyl;

$R^5$ is selected form i) H, and ii) $C_{1-6}$-alkyl;

$R^6$, $R^7$ and $R^8$ are independently selected from i) $C_{1-6}$-alkyl, ii) hydroxy-$C_{1-6}$-alkyl, iii) $C_{1-6}$-alkoxy, iv) halogen, v) halo-$C_{1-6}$-alkyl, vi) $C_{3-8}$-cycloalkyl, and vii) cyano;

$R^9$, $R^{10}$ and $R^{11}$ are independently selected from i) $C_{1-6}$-alkyl, ii) $C_{1-6}$-alkoxy, iii) $C_{1-6}$-alkoxycarbonyl, iv) $C_{3-8}$-cycloalkoxy, v) $C_{3-8}$-cycloalkyl, vi) $C_{3-8}$-cycloalkyl-$C_{1-6}$-alkoxy, vii) halo-$C_{1-6}$-alkyl, viii) $C_{1-6}$-alkoxy $C_{1-6}$-alkyl, ix) $C_{3-8}$-cycloalkylcarbonyl, x) halo-$C_{1-6}$-alkoxy, xi) cyano, xii) halogen, xiii) heteroaryl optionally substituted with $R^{12}$, $R^{13}$ and $R^{14}$, xiv) heteroaryloxy optionally substituted with $R^{12}$, $R^{13}$ and $R^{14}$, xv) hydroxy, xvi) hydroxy-$C_{1-6}$-alkyl, and xvii) oxo;

$R^{12}$, $R^{13}$ and $R^{14}$ are independently selected from i) halo-$C_{1-6}$-alkyl, ii) $C_{1-6}$-alkyl, iii) $C_{1-6}$-alkoxy, and iv) halogen;

$R^{18}$ is selected from i) H, and ii) halogen.

The compounds described herein and their pharmaceutically acceptable salts and esters can be used, alone or in combination with other drugs, as disease-modifying or as symptomatic agents for the treatment or prevention of acute neurological disorders, chronic neurological disorders, cognitive disorders, Alzheimer's disease, memory deficits, schizophrenia, positive, negative and/or cognitive symptoms associated with schizophrenia, bipolar disorders, autism, Angelman syndrome, Prader-Willi syndrome, Rett syndrome, Down syndrome, neurofibromatosis type I, sleep disorders, disorders of circadian rhythms, amyotrophic lateral sclerosis (ALS), fragile-X disorder, dementia caused by AIDS, age-associated memory impairment, psychotic disorders, substance-induced psychotic disorder, anxiety disorders, generalized anxiety disorder, panic disorder, delusional disorder, obsessive/compulsive disorders, acute stress disorder, post-traumatic stress disorder (PTSD), drug addictions, movement disorders, Parkinson's disease, restless leg syndrome, mild cognitive impairment (MCI), cognition deficiency disorders, age-related cognitive decline, multi-infarct dementia, mood disorders, depression, neuropsychiatric conditions, psychosis, attention-deficit/hyperactivity disorder, neuropathic pain, epilepsy, stroke and attentional disorders.

In certain embodiments the indication is autism spectrum disorder (ASD). ASD is a complex, heterogeneous neurodevelopmental disorder characterized by impairments in three core symptoms: social interactions, repetitive behaviors and cognitive deficits. The estimated prevalence of ASD in the United States is 1 in 68 children (CDC, 2014), and it is estimated that 1% of the world's population have ASD (WHO, 2013).

Objects of the present invention are compounds of formula (I) or (II) and their pharmaceutically acceptable salts and esters, the preparation of the above mentioned compounds, medicaments containing them and their manufacture as well as the use of the above mentioned compounds in the treatment or prevention of diseases related to $GABA_A$ α5 receptor related diseases and diseases or conditions which can be treated by the modulation of $GABA_A$ α5 receptor activity, such as Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder. Compounds of the present invention are selective $GABA_A$ α5 receptor positive allosteric modulators (PAMs) as they enhance the function of α5-containing $GABA_A$ receptors by increasing GABAergic currents (influx of chloride) at a given $EC_{20}$ concentration of gamma amino butyric acid (GABA). The compounds of the present invention have higher PAM effect than the compounds of the state of the art. In a preferred embodiment the compounds of the invention are binding selective for the α5 subunit relative to the α1, α2 and α3 subunits. Compatible with the α5-subtype brain distribution, selective $GABA_A$ α5 PAMs will restore GABAergic signaling in key brain regions (e.g. hippocampus, amygdala, nucleus accumbens and preftrontal cortex) without the side-effects of non-selective $GABA_A$ modulators (e.g. benzodiazepines). In another preferred embodiment, the compounds of the present inventions have an increased chemical stability, particularly to low and high pH conditions.

DETAILED DESCRIPTION OF THE INVENTION

The term "$C_{1-6}$-alkyl" denotes a monovalent linear or branched saturated hydrocarbon group of 1 to 6 carbon atoms. Examples of $C_{1-6}$-alkyl include methyl, ethyl, n-propyl, isopropyl, n-butyl, iso-butyl, sec-butyl, tert-butyl and pentyl. Particular $C_{1-6}$-alkyl groups are methyl, ethyl, isopropyl, iso-butyl and tert-butyl. More particular examples are methyl and ethyl.

The term "$C_{1-6}$-alkoxy" denotes a group of the formula —O—R', wherein R' is an $C_{1-6}$-alkyl group. Examples of $C_{1-6}$-alkoxy groups include methoxy, ethoxy, n-propoxy, isopropoxy, n-butoxy, isobutoxy and tert-butoxy. Particular examples are tert-butoxy, methoxy, ethoxy and isopropoxy. More particular examples are ethoxy, methoxy and tert-butoxy. Most particular examples are methoxy and ethoxy.

The term "halogen" and "halo" are used interchangeably herein and denote fluoro, chloro, bromo or iodo. Particular halogens include fluoro and chloro.

The term "halo-$C_{1-6}$-alkoxy" denotes an $C_{1-6}$-alkoxy group wherein at least one of the hydrogen atoms of the $C_{1-6}$-alkoxy group has been replaced by same or different halogen atoms. The term "perhalo-$C_{1-6}$-alkoxy" denotes an $C_{1-6}$-alkoxy group where all hydrogen atoms of the $C_{1-6}$-alkoxy group have been replaced by the same or different halogen atoms. Examples of halo-$C_{1-6}$-alkoxy include fluoromethoxy, difluoromethoxy, trifluoromethoxy, fluoroethoxy, difluoroethoxy, trifluoroethoxy, trifluoromethylethoxy, trifluorodimethylethoxy and pentafluoroethoxy. Particular halo-$C_{1-6}$-alkoxy groups include trifluoroethoxy, difluoromethoxy, difluoroethoxy, trifluoromethoxy, trifluoromethylethoxy and trifluorodimethylethoxy. More particular examples are trifluoroethoxy, difluoroethoxy and difluoromethoxy.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhalo-$C_{1-6}$-alkyl-$C_{1-6}$-alkyl" denotes an —$C_{1-6}$-alkyl-$C_{1-6}$-alkyl group where all hydrogen atoms of the alkyl group have been replaced by the same or different halogen atoms. Examples of halo-$C_{1-6}$-alkyl include fluoromethyl, difluoromethyl, trifluoromethyl, trifluoroethyl, trifluoromethylethyl and pentafluoroethyl. Particular halo-$C_{1-6}$-alkyl groups include difluoromethyl, trifluoromethyl, fluoromethyl, trifluoroethyl and difluoroethyl. More particular halo-$C_{1-6}$-alkyl groups include trifluoromethyl and difluoromethyl.

The term "hydroxy" denotes a —OH group.

The term "oxo" denotes a =O group.

The term "hydroxy-$C_{1-6}$-alkyl" denotes an $C_{1-6}$-alkyl group wherein one of the hydrogen atoms of the $C_{1-6}$-alkyl group has been replaced by a hydroxy group. Examples of hydroxy-$C_{1-6}$-alkyl include hydroxymethyl, hydroxyethyl, hydroxypropyl, hydroxymethylpropyl hydroxymethylethyl and hydroxybutyl. Particular examples include hydroxymethylpropyl and hydroxymethylethyl.

The term "amino" denotes a —$NH_2$ group.

The term "$C_{1-6}$-alkoxy-$C_{1-6}$-alkyl" denotes an $C_{1-6}$-alkyl group wherein at least one of the hydrogen atoms of the $C_{1-6}$-alkyl group has been replaced by an $C_{1-6}$-alkoxy group. Exemplary $C_{1-6}$-alkoxy-$C_{1-6}$-alkyl groups include methoxymethyl, ethoxymethyl, methoxymethyl, ethoxyethyl, methoxypropyl and ethoxypropyl.

The term "carbonyl" denotes a —C(O)— group.

The term "$C_{1-6}$-alkoxycarbonyl" denotes a group of the formula —C(O)—R', wherein R' is a $C_{1-6}$-alkoxy group. Examples of $C_{1-6}$-alkoxycarbonyl groups include groups wherein R' is methoxy, ethoxy, n-propoxy, isopropoxy, n-butoxy, isobutoxy or tert-butoxy. Particular examples of $C_{1-6}$-alkoxycarbonyl groups include wherein R' is ethoxy or tert-butoxy.

The term "$C_{1-6}$-alkylcarbonyl" of the formula —C(O)—R', wherein R' is an $C_{1-6}$-alkyl group. Examples of $C_{1-6}$-alkylcarbonyl groups include groups of the formula —C(O)—R', wherein R' is methyl or ethyl. Particular example of $C_{1-6}$-alkylcarbonyl groups include groups of the formula —C(O)—R', wherein R' is methyl.

The term "cyano" denotes a —C≡N group.

The term "$C_{3-8}$-cycloalkyl" denotes a monovalent saturated monocyclic or bicyclic hydrocarbon group of 3 to 8 ring carbon atoms. Bicyclic means a ring system consisting of two saturated carbocycles having one or two carbon atoms in common. Examples of monocyclic $C_{3-8}$-cycloalkyl are cyclopropyl, cyclobutanyl, cyclopentyl, cyclohexyl or cycloheptyl. Example of bicyclic $C_{3-8}$-cycloalkyl is spiro[3.3]heptanyl. Particular monocyclic $C_{3-8}$-cycloalkyl groups are cyclopropyl, cyclobutanyl. More particular monocyclic $C_{3-8}$-cycloalkyl groups include cyclopropyl.

The term "$C_{3-8}$-cycloalkoxy" denotes a group of the formula —O—R', wherein R' is a $C_{3-8}$-cycloalkyl group. Examples of cycloalkoxy group include cyclopropoxy, cyclobutoxy, cyclopentyloxy, cyclohexyloxy, cycloheptyloxy and cyclooctyloxy. Particular example is cyclopropoxy.

The term "$C_{3-8}$-cycloalkyl-$C_{1-6}$-alkoxy" denotes an $C_{1-6}$-alkoxy group wherein at least one of the hydrogen atoms of the $C_{1-6}$-alkoxy group is replaced by a $C_{3-8}$-cycloalkyl group. Examples of $C_{3-8}$-cycloalkyl-$C_{1-6}$-alkoxy include cyclopropylmethoxy, cyclobutylmethoxy, cyclopentylmethoxy, cyclohexylmethoxy, cyclopropylethoxy, cyclobutylethoxy, cyclopentylethoxy and cyclohexylethoxy.

Particular examples include cyclopropylethoxy.

The term "aryl" denotes a monovalent aromatic carbocyclic mono- or bicyclic ring system comprising 6 to 10 carbon ring atoms. Examples of aryl group include phenyl and naphthyl. Particular aryl groups include phenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyridinyl, pyrazolyl, imidazolyl, pyrimidinyl, pyridazinyl, imidazo[1,2-a]pyridinyl, oxadiazolyl. More particular heteroaryl groups include pyrazolyl.

The term "heteroaryloxy" denotes a group of the formula —O—R', wherein R' is a heteroaryl. Particular examples for R' include pyridinyl.

The term "heterocycloalkyl" denotes a monovalent saturated or partly unsaturated mono- or bicyclic ring system of 4 to 11 ring atoms, comprising 1, 2, or 3 ring heteroatoms selected from N, O and S, the remaining ring atoms being carbon. Bicyclic means consisting of two cycles having one or two ring atoms in common. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydrothiophenyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are oxabicyclo[2.2.1]heptanyl, oxaspiro[3.3]heptanyl, 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular heterocycloalkyl are pyrrolidinyl, piperidinyl, morpholinyl, piperazinyl, 2-oxa-6-azaspiro[3.3]heptanyl, 1,2,3,4,6,7,8,8a-octahydropyrrolo[1,2-a]pyrazinyl, 3,5,6,7,8,8a-hexahydro-1H-oxazolo[3,4-a]pyrazinyl, 2-oxa-7-azaspiro[3.5]nonanyl, 1-oxa-7-azaspiro[3.5]nonanyl, 3,3a,4,5,6,6a-hexahydro-1H-furo[3,4-c]pyrrolyl, 2,6-diazaspiro[3.3]heptanyl, 5-oxa-2-azaspiro[3.4]octanyl, 7-oxa-2-azaspiro[3.5]nonanyl, 3-oxa-9-azaspiro[5.5]undecanyl, 5-oxa-2-azaspiro[3.5]nonanyl, 1-oxa-9-azaspiro[5.5]undecanyl, 5-oxa-2-azaspiro[3.6]decanyl, 2-azaspiro[3.3]heptanyl, 4,7-diazaspiro[2.5]octanyl, 2-azaspiro[3.5]nonanyl, 6-oxa-3-azabicyclo[3.1.1]heptanyl, 1-oxa-8-azaspiro[4.5]decanyl, 8-oxa-3-azabicyclo[3.2.1]octanyl, 3-oxa-6-azabicyclo[3.1.1]heptanyl, 3-oxa-8-azabicyclo[3.2.1]octanyl and azetidinyl. More particular examples include morpholinyl, piperazinyl, azetidinyl, 5-oxa-2-azaspiro[3.5]nonanyl, 2,6-diazaspiro[3.3]heptanyl, 5-oxa-2-azaspiro[3.4]octanyl, 2-azaspiro[3.3]heptanyl. Even more particular examples include morpholinyl, piperazinyl, azetidinyl, 5-oxa-2-azaspiro[3.5]nonanyl. Most particular examples include azetidinyl, 5-oxa-2-azaspiro[3.5]nonanyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) or (II) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I) or (II), similar to the metabolically labile esters, which are capable of producing the parent compounds of general formula (I) or (II) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) or (II) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention is a compound according to formula (I) or (II) as described herein and pharmaceutically acceptable salts or esters thereof, in particular compounds according to formula (I) or (II) as described herein and pharmaceutically acceptable salts thereof, more particularly compounds according to formula (I) or (II) as described herein.

A certain embodiment of the invention relates to the compound of formula (I) or (II) as described herein, or a pharmaceutically acceptable salt thereof, wherein X is selected from
- i) N, and
- ii) $CR^{18}$;

Y is selected from
- i) N, and
- ii) CH;

Z is selected from
- i) N, and
- ii) CH;

$R^1$ is selected from
- i) $C_{1-6}$-alkyl,
- ii) halo-$C_{1-6}$-alkyl, and
- iii) halogen;

$R^2$ is $C_{1-6}$-alkyl;

$R^3$ is selected from
- i) pyrazolyl optionally substituted with $R^6$ and $R^7$,
- ii) pyridinyl optionally substituted with $R^6$ and $R^7$,
- iii) azetidinyl optionally substituted with $R^9$ and $R^{10}$,
- iv) isoindolinyl optionally substituted with $R^9$ and $R^{10}$,
- v) morpholinyl optionally substituted with $R^9$ and $R^{10}$,
- vi) piperazinyl optionally substituted with $R^9$ and $R^{10}$,
- vii) piperidinyl optionally substituted with $R^9$ and $R^{10}$,
- viii) pyrrolidinyl optionally substituted with $R^9$ and $R^{10}$.
- ix) oxaazaspirooctanyl optionally substituted with $R^9$ and $R^{10}$,
- x) oxaazaspirononanyl optionally substituted with $R^9$ and $R^{10}$,
- xi) amino substituted on the nitrogen atom by one or two substituents independently selected from $R^4$ and R', and
- xii) phenyl substituted with $R^6$ and $R^7$;

$R^4$ is $C_{1-6}$-alkyl;

$R^5$ is selected form
- i) H, and
- ii) $C_{1-6}$-alkyl;

$R^6$ is selected from
- i) $C_{1-6}$-alkyl,
- ii) $C_{1-6}$-alkoxy,
- iii) halogen,
- iv) halo-$C_{1-6}$-alkyl,
- v) $C_{3-8}$-cycloalkyl, and
- vi) cyano;

$R^7$ is selected from
- i) $C_{1-6}$-alkyl, and
- ii) $C_{1-6}$-alkoxy;

$R^9$, $R^{10}$ and $R^{11}$ are independently selected from
- i) $C_{1-6}$-alkyl,
- ii) $C_{1-6}$-alkoxy,
- iii) $C_{3-8}$-cycloalkoxy,
- iv) $C_{3-8}$-cycloalkyl,
- v) $C_{3-8}$-cycloalkyl-$C_{1-6}$-alkoxy,
- vi) $C_{1-6}$-alkoxy $C_{1-6}$-alkyl,
- vii) $C_{3-8}$-cycloalkylcarbonyl,
- viii) halo-$C_{1-6}$-alkoxy,
- ix) halogen,
- x) imidazolyl optionally substituted with $R^{12}$,
- xi) pyridinyl optionally substituted with $R^{12}$,
- xii) pyrazolyl optionally substituted with $R^{12}$,
- xiii) pyridazinyloxy optionally substituted with $R^{12}$,
- xiv) pyridinyloxy optionally substituted with $R^{12}$,
- xv) pyrimidinyloxy optionally substituted with $R^{12}$, $R^{12}$ is selected from
- i) halo-$C_{1-6}$-alkyl,
- ii) $C_{1-6}$-alkyl,
- iii) $C_{1-6}$-alkoxy, and
- iv) halogen;

$R^{18}$ is selected from
- i) H, and
- ii) halogen.

A certain embodiment of the invention relates to the compound of formula (I) or (II) as described herein, or a pharmaceutically acceptable salt thereof, wherein $R^1$ is selected from
- i) $C_{1-6}$-alkyl,
- ii) halo-$C_{1-6}$-alkyl, and
- iii) halogen.

A certain embodiment of the invention relates to the compound of formula (I) or (II) as described herein, or a pharmaceutically acceptable salt thereof, wherein $R^1$ is selected from
- iv) halo-$C_{1-6}$-alkyl, and
- v) halogen.

A certain embodiment of the invention relates to the compound of formula (I) or (II) as described herein, or a pharmaceutically acceptable salt thereof, wherein $R^2$ is $C_{1-6}$-alkyl.

A certain embodiment of the invention relates to the compound of formula (I) or (II) as described herein, or a pharmaceutically acceptable salt thereof, wherein $R^3$ is selected from
- i. pyridinyl optionally substituted with $R^6$, and
- ii. azetidinyl optionally substituted with $R^6$.

A certain embodiment of the invention relates to the compound of formula (I) or (II) as described herein, or a pharmaceutically acceptable salt thereof, wherein $R^4$ is $C_{1-6}$-alkyl.

A certain embodiment of the invention relates to the compound of formula (I) or (II) as described herein, or a pharmaceutically acceptable salt thereof, wherein $R^6$ is selected from
- i. $C_{1-6}$-alkyl,
- ii. $C_{1-6}$-alkoxy,
- iii. halogen,
- iv. halo-$C_{1-6}$-alkyl,
- v. $C_{3-8}$-cycloalkyl, and
- vi. cyano;

A certain embodiment of the invention relates to the compound of formula (I) or (II) as described herein, or a pharmaceutically acceptable salt thereof, wherein $R^6$ is $C_{1-6}$-alkoxy.

A certain embodiment of the invention relates to the compound of formula (I) or (II) as described herein, or a pharmaceutically acceptable salt thereof, wherein $R^7$ is selected from
- i. $C_{1-6}$-alkyl, and
- ii. $C_{1-6}$-alkoxy;

A certain embodiment of the invention relates to the compound of formula (I) or (II) as described herein, or a pharmaceutically acceptable salt thereof, wherein $R^9$, $R^{10}$ and $R^{11}$ are independently selected from
- i. $C_{1-6}$-alkyl,
- ii. $C_{1-6}$-alkoxy,
- iii. $C_{3-8}$-cycloalkoxy,
- iv. $C_{3-8}$-cycloalkyl,
- v. $C_{3-8}$-cycloalkyl-$C_{1-6}$-alkoxy,
- vi. $C_{1-6}$-alkoxy $C_{1-6}$-alkyl,
- vii. $C_{3-8}$-cycloalkylcarbonyl,
- viii. halo-$C_{1-6}$-alkoxy,
- ix. halogen,
- x. imidazolyl optionally substituted with $R^{12}$,
- xi. imidazolyloxy optionally substituted with $R^{12}$,
- xii. pyridinyl optionally substituted with $R^{12}$,
- xiii. pyridinyloxy optionally substituted with $R^{12}$,
- xiv. pyrazolyl optionally substituted with $R^{12}$, xv. pyrazolyloxy optionally substituted with $R^{12}$, xvi. pyridazinyl optionally substituted with $R^{12}$, xvii. pyridazinyloxy optionally substituted with $R^{12}$, xviii. pyrimidinyl optionally substituted with $R^{12}$, xix. pyrimidinyloxy optionally substituted with $R^{12}$, A certain embodiment of the invention relates to the compound of formula (I) or (II) as described herein, or a pharmaceutically acceptable salt thereof, wherein $R^9$, $R^{10}$ and $R^{11}$ are independently selected from i. $C_{1-6}$-alkyl, ii. $C_{1-6}$-alkoxy, iii. $C_{3-8}$-cycloalkoxy, iv. $C_{3-8}$-cycloalkyl, v. $C_{3-8}$-cycloalkyl-$C_{1-6}$-alkoxy, vi. $C_{1-6}$-alkoxy $C_{1-6}$-alkyl, vii. $C_{3-8}$-cycloalkylcarbonyl, viii. halo-$C_{1-6}$-alkoxy, ix. halogen, x. imidazolyl optionally substituted with $R^{12}$, xi. pyridinyl optionally substituted with $R^{12}$, xii. pyrazolyl optionally substituted with $R^{12}$, xiii. pyridazinyloxy optionally substituted with $R^{12}$, xiv. pyrimidinyloxy optionally substituted with $R^{12}$, A certain embodiment of the invention relates to the compound of formula (I) or (II) as described herein, or a pharmaceutically acceptable salt thereof, wherein $R^9$, $R^{10}$ and $R^{11}$ are independently selected from i. $C_{3-8}$-cycloalkoxy, ii. $C_{3-8}$-cycloalkyl-$C_{1-6}$-alkoxy, iii. halo-$C_{1-6}$-alkoxy, iv. pyrimidinyloxy optionally substituted with $R^{12}$.

A certain embodiment of the invention relates to the compound of formula (I) or (II) as described herein, or a pharmaceutically acceptable salt thereof, wherein Z is CH.

A certain embodiment of the invention relates to the compound of formula (I) or (II) as described herein, or a pharmaceutically acceptable salt thereof, wherein $R^{12}$ is halo-$C_{1-6}$-alkyl.

A certain embodiment of the invention relates to the compound of formula (I) or (II) as described herein, or a pharmaceutically acceptable salt thereof, wherein $R^{18}$ is halogen.

A certain embodiment of the invention relates to the compound of formula (I) or (II) as described herein, or a pharmaceutically acceptable salt thereof, wherein the compound is a compound of formula (I).

A certain embodiment of the invention relates to the compound of formula (I) or (II) as described herein, or a pharmaceutically acceptable salt thereof, wherein the compound is a compound of formula (II).

A certain embodiment of the invention relates to the compound of formula (I) or (II) as described herein, or a pharmaceutically acceptable salt thereof, wherein are selected from 2-[[5-methyl-3-(6-methyl-3-pyridyl)triazol-4-yl]methyl]-5-[rac-(2S,6R)-2,6-dimethylmorpholin-4-yl]pyridazin-3-one;

2-[[3-methyl-5-(6-methyl-3-pyridyl)triazol-4-yl]methyl]-5-[rac-(2S,6R)-2,6-dimethylmorpholin-4-yl]pyridazin-3-one;

2-[[5-(4-chloro-2-fluoro-phenyl)-3-methyl-triazol-4-yl]methyl]-5-[rac-(2S,6R)-2,6-dimethylmorpholin-4-yl]pyridazin-3-one;

2-[[3-(4-chloro-2-fluoro-phenyl)-5-methyl-triazol-4-yl]methyl]-5-morpholino-pyridazin-3-one;

2-[[3-(4-chloro-2-fluoro-phenyl)-5-methyl-triazol-4-yl]methyl]-5-(dimethylamino)pyridazin-3-one;

2-[[3-(4-chloro-2-fluoro-phenyl)-5-methyl-triazol-4-yl]methyl]-5-[4-(cyclopropanecarbonyl)piperazin-1-yl]pyridazin-3-one;

2-[[3-(4-chloro-2-fluoro-phenyl)-5-methyl-triazol-4-yl]methyl]-5-[rac-(2S,6R)-2,6-dimethylmorpholin-4-yl]pyridazin-3-one;

2-[[3-methyl-5-(6-methyl-3-pyridyl)triazol-4-yl]methyl]-5-pyrrolidin-1-yl-pyridazin-3-one;

2-[[3-methyl-5-(6-methyl-3-pyridyl)triazol-4-yl]methyl]-5-morpholino-pyridazin-3-one;

5-(3,3-dimethylpyrrolidin-1-yl)-2-[[3-methyl-5-(6-methyl-3-pyridyl)triazol-4-yl]methyl]pyridazin-3-one;

5-(2,2-dimethylmorpholin-4-yl)-2-[[3-methyl-5-(6-methyl-3-pyridyl)triazol-4-yl]methyl]pyridazin-3-one;

5-[(2S,6S)-2,6-dimethylmorpholin-4-yl]-2-[[3-methyl-5-(6-methyl-3-pyridyl)triazol-4-yl]methyl]pyridazin-3-one;

2-[[3-(4-chlorophenyl)-5-methyl-triazol-4-yl]methyl]-5-(dimethylamino)pyridazin-3-one;

2-[[3-(4-chlorophenyl)-5-methyl-triazol-4-yl]methyl]-5-piperazin-1-yl-pyridazin-3-one;

2-[[5-(4-chloro-2-fluoro-phenyl)-3-methyl-triazol-4-yl]methyl]-5-(dimethylamino)pyridazin-3-one;

2-[[5-(4-chloro-2-fluoro-phenyl)-3-methyl-triazol-4-yl]methyl]-5-morpholino-pyridazin-3-one;

2-[[5-(4-chloro-2-fluoro-phenyl)-3-methyl-triazol-4-yl]methyl]-5-(4-cyclopropylpiperazin-1-yl)pyridazin-3-one;

2-[[3-methyl-5-(6-methyl-3-pyridyl)triazol-4-yl]methyl]-5-[(2R)-2-methylpyrrolidin-1-yl]pyridazin-3-one;

5-[(2S)-2-(methoxymethyl)pyrrolidin-1-yl]-2-[[3-methyl-5-(6-methyl-3-pyridyl)triazol-4-yl]methyl]pyridazin-3-one;

2-[[3-(4-chlorophenyl)-5-methyl-triazol-4-yl]methyl]-5-[rac-(2S,6R)-2,6-dimethylmorpholin-4-yl]pyridazin-3-one;

2-[[5-(4-chloro-2-fluoro-phenyl)-3-methyl-triazol-4-yl]methyl]-5-[4-(cyclopropanecarbonyl)piperazin-1-yl]pyridazin-3-one;

2-[[5-(4-chloro-2-fluoro-phenyl)-3-methyl-triazol-4-yl]methyl]-5-(methylamino)pyridazin-3-one;

2-[[3-(4-chloro-2-fluoro-phenyl)-5-methyl-triazol-4-yl]methyl]-5-(3-ethoxyazetidin-1-yl)pyridazin-3-one;

2-[[3-(4-chloro-2-fluoro-phenyl)-5-methyl-triazol-4-yl]methyl]-5-isoindolin-2-yl-pyridazin-3-one;

2-[[5-methyl-3-(6-methyl-3-pyridyl)triazol-4-yl]methyl]-5-[(2R)-2-methylpyrrolidin-1-yl]pyridazin-3-one;

2-[[5-(4-chloro-2-fluoro-phenyl)-3-methyl-triazol-4-yl]methyl]-5-(3-methoxyazetidin-1-yl)pyridazin-3-one;

2-[[5-(4-chloro-2-fluoro-phenyl)-3-methyl-triazol-4-yl]methyl]-5-(3-ethoxyazetidin-1-yl)pyridazin-3-one;

2-[[5-(4-chloro-2-fluoro-phenyl)-3-methyl-triazol-4-yl]methyl]-5-[3-(cyclopropylmethoxy)azetidin-1-yl]pyridazin-3-one;

2-[[5-(4-chloro-2-fluoro-phenyl)-3-methyl-triazol-4-yl]methyl]-5-(5-oxa-2-azaspiro[3.4]octan-2-yl)pyridazin-3-one;

2-[[5-(4-chlorophenyl)-3-methyl-triazol-4-yl]methyl]-5-[rac-(2R,6S)-2,6-dimethylmorpholin-4-yl]pyridazin-3-one;

2-[[5-(4-chlorophenyl)-3-methyl-triazol-4-yl]methyl]-5-(dimethylamino)pyridazin-3-one;

2-[[5-(4-chloro-2-fluoro-phenyl)-3-methyl-triazol-4-yl]methyl]-5-[(7S)-7-methoxy-5-oxa-2-azaspiro[3.4]octan-2-yl]pyridazin-3-one;

2-[[5-(4-chloro-2-fluoro-phenyl)-3-methyl-triazol-4-yl]methyl]-5-[(7R)-7-methoxy-5-oxa-2-azaspiro[3.4]octan-2-yl]pyridazin-3-one;

2-[[3-(4-chloro-2-fluoro-phenyl)-5-methyl-triazol-4-yl]methyl]-5-[3-(2,2,2-trifluoroethoxy)azetidin-1-yl]pyridazin-3-one;

2-[[3-(4-chloro-2-fluoro-phenyl)-5-methyl-triazol-4-yl]methyl]-5-[(2S)-2-methylmorpholin-4-yl]pyridazin-3-one;

2-[[3-(4-chloro-2-fluoro-phenyl)-5-methyl-triazol-4-yl]methyl]-5-[(2R)-2-methylmorpholin-4-yl]pyridazin-3-one;

2-[[3-(4-chloro-2-fluoro-phenyl)-5-methyl-triazol-4-yl]methyl]-5-[(2S,6S)-2,6-dimethylmorpholin-4-yl]pyridazin-3-one;

2-[[3-(4-chloro-2-fluoro-phenyl)-5-methyl-triazol-4-yl]methyl]-5-[4-(2-methylimidazol-1-yl)-1-piperidyl]pyridazin-3-one;

2-[[3-(4-chloro-2-fluoro-phenyl)-5-methyl-triazol-4-yl]methyl]-5-[4-(2-methoxy-3-pyridyl)piperazin-1-yl]pyridazin-3-one;

2-[[5-(4-chlorophenyl)-3-methyl-triazol-4-yl]methyl]-5-[(3S)-4-isopropyl-3-methyl-piperazin-1-yl]pyridazin-3-one;

2-[[5-(4-chlorophenyl)-3-methyl-triazol-4-yl]methyl]-5-(3-ethoxyazetidin-1-yl)pyridazin-3-one;

2-[[5-(4-chloro-2-fluoro-phenyl)-3-methyl-triazol-4-yl]methyl]-5-[(3R)-3-isopropoxypyrrolidin-1-yl]pyridazin-3-one;

2-[[5-(4-chloro-2-fluoro-phenyl)-3-methyl-triazol-4-yl]methyl]-5-[3-(2-pyridyloxy)azetidin-1-yl]pyridazin-3-one;

2-[[5-(4-chloro-2-fluoro-phenyl)-3-methyl-triazol-4-yl]methyl]-5-[(3S)-4-isopropyl-3-methyl-piperazin-1-yl]pyridazin-3-one;

2-[[5-(4-chloro-2-fluoro-phenyl)-3-methyl-triazol-4-yl]methyl]-5-[(2S)-2-methylmorpholin-4-yl]pyridazin-3-one;

2-[[5-(4-chloro-2-fluoro-phenyl)-3-methyl-triazol-4-yl]methyl]-5-[(2R)-2-methylmorpholin-4-yl]pyridazin-3-one;

2-[[3-(4-chloro-2-fluoro-phenyl)-5-methyl-triazol-4-yl]methyl]-5-[4-(2-ethylimidazol-1-yl)-1-piperidyl]pyridazin-3-one;

2-[[5-(4-chloro-2-fluoro-phenyl)-3-methyl-triazol-4-yl]methyl]-5-(3-isopropoxyazetidin-1-yl)pyridazin-3-one;

2-[[5-(4-chloro-2-fluoro-phenyl)-3-methyl-triazol-4-yl]methyl]-5-[3-(cyclobutoxy)azetidin-1-yl]pyridazin-3-one;

2-[[5-(4-chloro-2-fluoro-phenyl)-3-methyl-triazol-4-yl]methyl]-5-[3-(2,2,2-trifluoroethoxy)azetidin-1-yl]pyridazin-3-one;

2-[[5-(4-chloro-2-fluoro-phenyl)-3-methyl-triazol-4-yl]methyl]-5-(3-propoxyazetidin-1-yl)pyridazin-3-one;

2-[[5-(4-chloro-2-fluoro-phenyl)-3-methyl-triazol-4-yl]methyl]-5-[3-[(6-chloro-3-pyridyl)oxy]azetidin-1-yl]pyridazin-3-one;

2-[[5-(4-chloro-2-fluoro-phenyl)-3-methyl-triazol-4-yl]methyl]-5-[3-(difluoromethoxy)azetidin-1-yl]pyridazin-3-one;

2-[[5-(4-chloro-2-fluoro-phenyl)-3-methyl-triazol-4-yl]methyl]-5-[3-(2,2-difluoroethoxy)azetidin-1-yl]pyridazin-3-one;

2-[[5-(4-chloro-2-fluoro-phenyl)-3-methyl-triazol-4-yl]methyl]-5-[3-[(2-chloro-4-pyridyl)oxy]azetidin-1-yl]pyridazin-3-one;

2-[[3-(4-chloro-2-fluoro-phenyl)-5-methyl-triazol-4-yl]methyl]-5-(4-methoxyphenyl)pyridazin-3-one;

2-[[3-(4-chloro-2-fluoro-phenyl)-5-methyl-triazol-4-yl]methyl]-5-[2-(trifluoromethyl)-4-pyridyl]pyridazin-3-one;

2-[[5-(2,4-difluorophenyl)-3-methyl-triazol-4-yl]methyl]-5-[rac-(2R,6S)-2,6-dimethylmorpholin-4-yl]pyridazin-3-one;

2-[[5-(4-chlorophenyl)-3-methyl-triazol-4-yl]methyl]-5-[3-(2,2,2-trifluoroethoxy)azetidin-1-yl]pyridazin-3-one;

2-[[5-(4-chlorophenyl)-3-methyl-triazol-4-yl]methyl]-5-[3-(2,2-difluoroethoxy)azetidin-1-yl]pyridazin-3-one;

2-[[5-(4-chloro-2-fluoro-phenyl)-3-methyl-triazol-4-yl]methyl]-5-(4-methoxyphenyl)pyridazin-3-one;

2-[[5-(4-chloro-2-fluoro-phenyl)-3-methyl-triazol-4-yl]methyl]-5-(6-methoxy-3-pyridyl)pyridazin-3-one;

2-[[5-(4-chloro-2-fluoro-phenyl)-3-methyl-triazol-4-yl]methyl]-5-(2-methoxy-4-pyridyl)pyridazin-3-one;

2-[[5-(4-chloro-2-fluoro-phenyl)-3-methyl-triazol-4-yl]methyl]-5-(1-methylpyrazol-4-yl)pyridazin-3-one;

2-[[3-(4-chloro-2-fluoro-phenyl)-5-methyl-triazol-4-yl]methyl]-5-(1-cyclopropylpyrazol-4-yl)pyridazin-3-one;

2-[[5-(4-chloro-2-fluoro-phenyl)-3-methyl-triazol-4-yl]methyl]-5-(6-ethoxy-5-methyl-3-pyridyl)pyridazin-3-one;

2-[[5-(4-chloro-2-fluoro-phenyl)-3-methyl-triazol-4-yl]methyl]-5-(1-cyclopropylpyrazol-4-yl)pyridazin-3-one;

2-[[3-(4-chloro-2-fluoro-phenyl)-5-methyl-triazol-4-yl]methyl]-5-(5-chloro-6-methoxy-3-pyridyl)pyridazin-3-one;

2-[[5-(4-chloro-2-fluoro-phenyl)-3-methyl-triazol-4-yl]methyl]-5-(5-chloro-6-methoxy-3-pyridyl)pyridazin-3-one;

2-[[5-[2-fluoro-4-(trifluoromethyl)phenyl]-3-methyl-triazol-4-yl]methyl]-5-(3-isopropoxyazetidin-1-yl)pyridazin-3-one; 5-[3-(difluoromethoxy)azetidin-1-yl]-2-[[5-[2-fluoro-4-(trifluoromethyl)phenyl]-3-methyl-triazol-4-yl]methyl]pyridazin-3-one; 5-(3-ethoxyazetidin-1-yl)-2-[[5-[2-fluoro-4-(trifluoromethyl)phenyl]-3-methyl-triazol-4-yl]methyl]pyridazin-3-one;

2-[[5-(4-chloro-2-fluoro-phenyl)-3-methyl-triazol-4-yl]methyl]-5-(3-pyrazin-2-yloxyazetidin-1-yl)pyridazin-3-one;

2-[[5-[2-fluoro-4-(trifluoromethyl)phenyl]-3-methyl-triazol-4-yl]methyl]-5-[3-(2,2,2-trifluoroethoxy)azetidin-1-yl]pyridazin-3-one;

2-[[5-[2-fluoro-4-(trifluoromethyl)phenyl]-3-methyl-triazol-4-yl]methyl]-5-(5-oxa-2-azaspiro[3.4]octan-2-yl)pyridazin-3-one; 5-[3-(2,2-difluoroethoxy)azetidin-1-yl]-2-[[5-[2-fluoro-4-(trifluoromethyl)phenyl]-3-methyl-triazol-4-yl]methyl]pyridazin-3-one; 5-[3-(cyclobutoxy)azetidin-1-yl]-2-[[5-[2-fluoro-4-(trifluoromethyl)phenyl]-3-methyl-triazol-4-yl]methyl]pyridazin-3-one;

2-[[5-(4-chloro-2-fluoro-phenyl)-3-methyl-triazol-4-yl]methyl]-5-(3-pyrimidin-4-yloxyazetidin-1-yl)pyridazin-3-one;

2-[[5-(4-chloro-2-fluoro-phenyl)-3-methyl-triazol-4-yl]methyl]-5-(3-pyridazin-3-yloxyazetidin-1-yl)pyridazin-3-one;

2-[[5-(4-chloro-2-fluoro-phenyl)-3-methyl-triazol-4-yl]methyl]-5-[3-[(5-chloro-2-pyridyl)oxy]azetidin-1-yl]pyridazin-3-one;

5-(2-methoxy-4-pyridyl)-2-[[3-methyl-5-(6-methyl-3-pyridyl)triazol-4-yl]methyl]pyridazin-3-one;

5-(5-chloro-6-methoxy-3-pyridyl)-2-[[3-methyl-5-(6-methyl-3-pyridyl)triazol-4-yl]methyl]pyridazin-3-one;

2-[[5-[2-fluoro-4-(trifluoromethyl)phenyl]-3-methyl-triazol-4-yl]methyl]-5-(3-pyridazin-3-yloxyazetidin-1-yl)pyridazin-3-one;

2-[[5-[2-fluoro-4-(trifluoromethyl)phenyl]-3-methyl-triazol-4-yl]methyl]-5-[3-(2-pyridyloxy)azetidin-1-yl]pyridazin-3-one;

2-[[5-(4-chloro-2-fluoro-phenyl)-3-ethyl-triazol-4-yl]methyl]-5-[3-(cyclobutoxy)azetidin-1-yl]pyridazin-3-one;

2-[[5-(4-chloro-2-fluoro-phenyl)-3-ethyl-triazol-4-yl]methyl]-5-[3-(2,2-difluoroethoxy)azetidin-1-yl]pyridazin-3-one;

2-[[5-(4-chloro-2-fluoro-phenyl)-3-ethyl-triazol-4-yl]methyl]-5-[3-(2,2,2-trifluoroethoxy)azetidin-1-yl]pyridazin-3-one;

2-[[5-(4-chloro-2-fluoro-phenyl)-3-ethyl-triazol-4-yl]methyl]-5-[3-(difluoromethoxy)azetidin-1-yl]pyridazin-3-one;

2-[[5-[2-fluoro-4-(trifluoromethyl)phenyl]-3-methyl-triazol-4-yl]methyl]-5-(3-pyrazin-2-yloxyazetidin-1-yl)pyridazin-3-one;

2-[[5-(4-chloro-2-fluoro-phenyl)-3-ethyl-triazol-4-yl]methyl]-5-(3-isopropoxyazetidin-1-yl)pyridazin-3-one;

2-[[5-(4-chloro-2-fluoro-phenyl)-3-ethyl-triazol-4-yl]methyl]-5-(3-ethoxyazetidin-1-yl)pyridazin-3-one;

2-[[5-(4-chloro-2-fluoro-phenyl)-3-ethyl-triazol-4-yl]methyl]-5-[(3S)-4-isopropyl-3-methyl-piperazin-1-yl]pyridazin-3-one;

5-[3-[(6-chloro-3-pyridyl)oxy]azetidin-1-yl]-2-[[5-[2-fluoro-4-(trifluoromethyl)phenyl]-3-methyl-triazol-4-yl]methyl]pyridazin-3-one;

2-[[5-[2-fluoro-4-(trifluoromethyl)phenyl]-3-methyl-triazol-4-yl]methyl]-5-[(3S)-4-isopropyl-3-methyl-piperazin-1-yl]pyridazin-3-one;

2-[[5-(4-chloro-2-fluoro-phenyl)-3-methyl-triazol-4-yl]methyl]-5-(5-oxa-2-azaspiro[3.5]nonan-2-yl)pyridazin-3-one;

5-(3-tert-butoxyazetidin-1-yl)-2-[[5-(4-chloro-2-fluoro-phenyl)-3-methyl-triazol-4-yl]methyl]pyridazin-3-one;

5-(3-tert-butoxyazetidin-1-yl)-2-[[5-(4-chloro-2-fluoro-phenyl)-3-ethyl-triazol-4-yl]methyl]pyridazin-3-one;

2-[[5-(4-chloro-2-fluoro-phenyl)-3-methyl-triazol-4-yl]methyl]-5-[3-[6-(trifluoromethyl)pyrazin-2-yl]oxyazetidin-1-yl]pyridazin-3-one;

2-[[5-(4-chloro-2-fluoro-phenyl)-3-methyl-triazol-4-yl]methyl]-5-[3-(2-methylpyrimidin-4-yl)oxyazetidin-1-yl]pyridazin-3-one;

2-[[5-(4-chloro-2-fluoro-phenyl)-3-methyl-triazol-4-yl]methyl]-5-[3-[2-(trifluoromethyl)pyrimidin-4-yl]oxyazetidin-1-yl]pyridazin-3-one;

2-[[5-(4-chloro-2-fluoro-phenyl)-3-ethyl-triazol-4-yl]methyl]-5-[3-[(6-chloro-3-pyridyl)oxy]azetidin-1-yl]pyridazin-3-one;

2-[[5-(4-chloro-2-fluoro-phenyl)-3-ethyl-triazol-4-yl]methyl]-5-(3-pyridazin-3-yloxyazetidin-1-yl)pyridazin-3-one;

2-[[5-(4-chloro-2-fluoro-phenyl)-3-methyl-triazol-4-yl]methyl]-5-(6-ethoxy-3-pyridyl)pyridazin-3-one;

2-[[5-(4-chloro-2-fluoro-phenyl)-3-methyl-triazol-4-yl]methyl]-5-(6-methoxy-5-methyl-3-pyridyl)pyridazin-3-one;

2-[[5-(4-chloro-2-fluoro-phenyl)-3-ethyl-triazol-4-yl]methyl]-5-(1-cyclopropylpyrazol-4-yl)pyridazin-3-one;

2-[[5-(4-chloro-2-fluoro-phenyl)-3-methyl-triazol-4-yl]methyl]-5-[1-(2,2-difluoroethyl)pyrazol-4-yl]pyridazin-3-one; 6-[1-[[5-(4-chloro-2-fluoro-phenyl)-3-methyl-triazol-4-yl]methyl]-6-oxo-pyridazin-4-yl]pyridine-2-carbonitrile;

2-[[5-(4-chloro-2-fluoro-phenyl)-3-methyl-triazol-4-yl]methyl]-5-(6-chloro-5-methoxy-3-pyridyl)pyridazin-3-one;

2-[[5-(6-chloro-3-pyridyl)-3-methyl-triazol-4-yl]methyl]-5-[(2R)-2-methylpyrrolidin-1-yl]pyridazin-3-one;

2-[[5-(4-chloro-2-fluoro-phenyl)-3-ethyl-triazol-4-yl]methyl]-5-(5-chloro-6-methoxy-3-pyridyl)pyridazin-3-one;

6-[1-[[5-(4-chloro-2-fluoro-phenyl)-3-ethyl-triazol-4-yl]methyl]-6-oxo-pyridazin-4-yl]pyridine-2-carbonitrile;

2-[[5-(6-chloro-3-pyridyl)-3-methyl-triazol-4-yl]methyl]-5-[rac-(2S,6R)-2,6-dimethylmorpholin-4-yl]pyridazin-3-one;

2-[[5-(4-chloro-2-fluoro-phenyl)-3-methyl-triazol-4-yl]methyl]-5-[3-(5-methylpyrazol-1-yl)azetidin-1-yl]pyridazin-3-one;

5-(5-chloro-6-methoxy-3-pyridyl)-2-[[3-methyl-5-(6-methylpyridazin-3-yl)triazol-4-yl]methyl]pyridazin-3-one;

5-(3-ethoxyazetidin-1-yl)-2-[[3-methyl-5-[5-(trifluoromethyl)pyrimidin-2-yl]triazol-4-yl]methyl]pyridazin-3-one;

5-(3-isopropoxyazetidin-1-yl)-2-[[3-methyl-5-[5-(trifluoromethyl)pyrimidin-2-yl]triazol-4-yl]methyl]pyridazin-3-one;

5-[3-(cyclobutoxy)azetidin-1-yl]-2-[[3-methyl-5-[5-(trifluoromethyl)pyrimidin-2-yl]triazol-4-yl]methyl]pyridazin-3-one;

5-(5-chloro-6-methoxy-3-pyridyl)-2-[[3-methyl-5-[5-(trifluoromethyl)pyrimidin-2-yl]triazol-4-yl]methyl]pyridazin-3-one;

5-[3-(2,2-difluoroethoxy)azetidin-1-yl]-2-[[3-methyl-5-[5-(trifluoromethyl)pyrimidin-2-yl]triazol-4-yl]methyl]pyridazin-3-one;

2-[[3-methyl-5-[5-(trifluoromethyl)pyrimidin-2-yl]triazol-4-yl]methyl]-5-[3-(2,2,2-trifluoroethoxy)azetidin-1-yl]pyridazin-3-one;

5-[3-(difluoromethoxy)azetidin-1-yl]-2-[[3-methyl-5-[5-(trifluoromethyl)pyrimidin-2-yl]triazol-4-yl]methyl]pyridazin-3-one;

2-[[5-(4-chloro-2-fluoro-phenyl)-3-ethyl-triazol-4-yl]methyl]-5-[(7R)-7-methyl-5-oxa-2-azaspiro[3.5]nonan-2-yl]pyridazin-3-one;

5-(5-chloro-6-methoxy-3-pyridyl)-2-[[3-methyl-5-[6-(trifluoromethyl)pyridazin-3-yl]triazol-4-yl]methyl]pyridazin-3-one;

2-[[5-(4-chloro-2-fluoro-phenyl)-3-ethyl-triazol-4-yl]methyl]-5-[(7S)-7-fluoro-5-oxa-2-azaspiro[3.5]nonan-2-yl]pyridazin-3-one;

2-[[5-(4-chloro-2-fluoro-phenyl)-3-ethyl-triazol-4-yl]methyl]-5-[(7R)-7-fluoro-5-oxa-2-azaspiro[3.5]nonan-2-yl]pyridazin-3-one;

2-[[5-(4-chloro-2-fluoro-phenyl)-3-methyl-triazol-4-yl]methyl]-5-[(7S)-7-fluoro-5-oxa-2-azaspiro[3.5]nonan-2-yl]pyridazin-3-one.

A certain embodiment of the invention relates to the compound of formula (I) or (II) as described herein, or a pharmaceutically acceptable salt thereof, wherein are selected from 2-[[5-(4-chloro-2-fluoro-phenyl)-3-methyl-triazol-4-yl]methyl]-5-[3-(cyclopropylmethoxy)azetidin-1-yl]pyridazin-3-one;

2-[[5-(4-chloro-2-fluoro-phenyl)-3-methyl-triazol-4-yl]methyl]-5-[3-(cyclobutoxy)azetidin-1-yl]pyridazin-3-one;

2-[[5-(4-chloro-2-fluoro-phenyl)-3-methyl-triazol-4-yl]methyl]-5-(6-methoxy-3-pyridyl)pyridazin-3-one;

5-[3-(2,2-difluoroethoxy)azetidin-1-yl]-2-[[5-[2-fluoro-4-(trifluoromethyl)phenyl]-3-methyl-triazol-4-yl]methyl]pyridazin-3-one;

5-[3-(cyclobutoxy)azetidin-1-yl]-2-[[5-[2-fluoro-4-(trifluoromethyl)phenyl]-3-methyl-triazol-4-yl]methyl]pyridazin-3-one;

2-[[5-(4-chloro-2-fluoro-phenyl)-3-methyl-triazol-4-yl]methyl]-5-[3-[2-(trifluoromethyl)pyrimidin-4-yl]oxyazetidin-1-yl]pyridazin-3-one;

5-[3-(difluoromethoxy)azetidin-1-yl]-2-[[3-methyl-5-[5-(trifluoromethyl)pyrimidin-2-yl]triazol-4-yl]methyl]pyridazin-3-one.

In a particular embodiment, the present invention provides pharmaceutically acceptable salts of the compounds according to formula (I) or (II) as described herein, especially hydrochloride salts. In a further particular embodiment, the present invention provides compounds according to formula (I) or (II) as described herein as free bases.

In some embodiments, the compounds of formula (I) or (II) are isotopically-labeled by having one or more atoms therein replaced by an atom having a different atomic mass or mass number. Such isotopically-labeled (i.e., radiolabeled) compounds of formula (I) or (II) are considered to be within the scope of this disclosure. Examples of isotopes that can be incorporated into the compounds of formula (I) or (II) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{31}P$, $^{32}P$, $^{35}S$, $^{18}F$, $^{36}Cl$, $^{123}I$, and $^{125}I$, respectively. Certain isotopically-labeled compounds of formula (I) or (II), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) or (II) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) or (II) can generally be prepared by conventional techniques known to those skilled in the art or by processes analogous to those described in the Examples as set out below using an appropriate isotopically-labeled reagent in place of the non-labeled reagent previously employed.

Processes for the manufacture of a compound of formula (I) or (II) as described herein are also an object of the invention.

The preparation of compounds of formula (I) or (II) of the present invention may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

The preparation of compounds of formula Ia and Ib of the present invention may be carried out in sequential or convergent synthetic routes. Synthesis of the compounds of the invention are shown in the following schemes 1-9 and in the description of 126 specific examples. The skills required for carrying out the reactions and purifications of the resulting products are known to those skilled in the art. The substituents and indices used in the following description of the processes have the significance given herein before unless indicated to the contrary.

In more detail, the compounds of formula (I) or (II) can be manufactured by the methods given below, by the methods given in the examples or by analogous methods. Appropriate reaction conditions for the individual reaction steps are known to a person skilled in the art. The reaction sequence is not limited to the one displayed in schemes 1-9, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula (I) or (II) and their pharmaceutically acceptable salts can be prepared by a process described below (Scheme 1).

Scheme 1: synthesis of pyridazinones (I) and (II);
wherein all definitions are as described above and in the claims

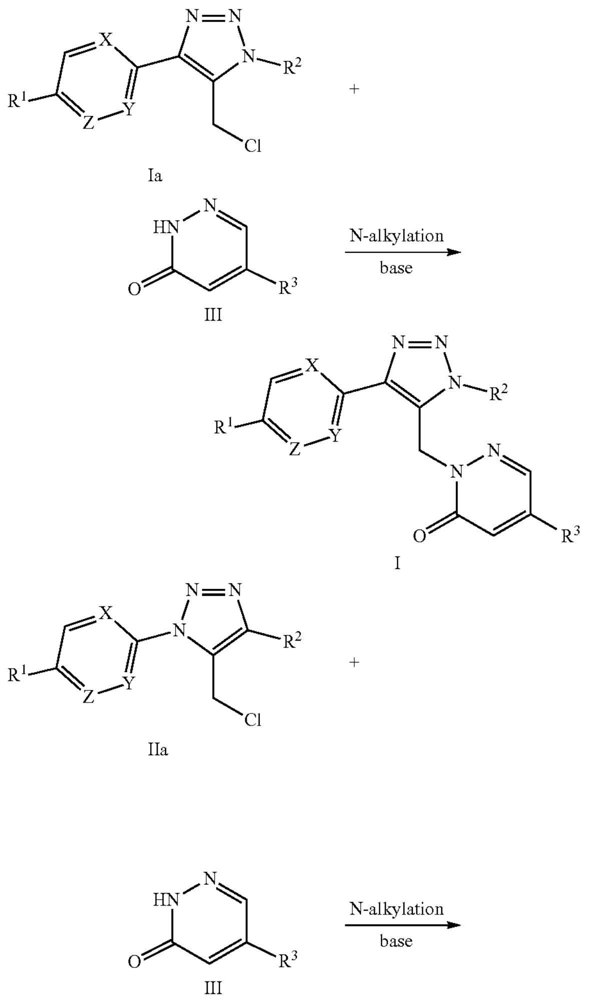

Ia

III

I

IIa

III

-continued

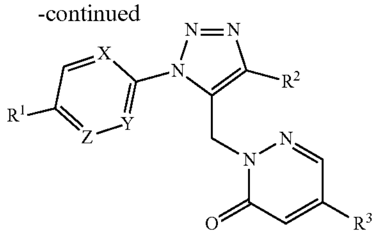

II

According to Scheme 1, a compound of formula (I) or (II) can be prepared by simple N-alkylation reaction between alkyl chlorides Ia or Ha and a pyridazinone of formula III in presence of a base (e.g. $K_2CO_3$, $Cs_2CO_3$ and KO$^t$Bu).

In alternative, as illustrated in Scheme 2, pyridazinones Ia or Ib can be accessed by a Mitsunobu reaction between alcohols of formula IVa or IVb and a pyridazinone of formula III in presence of diethyl azodicarboxylate and triphenylphospine.

Scheme 2: alternative synthesis of pyridazinones (I) and (II); where all definitions are as described above and in the claims

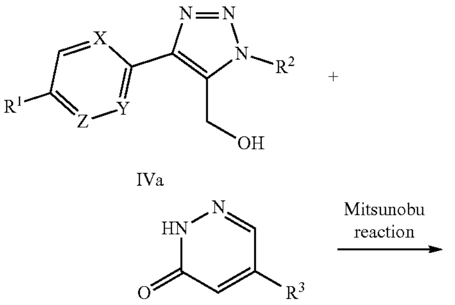

IVa

III

-continued

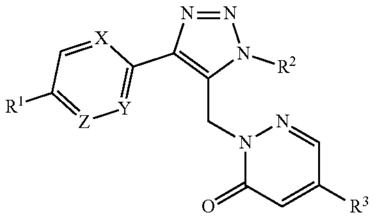

I

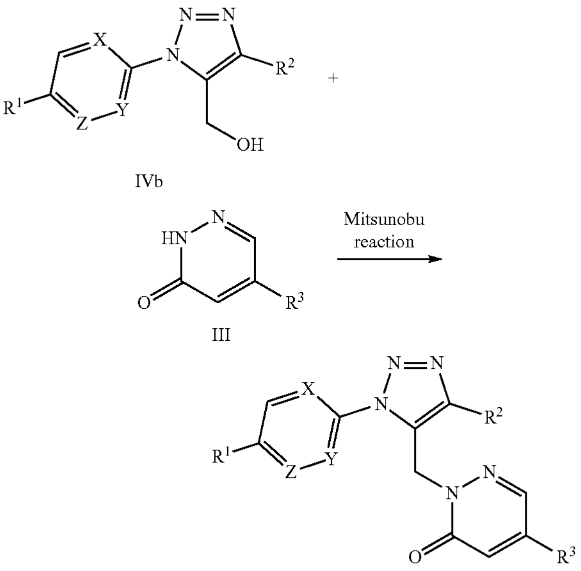

IVb

III

II

Synthesis of Alkyl Chlorides Ta and Alcohols IVa is Highlighted in Scheme 3

Scheme 3: synthesis of alkyl chlorides Ia and alcohols IVa; wherein all definitions are as described above and in the claims

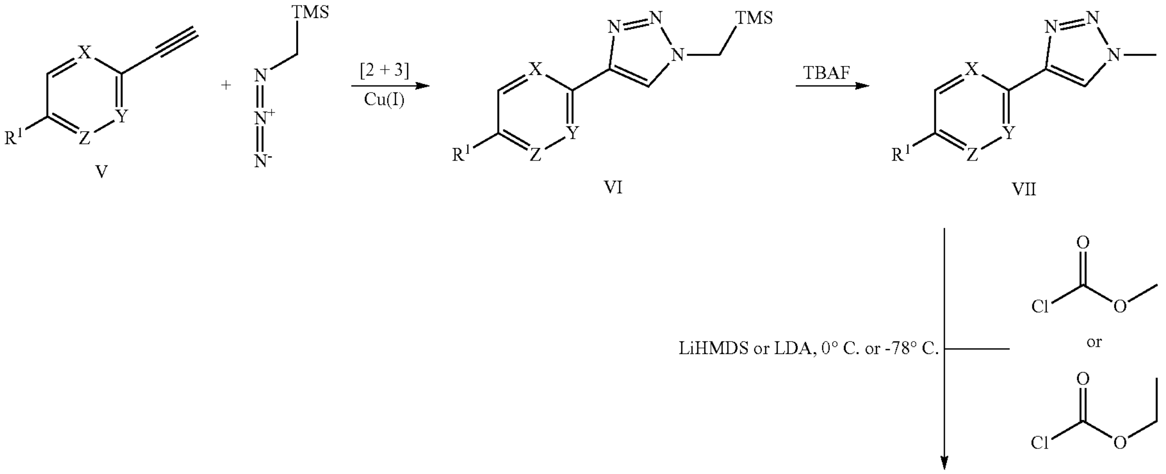

V

VI

VII

-continued

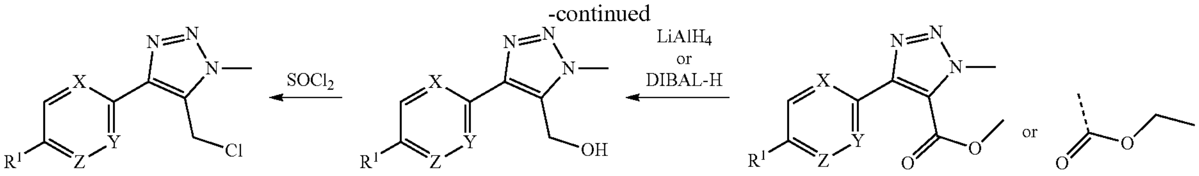

Ia IVa VIII

Commercially available alkynes V are subjected to a Cu(J)-mediated 1,3-dipolar cycloaddition reaction with trimethylsilylmethyl azide in presence of a base (e.g. DIPEA) to corresponding 1,2,3-triazoles VI. Removal of the trimethylsilyl residue was facilitated by treatment with TBAF in tetrahydrofuran. Kinetic deprotonation using a strong base (LiHMDS or LDA) at low temperatures (−78° C. to 0° C.) followed by quenching with ethyl or methyl chloroformate yields 1,2,3-triazoles of general formula VIII. Their reduction to alcohols IVa can be accomplished directly with $LiAlH_4$ or DIBAL-H at controlled temperature. Final conversion to desired alkyl chlorides Ta is accomplished by exposure to thionyl chloride.

Scheme 4: synthesis of alkyl chlorides Ia and alcohols IVa; wherein all definitions are as described above and in the claims

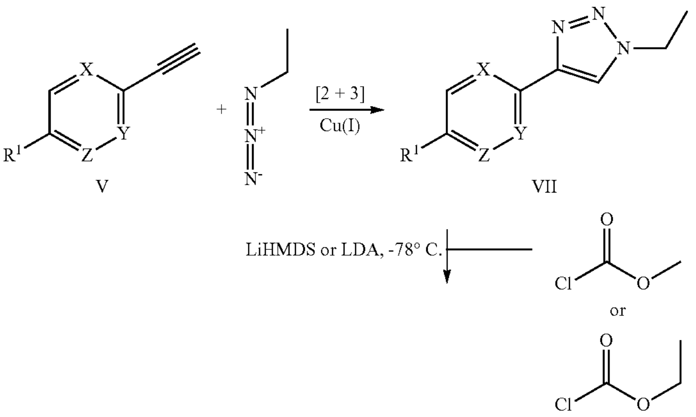

V VII

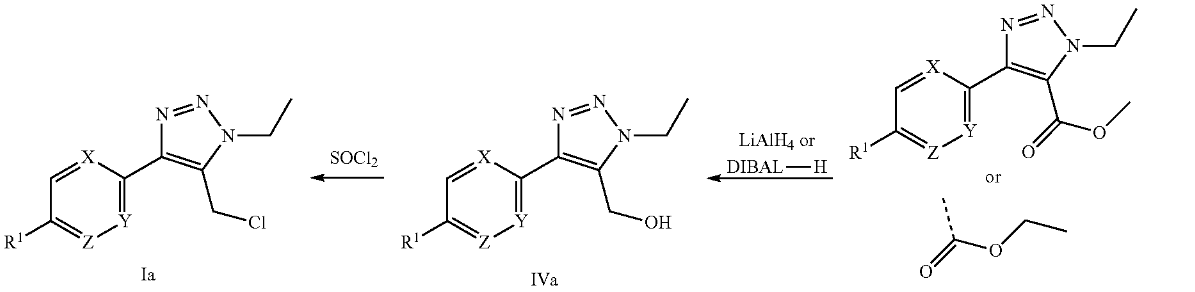

Ia IVa VIII

In certain embodiments of the invention where $R^2$ is ethyl, a slightly modified synthetic route to access alkyl chlorides Ia and alcohols IVa is used by replacing trimethylsilylmethyl azide with ethyl azide (see Scheme 4).

Scheme 5: alternative synthesis of alkyl chlorides Ia and alcohols IVa; wherein all definitions are as described above and in the claims

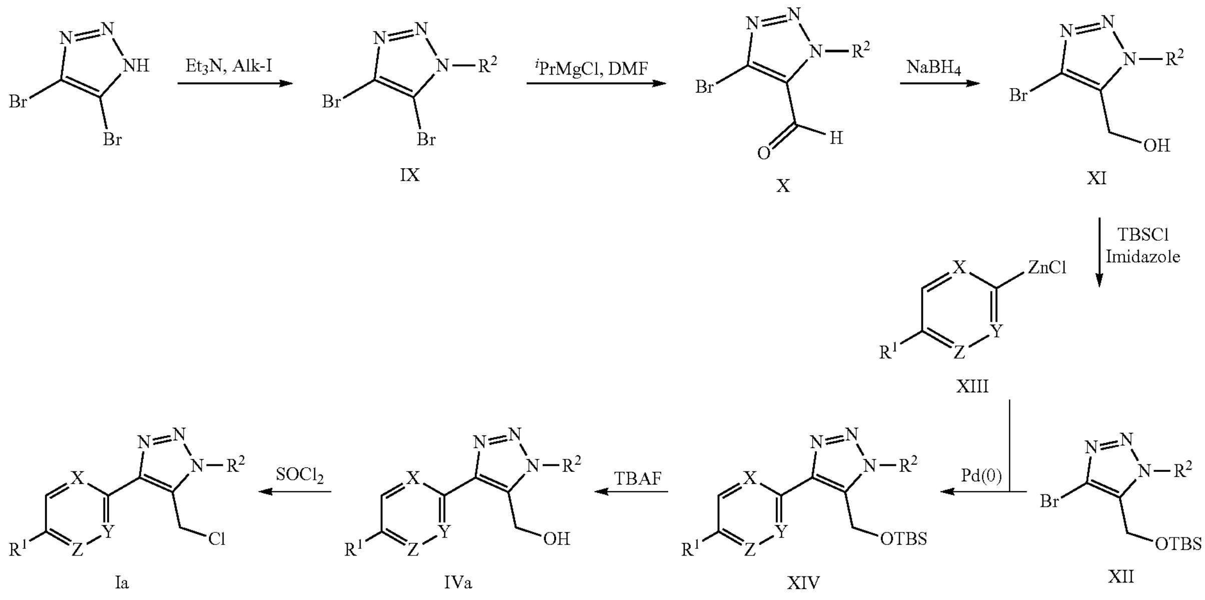

IX X XI XIII XII XIV IVa Ia

In alternative, triazoles Ia can be obtained according to the synthetic route described in Scheme 5. Commercially available 4,5-dibromo-1H-1,2,3-triazole is N-alkylated under standard conditions. Regioselective metalation reaction with isopropylmagnesium chloride in tetrahydrofuran followed by quenching with N,N-dimethylformamide yields aldehydes X. Their reduction to alcohols XI under standard conditions ($NaBH_4$, MeOH) followed by protection of the hydroxyl residue with tert-butyldimethylsilyl chloride yields aryl bromides XII. These can be used in a $sp^2$-$sp^2$ Negishi coupling with an organozinc intermediates XIII formed in situ to access triazoles XIV. Their final conversion to desired alkyl chlorides IIa is accomplished in two-steps by protecting group removal reaction with TBAF, followed up by exposure to thionyl chloride.

Scheme 6: synthesis of alkyl chlorides IIa and alcohols IVb; wherein all definitions are as described above and in the chains

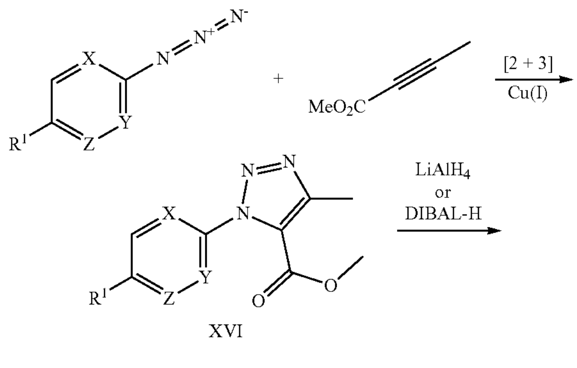

XVI

-continued

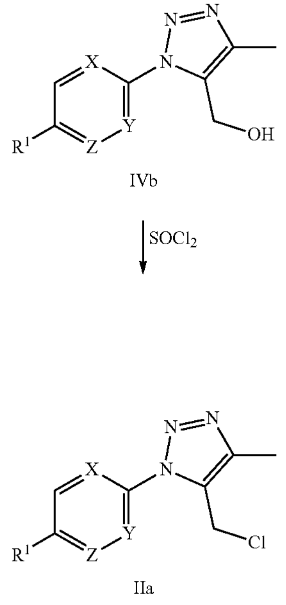

IVb

IIa

Synthesis of regioisomeric triazoles IIa and IVb is illustrated in Scheme 6. Commercially available aryl azides XV undergo a thermal 1,3-dipolar cycloaddition reaction with methyl but-2-ynoate to yield 1,2,3-triazoles XVI. Their reduction to alcohols IVb can be accomplished directly with $LiAlH_4$ or DIBAL-H at controlled temperature. Final conversion to desired alkyl chlorides IIa is accomplished by exposure to thionyl chloride.

Scheme 7: synthesis of aryl halides Ic or IIc

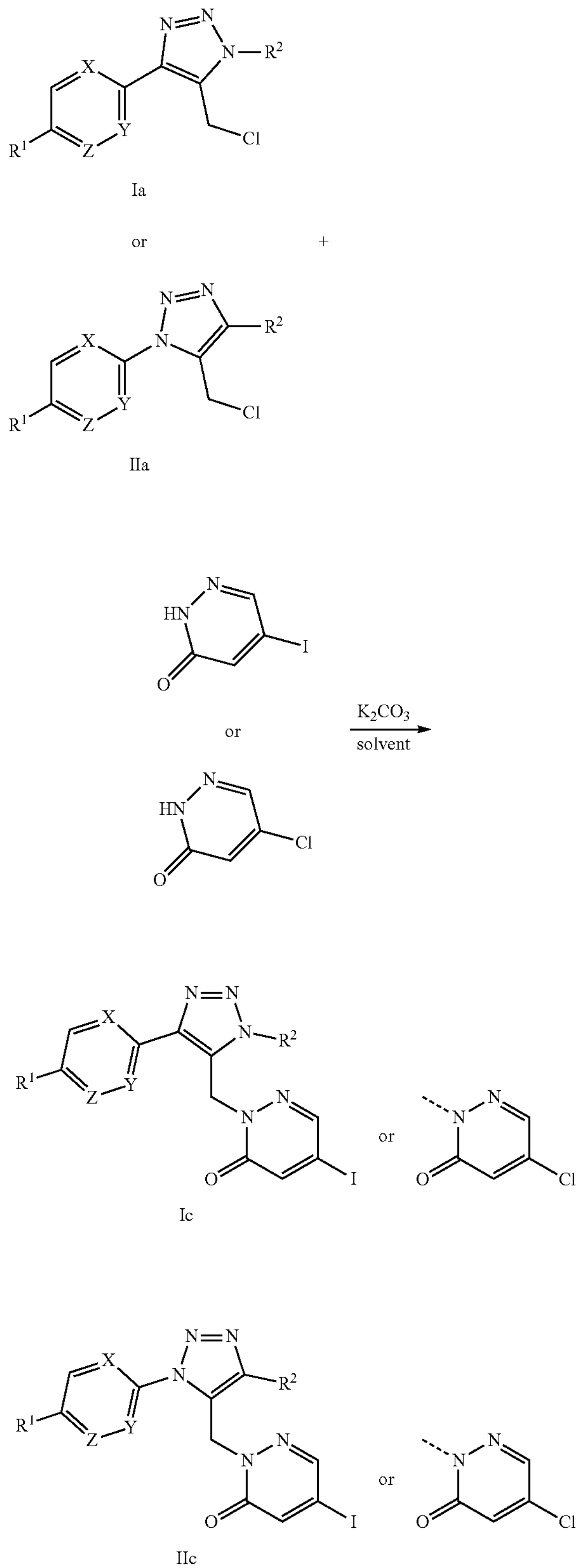

Ia or IIa; Ic; IIc

Conveniently, alkyl chlorides Ia or IIa can be reacted in presence of a base ($K_2CO_3$ or $Cs_2CO_3$) with commercially available 4-chloro-1H-pyridazin-6-one or 4-iodo-1H-pyridazin-6-one to provide bench stable 5-chloro or 5-iodo pyridazinones Ic and IIc as shown in Scheme 7.

Scheme 8: synthesis of pyridazinones Id or IId from aryl halides Ic or IIc; wherein $R^3$ is amino substituted on the nitrogen atom by one or two substituents or substituted heterocycloalkyl; all other definitions are as described above and in the claims

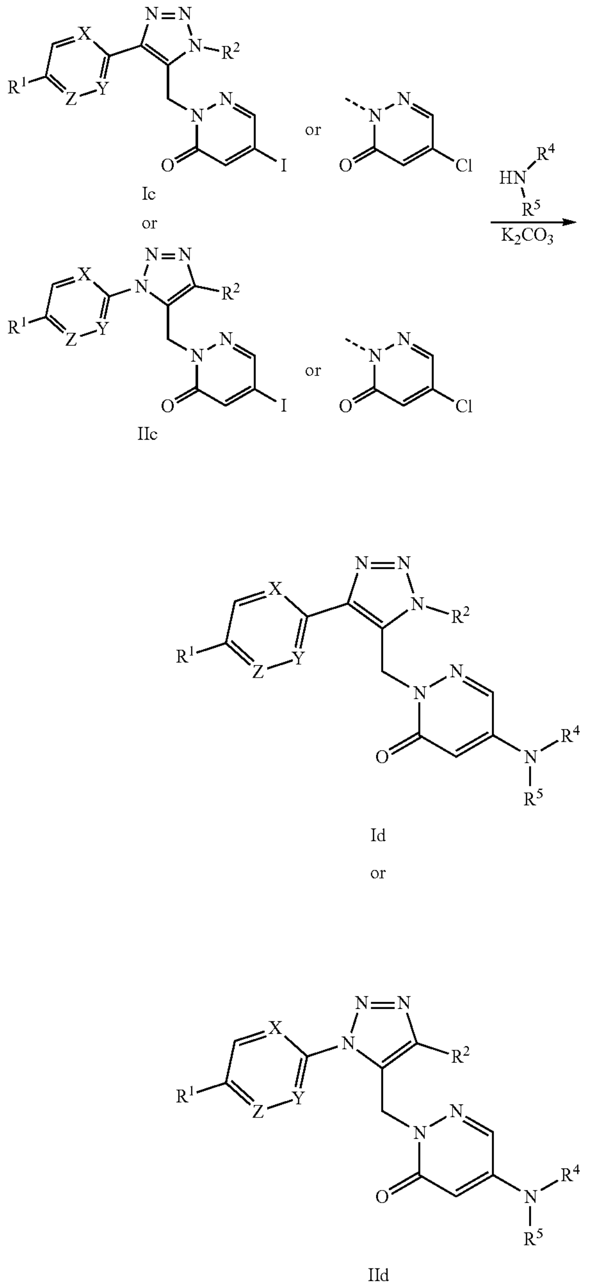

Ic or IIc; Id or IId

In certain embodiments of the invention where $R^3$ is nitrogen, pyridazinones of formula (I) or (II) can be prepared by nucleophilic aromatic substitution reaction between aryl halides Ic or IIc and a primary ($R^4$=H) or a secondary amine $HNR^4R^5$, including a large variety of heterocycloalkyl amines (Scheme 8).

Scheme 9: synthesis of pyridazinones Ie or IIe from aryl chlorides Ic or IIc; wherein $R^3$ is aryl or heteroaryl; all other definitions are as described above and in the claims

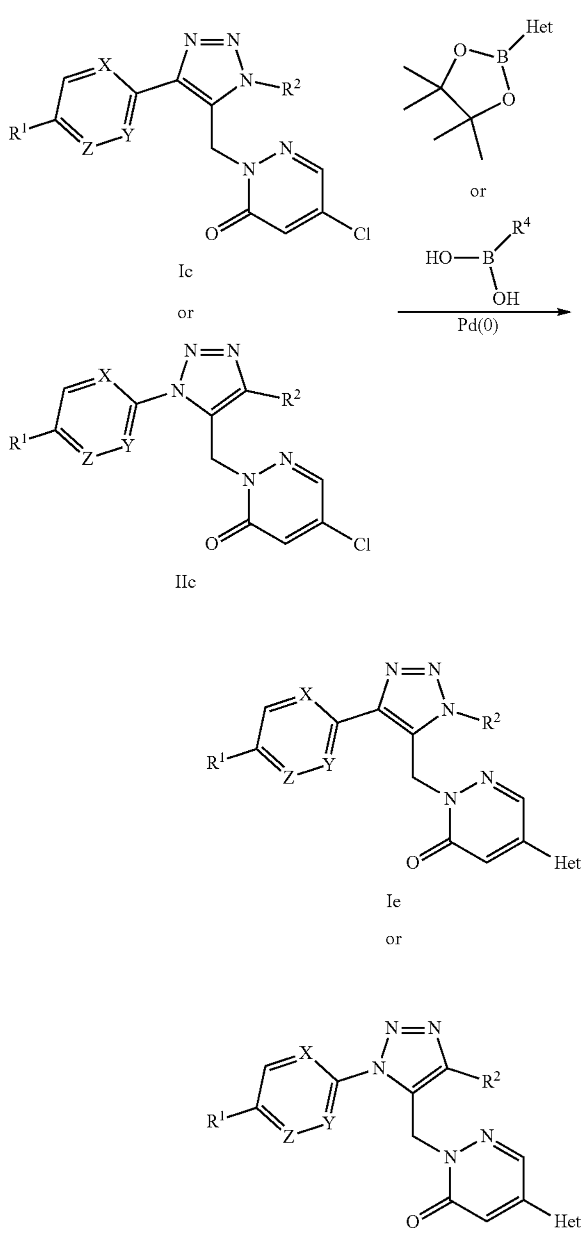

In further embodiments of the invention, where $R^3$ is heteroaryl or aryl, pyridazinones of formula (I) or (II) can be obtained by a palladium-mediated Suzuki coupling reaction between aryl chlorides Ic or IIc and commercially available boronic acids or boronates (Scheme 9).

Also an embodiment of the present invention is a process to prepare a compound of formula (I) or (II) as defined above comprising the reaction of a compound of formula (III) with respectively a compound of formula (Ia1) or (IIa1), respectively in a presence of a base, particularly $K_2CO_3$, when W is halogen, such as Cl, or when W is hydroxy, in the presence of dialkyl azodicarboxylate, such as diethyl azodicarboxylate, and triphenylphospine.

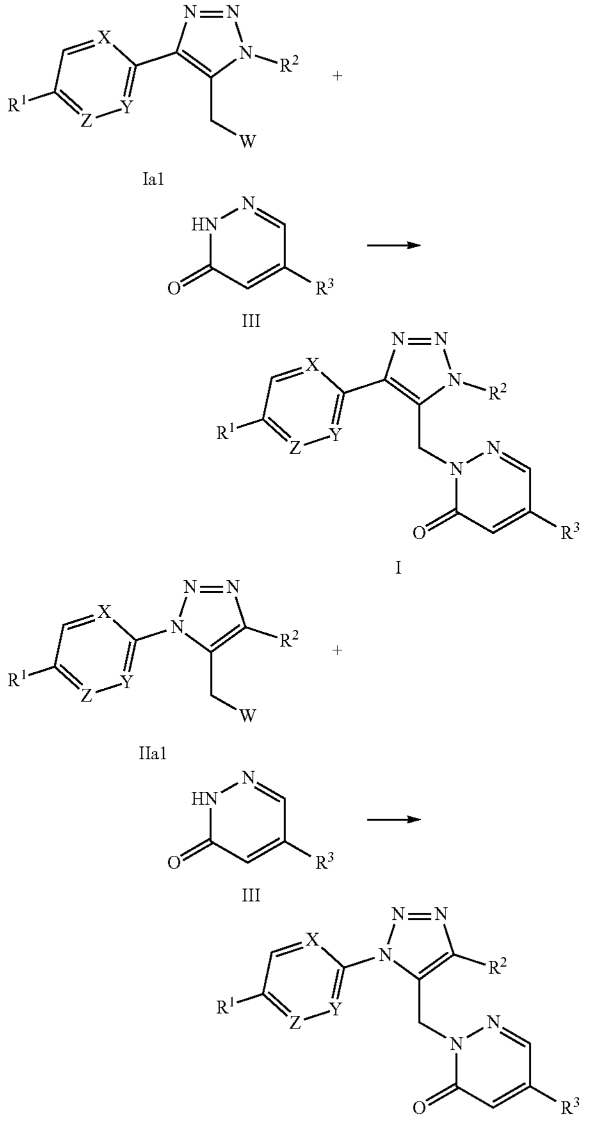

wherein $R^1$, $R^2$, $R^3$, X, Y and Z are as defined herein and W is an halogen or hydroxy.

Also an object of the present invention is a compound according to formula (I) or (II), more particularly compounds of formula (I), as described herein for use as a therapeutically active substance.

Likewise an object of the present invention is a pharmaceutical composition comprising a compound according to formula (I) or (II), more particularly compounds of formula (I), as described herein and a therapeutically inert carrier.

A particular embodiment of the present invention is a compound according to formula (I) or (II), more particularly compounds of formula (I), as described herein for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD).

The present invention also relates to the use of a compound according to formula (I) or (II), more particularly compounds of formula (I), as described herein for the preparation of a medicament for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD).

Also an object of the invention is a method for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD), which method comprises administering an effective amount of a compound according to formula (I) or (II), more particularly compounds of formula (I), as described herein.

Also an embodiment of the present invention are compounds of formula (I) or (II), more particularly compounds of formula (I), as described herein, when manufactured according to any one of the described processes.

Assay Procedures

Membrane Preparation and Binding Assay

The affinity of compounds at $GABA_A$ receptor subtypes was measured by competition for [3H]flumazenil (85 Ci/mmol; Roche) binding to HEK293 cells expressing rat (stably transfected) or human (transiently transfected) receptors of composition $\alpha1\beta3\gamma2$, $\alpha2\beta3\gamma2$, $\alpha3\beta3\gamma2$ and $\alpha5\beta3\gamma2$.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, $[^3H]$-Flumazenil at a concentration of 1 nM for α1, α2, α3 subunits and 0.5 nM for α5 subunits and the test compound in the range of $10\text{-}10^{-3}\times10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. $K_i$ values were calculated using Excel-Fit (Microsoft) and are the means of two determinations.

The compounds of the accompanying examples were tested in the above described assay, and the preferred compounds were found to possess a $K_i$ value for displacement of $[^3H]$-Flumazenil from α5 subunits of the human $GABA_A$ receptor of 100 nM or less. Most preferred are compounds with a $K_i$ (nM) <35. In a preferred embodiment the compounds of the invention are binding selective for the α5 subunit relative to the α1, α2 and α3 subunit. Representative test results, obtained by the above described assay measuring binding affinity to HEK293 cells expressing human (h) receptors, are shown in the Table below.

Functional Expression of $GABA_A$ Receptors:

*Xenopus* Oocytes Preparation

*Xenopus laevis* oocytes at maturation stages V-VI were used for the expression of cloned mRNA encoding $GABA_A$ receptor subunits. Oocytes ready for RNA micro-injection were bought from Ecocyte, Castrop-Rauxel, Germany and stored in modified Barth's medium (composition in mM: NaCl 88, KCl 1, $NaHCO_3$ 2.4, HEPES 10, $MgSO_4$ 0.82, $CaNO_3$ 0.33, $CaCl_2$ 0.33, pH=7.5) at 20° C. until the experiment.

*Xenopus* Oocytes Microinjection

Oocytes were plated in 96-well plates to be used in an automated instrument (Robo-ocyte, MultiChannelSystems, Reutlingen, Germany) for microinjection and electrophysiological recordings. Approximately 50 nl of an aqueous solution containing the RNA transcripts for the subunits of the desired $GABA_A$ receptor was injected into each oocyte. RNA concentrations ranged between 0.3 and 16 ng/μl/subunit and were adjusted in pilot experiments to obtain GABA responses of a suitable size and a maximal effect of the reference modulator, Beta-CCM (3-CCM), a betacarboline negative allosteric modulator (NAM) at the $GABA_A$ receptor benzodiazepine (BZD) binding site or Midazolam, a benzodiazepine positive allosteric modulator (PAM) at the $GABA_A$ receptor benzodiazepine (BZD) binding site. The concentration of the γ2 subunit encoding RNA usually was 5- to 10-fold higher than the RNAs encoding the other subunits. Oocytes were kept in modified Barth's medium (composition in mM: NaCl 88, KCl 1, $NaHCO_3$ 4, HEPES 10, $MgSO_4$ 0.82, $CaNO_3$ 0.33, $CaCl_2$ 0.33, pH=7.5) at 20° C. until the experiment.

Electrophysiology

Electrophysiological experiments were performed on days 3 to 5 after the micro-injection of mRNA. During the experiment the oocytes were constantly superfused by a solution containing (in mM) NaCl 90, KCl 1, HEPES 5, $MgCl_2$ 1, $CaCl_2$ 1 (pH 7.4). Oocytes were impaled by two glass microelectrodes (resistance: 0.4 MQ) which were filled with a solution containing KCl 1M+K-acetate 1.5 M and voltage-clamped to −80 mV. The recordings were performed at room temperature using the Roboocyte two-electrode voltage clamp system (Multichannelsystem). After an initial equilibration period of 1.5 min GABA was added for 1.5 min at a concentration evoking approximately 20% of a maximal current response ($EC_{20}$). After another rest interval of 2.5 min GABA was again added evoking a response of similar amplitude and shape. 0.5 min after the onset of this second GABA application the test compound, at a concentration corresponding to approximatively 30 fold its Ki, was added while GABA was still present. Current traces were recorded at a digitization rate of 10 Hz during and shortly before and after the GABA application.

Each compound and concentration was tested on at least 3 oocytes. Different oocytes were used for different compound concentrations. β-CCM, a negative allosteric modulator, or Midazolam, a positive allosteric modulators, were tested on a few (3-6) oocytes on each 96-well plate for a positive control at a maximally effective. β-CCM inhibited the GABA-evoked current by approximatively 50% (Fold increase 0.5), while Midazolam potentiated the GABA-induced current by approximatively 150% (Fold increase 2.5).

Data Analysis

For the analysis, the digitized current traces of the first and second GABA response were superimposed and, if necessary, rescaled to equal maximal amplitudes. The ratio between the two responses during the time interval of test compound application was calculated point by point. The extremum of the resulting "ratio trace" was taken as the efficacy ("Fold increase") of the compound expressed as "% modulation of GABA $EC_{20}$" (100*(Fold increase-1)). The results are shown in Table 1.

TABLE 1

| Example | Ki h-GABA-A α5β3γ2 (μM) | Fold increase h-GABA-A α5β3γ2 oocyte | Efficacy (GABA) % |
|---|---|---|---|
| 1 | 0.0344 | 2.9 | 190 |
| 2 | 0.0047 | 3.3 | 230 |
| 3 | 0.0012 | 2.24 | 124 |
| 4 | 0.0156 | 1.97 | 97 |
| 5 | 0.0184 | 1.58 | 58 |
| 6 | 0.0718 | 2.21 | 121 |
| 7 | 0.0058 | 2.64 | 164 |
| 8 | 0.0209 | 2.3 | 130 |
| 9 | 0.0168 | 2.35 | 135 |
| 10 | 0.0044 | 3.01 | 201 |
| 11 | 0.0012 | 1.48 | 48 |
| 12 | 0.0026 | 2.91 | 191 |
| 13 | 0.0319 | 1.31 | 31 |
| 14 | 0.0396 | 1.72 | 72 |
| 15 | 0.0038 | 1.48 | 48 |
| 16 | 0.0022 | 1.81 | 81 |
| 17 | 0.012 | 1.75 | 75 |
| 18 | 0.0008 | 1.79 | 79 |
| 19 | 0.0106 | 2.37 | 137 |
| 20 | 0.0084 | 2.08 | 108 |
| 21 | 0.0087 | 2.4 | 140 |
| 22 | 0.0208 | 1.45 | 45 |
| 23 | 0.07 | 1.75 | 75 |
| 24 | 0.0526 | 1.6 | 60 |
| 25 | 0.0044 | 1.97 | 97 |
| 26 | 0.0128 | 1.55 | 55 |
| 27 | 0.0082 | 1.69 | 69 |
| 28 | 0.0184 | 2.15 | 115 |
| 29 | 0.0152 | 1.49 | 49 |
| 30 | 0.0031 | 2.1 | 110 |
| 31 | 0.0172 | 1.35 | 35 |
| 32 | 0.0464 | 1.98 | 98 |
| 33 | 0.0167 | 1.61 | 61 |
| 34 | 0.0442 | 1.85 | 85 |
| 35 | 0.0104 | 2.3 | 130 |
| 36 | 0.0124 | 2.06 | 106 |
| 37 | 0.0036 | 2.35 | 135 |
| 38 | 0.0056 | 1.78 | 78 |
| 39 | 0.0115 | 2.08 | 108 |
| 40 | 0.0202 | 2.03 | 103 |
| 41 | 0.0377 | 1.47 | 47 |
| 42 | 0.0183 | 1.71 | 71 |
| 43 | 0.0079 | 1.97 | 97 |
| 44 | 0.0044 | 1.82 | 82 |
| 45 | 0.0014 | 2.15 | 115 |
| 46 | 0.0016 | 1.86 | 86 |
| 47 | 0.0132 | 2.3 | 130 |
| 48 | 0.0085 | 1.52 | 52 |
| 49 | 0.0083 | 1.73 | 73 |

TABLE 1-continued

| Example | Ki h-GABA-A α5β3γ2 (μM) | Fold increase h-GABA-A α5β3γ2 oocyte | Efficacy (GABA) % |
|---|---|---|---|
| 50 | 0.0052 | 1.67 | 67 |
| 51 | 0.0214 | 1.94 | 94 |
| 52 | 0.0041 | 1.55 | 55 |
| 53 | 0.0054 | 1.69 | 69 |
| 54 | 0.0064 | 1.82 | 82 |
| 55 | 0.0058 | 2.11 | 111 |
| 56 | 0.0216 | 1.5 | 50 |
| 57 | 0.043 | 1.64 | 64 |
| 58 | 0.007 | 2.38 | 138 |
| 59 | 0.0371 | 1.81 | 81 |
| 60 | 0.045 | 1.76 | 76 |
| 61 | 0.0026 | 1.52 | 52 |
| 62 | 0.0082 | 1.5 | 50 |
| 63 | 0.0022 | 1.42 | 42 |
| 64 | 0.0112 | 1.76 | 76 |
| 65 | 0.0475 | 1.42 | 42 |
| 66 | 0.019 | 2.43 | 143 |
| 67 | 0.011 | 1.55 | 55 |
| 68 | 0.0322 | 2.3 | 130 |
| 69 | 0.0043 | 2.25 | 125 |
| 70 | 0.025 | 1.71 | 71 |
| 71 | 0.0122 | 1.75 | 75 |
| 72 | 0.0194 | 1.7 | 70 |
| 73 | 0.0077 | 1.9 | 90 |
| 74 | 0.0118 | 1.86 | 86 |
| 75 | 0.023 | 1.73 | 73 |
| 76 | 0.0116 | 2.15 | 115 |
| 77 | 0.0184 | 1.66 | 66 |
| 78 | 0.0112 | 2.06 | 106 |
| 79 | 0.011 | 1.88 | 88 |
| 80 | 0.0168 | 1.72 | 72 |
| 81 | 0.0199 | 2.1 | 110 |
| 82 | 0.031 | 3.36 | 236 |
| 83 | 0.0147 | 2.08 | 108 |
| 84 | 0.0102 | 1.73 | 73 |
| 85 | 0.0185 | 2.43 | 143 |
| 86 | 0.0108 | 2.36 | 136 |
| 87 | 0.0125 | 2.15 | 115 |
| 88 | 0.007 | 2.26 | 126 |
| 89 | 0.0093 | 1.76 | 76 |
| 90 | 0.0194 | 1.96 | 96 |
| 91 | 0.0182 | 2.28 | 128 |
| 92 | 0.0056 | 2.59 | 159 |
| 93 | 0.0094 | 1.79 | 79 |
| 94 | 0.0104 | 2.27 | 127 |
| 95 | 0.0111 | 1.58 | 58 |
| 96 | 0.0204 | 1.54 | 54 |
| 97 | 0.0451 | 2.15 | 115 |
| 98 | 0.008 | 1.58 | 58 |
| 99 | 0.0046 | 1.86 | 86 |
| 100 | 0.0159 | 1.79 | 79 |
| 101 | 0.0092 | 2.26 | 126 |
| 102 | 0.0202 | 2.64 | 164 |
| 103 | 0.0104 | 2.06 | 106 |
| 104 | 0.0118 | 2.58 | 158 |
| 105 | 0.0172 | 2.11 | 111 |
| 106 | 0.0114 | 1.72 | 72 |
| 107 | 0.009 | 3.34 | 234 |
| 108 | 0.0168 | 1.46 | 46 |
| 109 | 0.0011 | 1.75 | 75 |
| 110 | 0.0088 | 2.39 | 139 |
| 111 | 0.0238 | 3.9 | 290 |
| 112 | 0.0128 | 3.28 | 228 |
| 113 | 0.0485 | 1.98 | 98 |
| 114 | 0.0036 | 2.54 | 154 |
| 115 | 0.0474 | 1.74 | 74 |
| 116 | 0.0661 | 1.48 | 48 |
| 117 | 0.0527 | 1.87 | 87 |
| 118 | 0.0154 | 2.35 | 135 |
| 119 | 0.0296 | 1.86 | 86 |
| 120 | 0.027 | 1.78 | 78 |
| 121 | 0.0248 | 1.89 | 89 |
| 122 | 0.0555 | 2.41 | 141 |
| 123 | 0.0076 | 2.48 | 148 |
| 124 | 0.0102 | 2.05 | 105 |

TABLE 1-continued

| Example | Ki h-GABA-A α5β3γ2 (μM) | Fold increase h-GABA-A α5β3γ2 oocyte | Efficacy (GABA) % |
|---|---|---|---|
| 125 | 0.0253 | 1.69 | 69 |
| 126 | 0.0175 | 1.61 | 61 |

WO2014/001280 discloses reference compound RO-07 as example 1.

WO2012/062687 discloses reference compounds RO-052 as example 52, RO-045 as example 45.

The reference compounds were also tested for their affinity towards the $GABA_A$ receptor α5β3γ2 subtypes as well as for their efficacy in $GABA_A$ α5β3γ2 overexpressing oocytes. The results are shown in Table 2.

TABLE 2

| Example | Ki h-GABA-A α5β3γ2 (μM) | Fold increase h-GABA-A α5β3γ2 oocyte | Efficacy (GABA) % |
|---|---|---|---|
| RO-007 | 0.0584 | 0.72 | −28 |
| RO-052 | 0.0334 | 0.85 | −15 |
| RO-045 | 0.0532 | 0.62 | −38 |

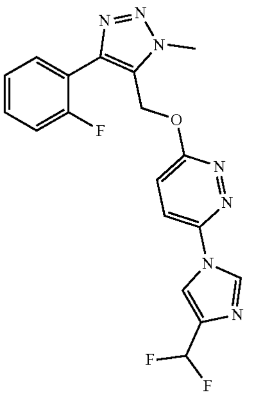

RO-007

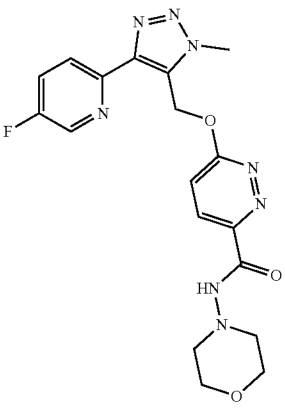

RO-052

TABLE 2-continued

| Example | Ki h-GABA-A α5β3γ2 (μM) | Fold increase h-GABA-A α5β3γ2 oocyte | Efficacy (GABA) % |
|---|---|---|---|

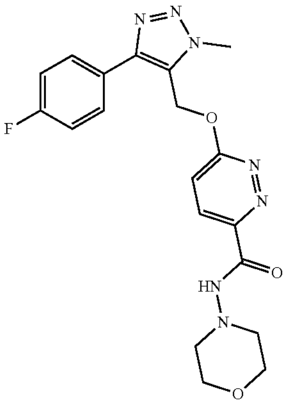

RO-045

The compounds of formula (I) or (II) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) or (II) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Preparation of Pharmaceutical Compositions Comprising Compounds of the Invention Tablets of the following composition are manufactured in the usual manner:

| | mg/tablet | | | |
|---|---|---|---|---|
| Ingredient | 5 | 25 | 100 | 500 |
| Compound of formula 1 | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the Following Composition are Manufactured:

| | mg/capsule | | | |
|---|---|---|---|---|
| Ingredient | 5 | 25 | 100 | 500 |
| Compound of formula 1 | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoapproximatively. The mixture is filled by machine into suitable capsules, e.g. hard gelatin capsules.

Injection solutions of the following composition are manufactured:

| Ingredient | mg/injection solution. |
|---|---|
| Compound of formula 1 | 3 |
| Polyethylene Glycol 400 | 150 |
| acetic acid | q.s. ad pH 5.0 |
| water for injection solutions | ad 1.0 ml |

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

Building Block A

[5-(4-fluorophenyl)-3-methyl-triazol-4-yl]methanol

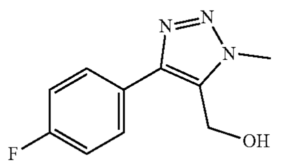

Described in US 20120115844, US 20120115868

Building Block B

[3-(4-fluorophenyl)-5-methyl-triazol-4-yl]methanol

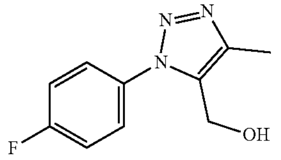

Described in US 20120115868, US 20120115844

Building Block C

[5-methyl-3-(6-methyl-3-pyridyl)triazol-4-yl]methanol

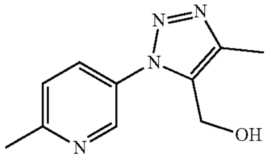

a) ethyl 5-methyl-3-(6-methyl-3-pyridyl)triazole-4-carboxylate

To a solution of 5-azido-2-methyl-pyridine (25.0 g, 186 mmol) in toluene (100 mL) was added ethyl but-2-ynoate (23 mL, 205 mmol) in a sealed tube and reaction mixture was heated to 150° C. for 16 h. The solvent was evaporated by rotatory evaporation and the residue was purified by flash chromatography (silica, 100% ethyl acetate) to afford the title compound (10 g, 60%) as a yellow solid. MS (ESI): 246.8 ([M+H]$^+$).

b) [5-methyl-3-(6-methyl-3-pyridyl)triazol-4-yl]methanol

To a solution of ethyl 5-methyl-3-(6-methyl-3-pyridyl)triazole-4-carboxylate (3.00 g, 12.2 mmol) in tetrahydrofuran (13 mL) was added dropwise at 10° C. a solution of $LiAlH_4$ in tetrahydrofuran (1.0 M, 13 mL, 13 mmol) and the reaction mixture was stirred at 10° C. for 15 min. The reaction mixture was then cooled to 0° C. before being quenched by the addition of sodium sulfate decahydrate. The resulting suspension was filtered through a pad of celite and the filtrate concentrated in vacuo. Purification by flash chromatography (silica, 100% ethyl acetate) afforded the title compound (1.5 g, 60%) as a white solid. MS (ESI): 205.2 ([M+H]$^+$).

Building Block D

[5-methyl-3-(6-methyl-3-pyridyl)triazol-4-yl]methanol

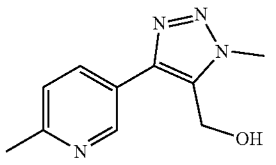

a) trimethyl-[[4-(6-methyl-3-pyridyl)triazol-1-yl]methyl]silane

To a solution of 5-ethynyl-2-methyl-pyridine (10.0 g, 85.5 mmol) in DMF (100 mL) was added at room temperature DIPEA (15.2 mL, 85.5 mmol) and CuI (11 g, 85.5 mmol). After 5 min, trimethylsilylmethyl azide (55.5 g, 427 mmol) was added and the reaction mixture was stirred for 16 h. The reaction mixture was poured into water and the aqueous layer was extracted with ethyl acetate (3×200 mL). The organic layer was washed with brine, dried ($Na_2SO_4$) and concentrated in vacuo. Purification by flash chromatography (silica, 60% ethyl acetate in hexane) afforded the title compound (15 g, 73%) as a white solid. MS (ESI): 246.0 ([M+H]$^+$).

b) 2-methyl-5-(1-methyltriazol-4-yl)pyridine

To a solution of trimethyl-[[4-(6-methyl-3-pyridyl)triazol-1-yl]methyl]silane (10.0 g, 40.6 mmol) in tetrahydrofuran (50 mL) was added a solution of TBAF in tetrahydrofuran (1.0 M, 61 mL, 61 mmol). The reaction mixture was stirred at room temperature for 1 h. Purification by flash chromatography (silica, 100% ethyl acetate) afforded the title compound (6.0 g, 87%) as an off-white solid. MS (ESI): 175.3 ([M+H]$^+$).

c) methyl 3-methyl-5-(6-methyl-3-pyridyl)triazole-4-carboxylate

To a stirred solution of 2-methyl-5-(1-methyltriazol-4-yl)pyridine (6.0 g, 34 mmol) in anhydrous tetrahydrofuran (100 mL) at −78° C. under an argon atmosphere was added dropwise a solution of LDA in tetrahydrofuran (2.0 M, 35 mL, 70 mmol). After 30 min, methyl chloroformate (8.60 mL, 103 mmol) was added and the reaction mixture was stirred at −78° C. After 1.5 h, the reaction mixture was quenched by addition of an ice cold saturated aqueous $NH_4Cl$ solution. The resulting mixture was extracted with ethyl acetate (2×250 mL). The organic layer was washed with brine, dried ($Na_2SO_4$) and concentrated in vacuo. Purification by flash chromatography (silica, 65% ethyl acetate in hexane) afforded the title compound (4 g, 50%) as a yellow solid. MS (ESI): 232.7 ([M+H]$^+$).

d) [3-methyl-5-(6-methyl-3-pyridyl)triazol-4-yl]methanol

In analogy to experiment of example C b, methyl 3-methyl-5-(6-methyl-3-pyridyl)triazole-4-carboxylate instead of ethyl 5-methyl-3-(6-methyl-3-pyridyl)triazole-4-carboxylate was converted into the title compound (2.4 g, 67%) which was obtained as an off-white solid. MS (ESI): 205.3 ([M+H]$^+$).

Building Block E

[5-(4-chloro-2-fluoro-phenyl)-3-methyl-triazol-4-yl]methanol

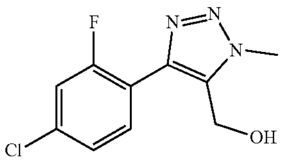 [SMILES: Cn1nnc(-c2ccc(Cl)cc2F)c1CO]

a) [4-(4-chloro-2-fluoro-phenyl)triazol-1-yl]methyl-trimethyl-silane

In analogy to experiment of example D a, 4-chloro-1-ethynyl-2-fluoro-benzene instead of 5-ethynyl-2-methyl-pyridine was converted into the title compound (7.85 g, 85%) which was obtained as an off-white solid. MS (ESI): 283.7 ([M+H]$^+$).

b) 4-(4-chloro-2-fluoro-phenyl)-1-methyl-triazole

In analogy to experiment of example D b, [4-(4-chloro-2-fluoro-phenyl)triazol-1-yl]methyl-trimethyl-silane instead of trimethyl-[[4-(6-methyl-3-pyridyl)triazol-1-yl]methyl]silane was converted into the title compound (4.7 g, 80%) which was obtained as a white solid. MS (ESI): 211.9 ([M+H]$^+$).

c) methyl 5-(4-chloro-2-fluoro-phenyl)-3-methyl-triazole-4-carboxylate

In analogy to experiment of example D c, 4-(4-chloro-2-fluoro-phenyl)-1-methyl-triazole instead of 2-methyl-5-(1-methyltriazol-4-yl)pyridine was converted into the title compound (4.75 g, 71%) which was obtained as a colorless sticky solid. MS (ESI): 283.9 ([M+H]$^+$).

d) [5-(4-chloro-2-fluoro-phenyl)-3-methyl-triazol-4-yl]methanol

In analogy to experiment of example C b, methyl 5-(4-chloro-2-fluoro-phenyl)-3-methyl-triazole-4-carboxylate instead of ethyl 5-methyl-3-(6-methyl-3-pyridyl)triazole-4-carboxylate was converted into the title compound (2.4 g, 67%) which was obtained as an off-white solid. MS (ESI): 205.3 ([M+H]$^+$).

Building Block F

[3-(4-chloro-2-fluoro-phenyl)-5-methyl-triazol-4-yl]methanol

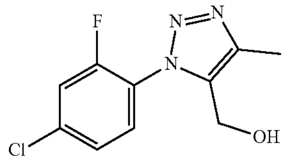 [SMILES: Cc1nnn(-c2ccc(Cl)cc2F)c1CO]

a) methyl 3-(4-chloro-2-fluoro-phenyl)-5-methyl-triazole-4-carboxylate

To a solution of 1-azido-4-chloro-2-fluoro-benzene (20.0 g, 117 mmol) in toluene (15 mL) was added methyl but-2-ynoate (14.0 mL, 117 mmol). The reaction mixture was heated to 120° C. in a sealed tube. After 15 h, the mixture was allowed to cool to room temperature then all volatiles were evaporated under reduced pressure to obtain a crude residue. Purification by flash chromatography (silica, 30% ethyl acetate in hexane) afforded the title compound (7.6 g, 26%) as a brown liquid. MS (ESI): 283.8 ([M+H]$^+$).

b) [3-(4-chloro-2-fluoro-phenyl)-5-methyl-triazol-4-yl]methanol

To a solution of methyl 3-(4-chloro-2-fluoro-phenyl)-5-methyl-triazole-4-carboxylate (5.70 g, 20.1 mmol) in tetrahydrofuran (300 mL) at 0° C., was added a solution of DIBAL-H in toluene (1.8 M, 28 mL, 50.4 mmol). After 1 h, the reaction mixture was carefully quenched at 0° C. by addition of aqueous potassium sodium tartrate tetrahydrate (10 wt. %, 100 mL). The mixture was extracted with ethyl acetate. The organic phase was washed with brine, dried ($Na_2SO_4$), filtered and concentrated in vacuo. Purification by flash chromatography (silica, 60% ethyl acetate in hexane) afforded the title compound (4.4 g, 90%) as an off-white solid. MS (ESI): 242.1 ([M+H]$^+$).

Building Block G

[3-(4-chlorophenyl)-5-methyl-triazol-4-yl]methanol

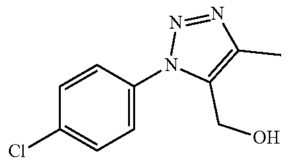

a) methyl 3-(4-chlorophenyl)-5-methyl-triazole-4-carboxylate

In analogy to experiment of example F a, 1-azido-4-chloro-benzene instead of 1-azido-4-chloro-2-fluoro-benzene was converted into the title compound (5.0 g, 25%) which was obtained as a light brown solid. MS (ESI): 266.2 ([M+H]$^+$).

b) [3-(4-chlorophenyl)-5-methyl-triazol-4-yl]methanol

To a solution of methyl 3-(4-chlorophenyl)-5-methyl-triazole-4-carboxylate (2.00 g, 8.20 mmol) in tetrahydrofuran (20 mL) was added dropwise at 0° C. a solution of $LiAlH_4$ in tetrahydrofuran (1.0 M, 9.1 mL, 9.1 mmol). After 30 min, the reaction mixture was quenched by the careful addition of sodium sulfate decahydrate. The mixture was diluted with ethyl acetate (250 mL) then filtered directly on a sintered funnel. The inorganic salts were rinsed with ethyl acetate and the filtrate was concentrated under reduced pressure. Purification by flash chromatography (silica, 60% ethyl acetate in hexane) afforded the title compound (800 mg, 44%) as a brown solid. MS (ESI): 224 ([M+H]$^+$).

Building Block H

[5-(4-chlorophenyl)-3-methyl-triazol-4-yl]methanol

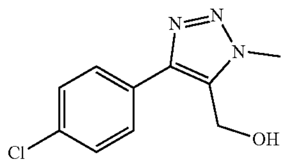

a) [4-(4-chlorophenyl)triazol-1-yl]methyl-trimethyl-silane

In analogy to experiment of example D a, 1-chloro-4-ethynyl-benzene instead of 5-ethynyl-2-methyl-pyridine was converted into the title compound (14 g, 90%) which was obtained as an off-white solid. MS (ESI): 265.8 ([M+H]$^+$).

b) 4-(4-chlorophenyl)-1-methyl-triazole

In analogy to experiment of example D b, [4-(4-chlorophenyl)triazol-1-yl]methyl-trimethyl-silane instead of trimethyl-[[4-(6-methyl-3-pyridyl)triazol-1-yl]methyl]silane was converted into the title compound (4.2 g, 82%) which was obtained as a white solid. MS (ESI): 194.1 ([M+H]$^+$).

c) ethyl 5-(4-chlorophenyl)-3-methyl-triazole-4-carboxylate

In analogy to experiment of example D c, 4-(4-chlorophenyl)-1-methyl-triazole instead of 2-methyl-5-(1-methyltriazol-4-yl)pyridine, using ethyl chloroformate instead of methyl chloroformate was converted into the title compound (4.1 g, 86%) which was obtained as a colorless sticky solid. MS (ESI): 252 ([M+H]$^+$).

d) [5-(4-chlorophenyl)-3-methyl-triazol-4-yl]methanol

In analogy to experiment of example C b, ethyl 5-(4-chlorophenyl)-3-methyl-triazole-4-carboxylate instead of ethyl 5-methyl-3-(6-methyl-3-pyridyl)triazole-4-carboxylate was converted into the title compound (3.0 g, 84%) which was obtained as a white solid. MS (ESI): 224 ([M+H]$^+$).

Building Block I

[5-(2,4-difluorophenyl)-3-methyl-triazol-4-yl]methanol

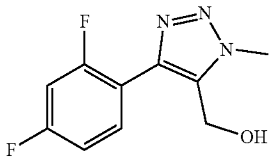 [SMILES: Cn1nnc(-c2ccc(F)cc2F)c1CO]

a) [4-(2,4-difluorophenyl)triazol-1-yl]methyl-trimethyl-silane

In analogy to experiment of example D a, 1-ethynyl-2,4-difluoro-benzene instead of 5-ethynyl-2-methyl-pyridine was converted into the title compound (520 mg, 54%) which was obtained as an off-white solid. MS (ESI): 267.6 ([M+H]$^+$).

b) 4-(2,4-difluorophenyl)-1-methyl-triazole

In analogy to experiment of example D b, [4-(2,4-difluorophenyl)triazol-1-yl]methyl-trimethyl-silane instead of trimethyl-[[4-(6-methyl-3-pyridyl)triazol-1-yl]methyl]silane was converted into the title compound (3.2 g, 94%) which was obtained as a white solid. MS (ESI): 196.0 ([M+H]$^+$.

c) methyl 5-(2,4-difluorophenyl)-3-methyl-triazole-4-carboxylate

To a solution of 4-(2,4-difluorophenyl)-1-methyl-triazole (2.25 g, 11.5 mmol) in tetrahydrofuran (70 mL) was added dropwise at 0° C. a solution of LiHMDS in tetrahydrofuran (1.0 M, 17.3 mL, 17.3 mmol). After 30 min, methyl chloroformate (1.92 mL, 23 mmol) was added and the reaction mixture was stirred at 0° C. The reaction mixture was allowed to warm to room temperature for 1.5 h before being quenched by addition of ice cold saturated aqueous $NH_4Cl$. The mixture was extracted with ethyl acetate (2×250 mL) and the organic layer was washed with brine, dried ($Na_2SO_4$), filtered and concentrated in vacuo. Purification by flash chromatography (silica, 60% ethyl acetate in hexane) afforded the title compound (2.4 g, 82%) as a white solid. MS (ESI): 254 ([M+H]$^+$).

d) [5-(2,4-difluorophenyl)-3-methyl-triazol-4-yl] methanol

In analogy to experiment of example G b, methyl 5-(2,4-difluorophenyl)-3-methyl-triazole-4-carboxylate instead of methyl 3-(4-chlorophenyl)-5-methyl-triazole-4-carboxylate was converted into the title compound (3.0 g, 96%) which was obtained as a white solid. MS (ESI): 225.9 ([M+H]$^+$).

Building Block J

[5-[2-fluoro-4-(trifluoromethyl)phenyl]-3-methyl-triazol-4-yl]methanol

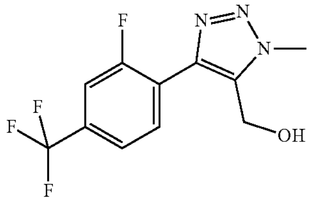 [SMILES: Cn1nnc(-c2ccc(C(F)(F)F)cc2F)c1CO]

a) [4-[2-fluoro-4-(trifluoromethyl)phenyl]triazol-1-yl]methyl-trimethyl-silane

In analogy to experiment of example D a, 1-ethynyl-2-fluoro-4-(trifluoromethyl)benzene instead of 5-ethynyl-2-methyl-pyridine was converted into the title compound (12 g, 60%) which was obtained as an off-white solid. MS (ESI): 317.6 ([M+H]$^+$).

b) 4-[2-fluoro-4-(trifluoromethyl)phenyl]-1-methyl-triazole

In analogy to experiment of example D b, [4-[2-fluoro-4-(trifluoromethyl)phenyl]triazol-1-yl]methyl-trimethyl-silane instead of trimethyl-[[4-(6-methyl-3-pyridyl)triazol-1-yl]methyl]silane was converted into the title compound (6.9 g, 94%) which was obtained as a white solid. MS (ESI): 246 ([M+H]$^+$).

c) methyl 5-[2-fluoro-4-(trifluoromethyl)phenyl]-3-methyl-triazole-4-carboxylate In analogy to experiment of example I c, 4-[2-fluoro-4-(trifluoromethyl)phenyl]-1-methyl-triazole instead of 4-(2,4-difluorophenyl)-1-methyl-triazole was converted into the title compound (7.5 g, 87%) which was obtained as a white solid. MS (ESI): 303.8 ([M+H]$^+$).

d) [5-[2-fluoro-4-(trifluoromethyl)phenyl]-3-methyl-triazol-4-yl]methanol

In analogy to experiment of example G b, methyl 5-[2-fluoro-4-(trifluoromethyl)phenyl]-3-methyl-triazole-4-carboxylate instead of methyl 3-(4-chlorophenyl)-5-methyl-triazole-4-carboxylate was converted into the title compound (5.6 g, 82%) which was obtained as a white solid. MS (ESI): 275.8 ([M+H]$^+$).

Building Block K

[5-(4-chloro-2-fluoro-phenyl)-3-ethyl-triazol-4-yl]methanol

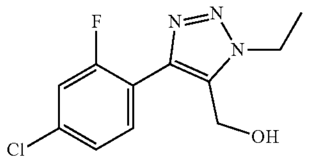 [SMILES: CCn1nnc(-c2ccc(Cl)cc2F)c1CO]

a) 4-(4-chloro-2-fluoro-phenyl)-1-ethyl-triazole

To a solution of 4-chloro-1-ethynyl-2-fluoro-benzene (4.50 g, 29.1 mmol) in DMF (50 mL) was added at room temperature DIPEA (5.2 mL, 29 mmol), CuI (5.5 g, 29 mmol) and ethyl azide (11 g, 146 mmol). The reaction mixture was stirred for 16 h before being quenched by the addition of water. The aqueous layer was extracted with ethyl acetate (3×200 mL). The organic layers were washed with brine, dried ($Na_2SO_4$), filtered and concentrated in vacuo. Purification by flash chromatography (silica, 15% ethyl acetate in hexane) afforded the title compound (5.0 g, 80%) as a white solid. MS (ESI): 226 ([M+H]$^+$).

b) methyl 5-(4-chloro-2-fluoro-phenyl)-3-ethyl-triazole-4-carboxylate

In analogy to experiment of example I c, 4-(4-chloro-2-fluoro-phenyl)-1-ethyl-triazole instead of 4-(2,4-difluorophenyl)-1-methyl-triazole was converted into the title compound (4.1 g, 81%) which was obtained as a colorless sticky solid. MS (ESI): 284.3 ([M+H]$^+$).

c) [5-(4-chloro-2-fluoro-phenyl)-3-ethyl-triazol-4-yl]methanol

In analogy to experiment of example G b, methyl 5-(4-chloro-2-fluoro-phenyl)-3-ethyl-triazole-4-carboxylate instead of methyl 3-(4-chlorophenyl)-5-methyl-triazole-4-carboxylate was converted into the title compound (3.0 g, 83%) which was obtained as a white solid. MS (ESI): 256.1 ([M+H]$^+$).

Building Block L

[5-(6-chloro-3-pyridyl)-3-methyl-triazol-4-yl]methanol

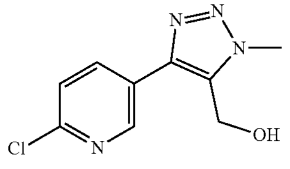

a) [4-(6-chloro-3-pyridyl)triazol-1-yl]methyl-trimethyl-silane

In analogy to experiment of example D a, 2-chloro-5-ethynyl-pyridine instead of 5-ethynyl-2-methyl-pyridine was converted into the title compound (8.5 g, 63%) which was obtained as a white solid. MS (ESI): 266.9 ([M+H]$^+$).

b) 2-chloro-5-(1-methyltriazol-4-yl)pyridine

In analogy to experiment of example D b, [4-(6-chloro-3-pyridyl)triazol-1-yl]methyl-trimethyl-silane instead of trimethyl-[[4-(6-methyl-3-pyridyl)triazol-1-yl]methyl]silane was converted into the title compound (4.5 g, 77%) which was obtained as a white solid. MS (ESI): 195 ([M+H]$^+$).

c) methyl 5-(6-chloro-3-pyridyl)-3-methyl-triazole-4-carboxylate

In analogy to experiment of example I c, 2-chloro-5-(1-methyltriazol-4-yl)pyridine instead of 4-(2,4-difluorophenyl)-1-methyl-triazole was converted into the title compound (4.7 g, 95%) which was obtained as an off-white solid. MS (ESI): 252.6 ([M+H]$^+$).

d) [5-(6-chloro-3-pyridyl)-3-methyl-triazol-4-yl]methanol

In analogy to experiment of example G b, methyl 5-(6-chloro-3-pyridyl)-3-methyl-triazole-4-carboxylate instead of methyl 3-(4-chlorophenyl)-5-methyl-triazole-4-carboxylate was converted into the title compound (3.0 g, 67%) which was obtained as a yellow solid. MS (ESI): 224.9 ([M+H]$^+$).

Building Block M

[3-methyl-5-[5-(trifluoromethyl)pyrimidin-2-yl]triazol-4-yl]methanol

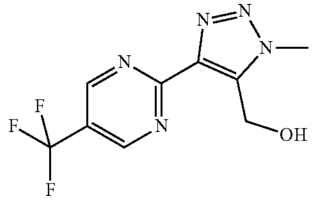 [SMILES: Cn1nnc(-c2ncc(C(F)(F)F)cn2)c1CO]

a) methyl 5-tributylstannyl-3-(trimethylsilylmethyl)triazole-4-carboxylate

To a solution of methyl-3-tributylstannylprop-2-ynoate (13.0 g, 34.8 mmol) in toluene (50 mL) was added trimethylsilylmethyl azide (6.50 g, 50.3 mmol) The reaction mixture was heated to 120° C. and stirred in sealed tube. After 16 h, the reaction mixture was allowed to cool to room temperature and all volatiles were evaporated under reduced pressure to obtain a crude residue. Purification by flash chromatography (silica, 10% ethyl acetate in hexane) afforded the title compound (5.8 g, 30%) as a colorless liquid.

b) methyl 5-[5-(trifluoromethyl)pyrimidin-2-yl]-3-(trimethylsilylmethyl)triazole-4-carboxylate To a degassed solution of 2-chloro-5-(trifluromethyl)pyrimidine (2.0 g, 11 mmol) in 1,4-dioxane (50 mL) were added methyl 5-tributylstannyl-3-(trimethylsilylmethyl)triazole-4-carboxylate (6.0 g, 12 mmol), lithium chloride (1.40 g, 32.9 mmol), copper iodide (42 mg, 0.22 mmol) and tetrakis(triphenylphosphine)palladium(0) (253 mg, 0.220 mmol). The reaction mixture was heated to 100° C. and stirred for 3 h. After cooling to room temperature the mixture was filtered directly through a pad of celite and the filter cake rinsed with ethyl acetate (100 mL). The filtrate was concentrate in vacuo and purified by flash chromatography (silica, 65% ethyl acetate in hexane) to obtain the title compound (2.0 g, 50%) as a yellow solid. MS (ESI): 359.8 ([M+H]$^+$).

c) methyl 3-methyl-5-[5-(trifluoromethyl)pyrimidin-2-yl]triazole-4-carboxylate To a solution of methyl 5-[5-(trifluoromethyl)pyrimidin-2-yl]-3-(trimethylsilylmethyl)triazole-4-carboxylate (1.50 g, 4.17 mmol) in a mixture of dichloromethane (12 mL) and methanol (6 mL) was added $K_2CO_3$ (1.70 g, 12.5 mmol) and the mixture was stirred at room temperature for 1 hour. The reaction mixture was diluted with dichloromethane (50 mL) and water. The organic layer was washed with brine, dried ($Na_2SO_4$), filtered and concentrated in vacuo to afford the title compound (750 mg, 62%) as white solid. MS (ESI): 287.9 ([M+H]$^+$).

d) 3-methyl-5-[5-(trifluoromethyl)pyrimidin-2-yl]triazole-4-carboxylic acid

To an ice cold solution of methyl 3-methyl-5-[5-(trifluoromethyl)pyrimidin-2-yl]triazole-4-carboxylate (2.7 g, 9.4 mmol) in mixture of tetrahydrofuran (20 mL) and water (20 mL) was added lithium hydroxide monohydrate (788 mg, 18.8 mmol). The reaction mixture was stirred at room temperature for 1 h. The solvent was removed under reduced pressure and the residue was diluted with water (5 mL). The aqueous layer was acidified by addition of aqueous HCl (1.0 M) to pH 1, before being extracted with 10% MeOH in $CH_2Cl_2$ (3×20 mL). The organic layer was washed with brine, dried ($Na_2SO_4$), filtered and concentrated in vacuo. The residue was collected and washed with n-pentane to dryness under vacuo to afford the title compound (2.4 g, 88%) as an off white solid. MS (ESI): 273.8 ([M+H]$^+$).

e) [3-methyl-5-[5-(trifluoromethyl)pyrimidin-2-yl]triazol-4-yl]methanol

To solution of 3-methyl-5-[5-(trifluoromethyl)pyrimidin-2-yl]triazole-4-carboxylic acid (2.60 g, 9.52 mmol) in tetrahydrofuran (70 mL) were added at −15° C. triethylamine (8.5 mL, 46.4 mmol) followed by isobutyl chloroformate (4.70 mL, 35.9 mmol). The reaction mixture was stirred at −15° C. for 1.5 h before being filtered directly on a sintered funnel. The collected solid was rinsed with the minimum amount of THF (1 mL). The filtrate to −15° C. then sodium borohydride (874 mg, 23.1 mmol) was added and the mixture stirred for 3 min. The reaction mixture was quenched with water (10 mL) and the resulting mixture extracted with ethyl acetate (20 mL). The organic layer was washed with brine, dried ($Na_2SO_4$), filtered and concentrated in vacuo to give the title compound (1.7 g, 60%) as an off white solid. MS (ESI): 259.8 ([M+H]$^+$).

Building Block N

[3-methyl-5-[6-(trifluoromethyl)pyridazin-3-yl]triazol-4-yl]methanol

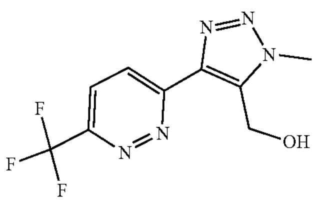 [SMILES: Cn1nnc(-c2ccc(C(F)(F)F)nn2)c1CO]

a) 4,5-dibromo-1-methyl-1H-1,2,3-triazole

To a solution of 4,5-dibromo-1H-1,2,3-triazole (2 g, 8.38 mmol) in dichloromethane (40 mL) under nitrogen at room temperature, was added triethylamine (932 mg, 1.28 mL, 9.21 mmol), followed by iodomethane (1.31 g, 0.574 mL, 9.21 mmol). The reaction mixture was stirred at room temperature for 48 h before being diluted with water and extracted three times with dichloromethane. The combined organic layers were dried ($Na_2SO_4$), filtered and concentrated in vacuo. The crude orange oil was purified by flash chromatography (silica, 0% to 10% ethyl acetate in heptane) to provide the title compound (489 mg, 24% yield) as a white solid. MS (ESI): 241.9 ([M+H]$^+$).

b) 4-bromo-1-methyl-1H-1,2,3-triazole-5-carbaldehyde

To a solution of 4,5-dibromo-1-methyl-1H-1,2,3-triazole (487 mg, 2.02 mmol) in dry tetrahydrofuran (8 mL) under argon at 0° C., was added dropwise a solution of isopropylmagnesium chloride in tetrahydrofuran (2.0 M, 1.82 ml, 3.64 mmol). After stirring at 0° C. for 1 h, N,N-dimethylformamide (443 mg, 0.470 mL, 6.07 mmol) was added dropwise. The mixture was warmed to room temperature over 1.5 h. The reaction mixture was quenched by addition of saturated aqueous $NH_4Cl$ and extracted three times with ethyl acetate. The combined organic layers were dried ($Na_2SO_4$), filtered and concentrated in vacuo. The crude yellow oil was purified by flash column chromatography (silica, 0% to 50% ethyl acetate in heptane) to provide the title compound (271 mg, 71% yield) as a light yellow solid. MS (ESI): 189.9 ([M+H]$^+$).

c) (4-bromo-1-methyl-1H-1,2,3-triazol-5-yl)methanol

To a stirred solution of 4-bromo-1-methyl-1H-1,2,3-triazole-5-carbaldehyde (252 mg, 1.33 mmol) in MeOH (4 mL) was added sodium borohydride (60.8 mg, 1.59 mmol). The reaction mixture was stirred at room temperature for 1 h before being poured into water and extracted twice with dichloromethane. The aqueous layer was extracted twice with ethyl acetate. The combined organic layers were dried ($Na_2SO_4$), filtered and concentrated in vacuo to provide the title compound (185 mg, 73% yield) as a light yellow solid. MS (ESI): 191.8 ([M+H]$^+$).

d) 4-bromo-5-(((tert-butyldimethylsilyl)oxy)methyl)-1-methyl-1H-1,2,3-triazole To a stirred solution of (4-bromo-1-methyl-1H-1,2,3-triazol-5-yl)methanol (500 mg, 2.47 mmol) in dichloromethane (10 mL) was added imidazole (255 mg, 3.71 mmol), followed by tert-butylchlorodimethylsilane (423 mg, 2.72 mmol). The reaction mixture was stirred at room temperature for 1 h then concentrated in vacuo. The residue was poured into water and extracted twice with ethyl acetate. The combined organic layers were dried ($Na_2SO_4$), filtered and concentrated in vacuo. The crude material was purified by flash chromatography (silica, 0% to 50% ethyl acetate in heptane) to provide the title compound (654 mg, 86% yield) as a white solid. MS (ESI): 307.8 ($[M+H]^+$).

e) 3-(5-(((tert-butyldimethylsilyl)oxy)methyl)-1-methyl-1H-1,2,3-triazol-4-yl)-6-(trifluoromethyl)pyridazine To a stirred solution of 4-bromo-5-(((tert-butyldimethylsilyl)oxy)methyl)-1-methyl-1H-1,2,3-triazole (200 mg, 0.653 mmol) in tetrahydrofuran (4 mL) under argon, was added dropwise a solution of n-butyl lithium in hexane (1.6 M, 0.449 mL, 0.718 mmol) at −68° C. The reaction mixture was stirred at −68° C. for 30 min before addition of a solution of $ZnCl_2$ in 2-methyl-tetrahydrofuran (2.0 M, 0.392 mL, 0.784 mmol). The reaction mixture was allowed to warm to room temperature and stirred for an additional 1 h. 3-bromo-6-(trifluoromethyl)pyridazine (148 mg, 0.653 mmol) was added followed by X-Phos Pd G3 (56.4 mg, 0.0653 mmol) and 2-(dicyclohexylphosphino)-2',4',6'-triisopropylbiphenyl (31.8 mg, 0.0653 mmol). The reaction mixture was heated to 70° C. and stirred for 15 h before being concentrated in vacuo. The crude material was purified by flash chromatography (silica, 0% to 100% ethyl acetate in heptane) to provide the title compound (122 mg, 35% yield) as a light yellow solid. MS (ESI): 374.1 ($[M+H]^+$).

f) (1-methyl-4-(6-(trifluoromethyl)pyridazin-3-yl)-1H-1,2,3-triazol-5-yl)methanol A stirred solution of 3-(5-(((tert-butyldimethylsilyl)oxy)methyl)-1-methyl-1H-1,2,3-triazol-4-yl)-6-(trifluoromethyl)pyridazine (118 mg, 0.316 mmol) in tetrahydrofuran (3 mL) was cooled to 0° C. and a solution of tetrabutyl ammonium fluoride in tetrahydrofuran (1.0 M, 0.348 mL, 0.348 mmol) was added dropwise. After stirring at 0° C. for 30 min, the reaction mixture was diluted with ethyl acetate and washed twice with a saturated aqueous $NaHCO_3$. The organic layer was dried ($Na_2SO_4$), filtered and concentrated in vacuo. The crude material was purified by flash chromatography (silica, 0% to 100% ethyl acetate in heptane) to provide the title compound (23 mg, 28% yield) as a white solid. MS (ESI): 259.9 ($[M+H]^+$).

Building Block O

[3-methyl-5-(6-methylpyridazin-3-yl)triazol-4-yl]methanol

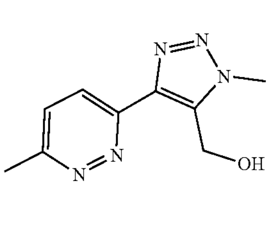

a) 3-(5-(((tert-butyldimethylsilyl)oxy)methyl)-1-methyl-1H-1,2,3-triazol-4-yl)-6-methylpyridazine A three-necked round-bottomed flask was evacuated and backfilled with argon 3 times, then 4-bromo-5-(((tert-butyldimethylsilyl)oxy)methyl)-1-methyl-1H-1,2,3-triazole, ((building block N, step d), 179 mg, 0.583 mmol) and tetrahydrofuran (1.5 mL) were added. The resulting solution was cooled to 0° C. before dropwise addition of a solution of isopropylmagnesium chloride in tetrahydrofuran (2.0 M, 0.370 mL, 0.740 mmol). The reaction mixture was allowed to warm to room temperature and stirred for 1 h. A solution of $ZnCl_2$ in 2-methyl-tetrahydrofuran (2.0 M, 0.404 mL, 0.807 mmol) was added dropwise and the stirring was continued for an additional 1 h. 3-bromo-6-methylpyridazine (80 mg, 0.449 mmol) was quickly added followed by X-Phos Pd G3 (38.7 mg, 0.0449 mmol) and 2-(dicyclohexylphosphino)-2',4',6'-triisopropylbiphenyl (21.8 mg, 0.0449 mmol). The reaction mixture was heated to 70° C. and stirred for 2 h before being concentrated in vacuo. The crude material was purified by flash chromatography (silica, 0% to 100% ethyl acetate in heptane) to provide the title compound (159 mg, 89% yield) as a light yellow solid. MS (ESI) m/z: 320.1 ($[M+H]^+$).

b) (1-methyl-4-(6-methylpyridazin-3-yl)-1H-1,2,3-triazol-5-yl)methanol

In analogy to experiment of building block N f, 3-(5-(((tert-butyldimethylsilyl)oxy)methyl)-1-methyl-1H-1,2,3-triazol-4-yl)-6-methylpyridazine instead of 3-(5-(((tert-butyldimethylsilyl)oxy)methyl)-1-methyl-1H-1,2,3-triazol-4-yl)-6-(trifluoromethyl)pyridazine was converted into the title compound (53 mg, 66%) which was obtained as a white solid. MS (ESI): 205.9 ($[M+H]^+$).

General method 1

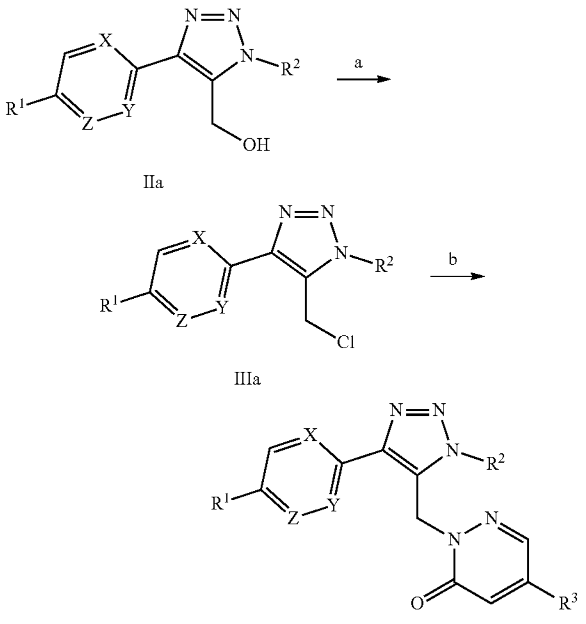

IIa

IIIa

Ia

-continued

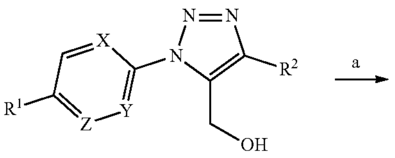

IIb

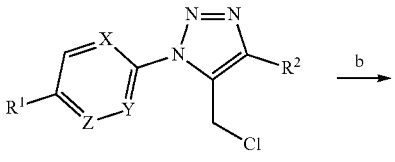

IIIb

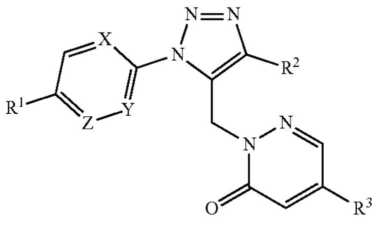

Ib a) To a solution of alcohols (Ia or IIa) (0.965 mmol, 1 eq) in dichloromethane (2 mL) was added at 0° C. thionyl chloride (1.93 mmol, 2 eq). The reaction mixture was stirred at 0° C. for 2 h before being basified by the dropwise addition of a 1.0M solution of aqueous $NaHCO_3$. The mixture was extracted with ethyl acetate then the organic phase was washed with water and brine. The combined organic layers were dried ($MgSO_4$), filtered and concentrated in vacuo.

b) To a mixture of alkyl chlorides (IIa or IIIa) (0.31 mmol, 1 eq). 1H-pyridazin-6-one
(0.37 mmol, 1.2 eq) and potassium carbonate (0.62 mmol, 2 eq) was added acetonitrile (2 mL). The reaction mixture was stirred at 40° C. for 70 h before being cooled to room temperature. The mixture was concentrated under reduced pressure by rotary evaporation and the resulting residue purified directly by flash chromatography to afford desired pyridazinones (Ia or Ib).

General method 2

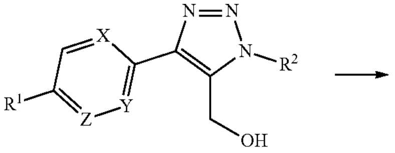

IIa

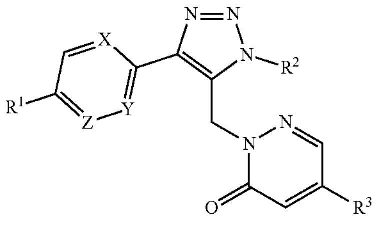

Ia

-continued

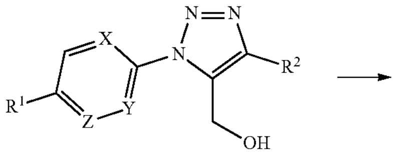

IIb

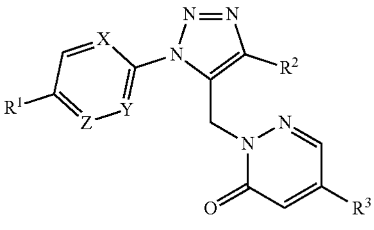

Ib

To a solution of 1H-pyridazin-6-one (1.47 mmol, 1.2 eq) in DMF (5 mL) was added $KO^tBu$ (3.1 mmol, 2.5 eq) under an atmosphere of argon. After 5 min, alcohols (Ta or IIa) (1.23 mmol, 1 eq) were added and the reaction mixture was heated to 150° C. for 6 h. The reaction mixture was quenched by addition of ice cold water and the resulting mixture extracted with ethyl acetate. The organic phase was washed with brine, dried ($Na_2SO_4$), filtered and concentrated in vacuo. Purification by preparative HPLC afforded desired pyridazinones (Ta or Tb).

General method 3

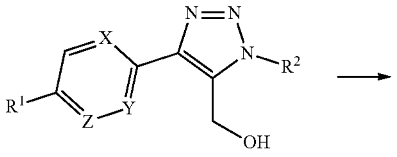

IIa

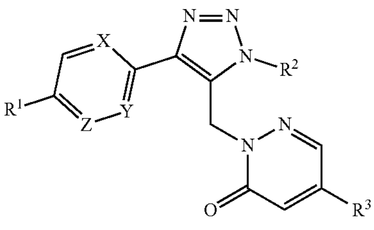

Ia

To a solution of alcohols (Ia) (4.13 mmol, 1 eq) and 1H-pyridazin-6-one (4.96 mmol, 1.2 eq) in dry tetrahydrofuran (70 mL) was added at room temperature triphenylphosphine (4.96 mmol, 1.2 eq). The mixture was cooled to 0° C. then a solution of DEAD (4.9 mmol, 1.2 eq) in dry tetrahydrofuran (10 mL) was slowly added. The reaction mixture was allowed to warm to room temperature and stirred for 4 h. The reaction mixture was concentrated under reduced pressure by rotary evaporation and the resulting residue purified directly by flash chromatography to afford desired pyridazinones (Ia).

General method 4

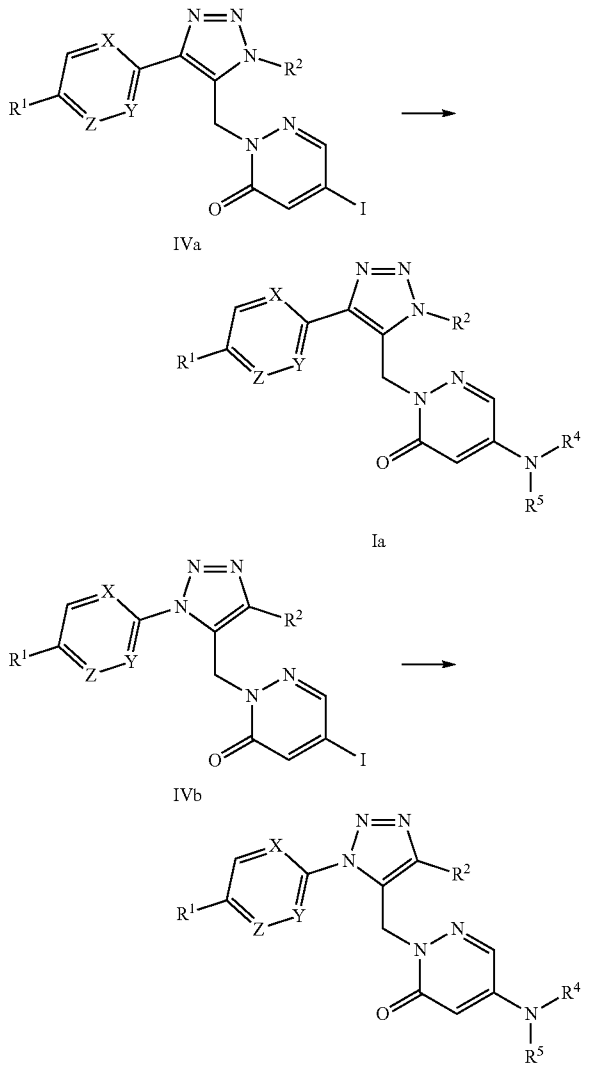

IVa

Ia

IVb

Ib

To a mixture of 5-iodo-pyridazin-3-ones (IVa or IVb) (0.224 mmol, 1 eq) and an amine (0.26 mmol, 1.2 eq) in DMSO (5 mL) was added at room temperature potassium carbonate (1.12 mmol, 5 eq). The reaction mixture was heated to 90° C. and stirred for 16 h before being cooled to room temperature. The mixture was diluted with water and extracted with ethyl acetate. The combined organic layers were washed with brine, dried ($Na_2SO_4$) and concentrated in vacuo. Purification by preparative HPLC afforded desired pyridazinones (Ia or Ib).

General method 5

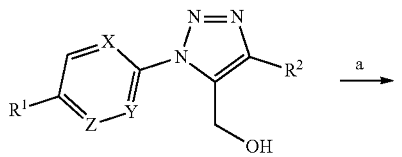

IIb

-continued

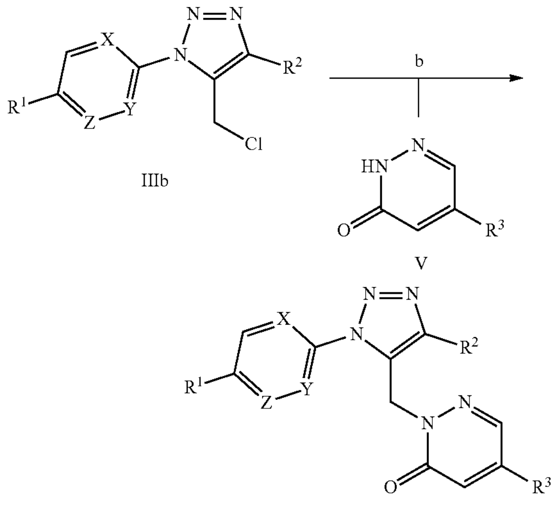

IIIb

V

Ib a) To a cold (0° C.) solution of alcohols (IIa) (15.4 mmol, 1 eq) in dichloromethane (20 mL) were added methane sulphonyl chloride (46 mmol, 3 eq) and triethylamine (46 mmol, 3 eq). After 10 min, the reaction mixture was allowed to warm to room temperature and stirred for 2 h. The mixture was diluted with cold water and extracted with dichloromethane. The organic layer was washed with brine, dried ($Na_2SO_4$), filtered and concentrated in vacuo. Purification by flash chromatography afforded alkyl chlorides (IIIa).

b) To a suspension of KO$^t$Bu (0.97 mmol, 1.25 eq) in tetrahydrofuran (10 mL) was added at room temperature pyridazinones (V) (0.927 mmol, 1.2 eq). After 10 min, alkyl chlorides (IIIa) (0.770 mmol, 1 eq) were added and the reaction mixture was heated to reflux for 16 h. The mixture was allowed to warm to room temperature then filtered directly through a pad of celite and the filtrate was concentrated in vacuo. Purification by preparative HPLC afforded desired pyridazinones (Ib).

General method 6

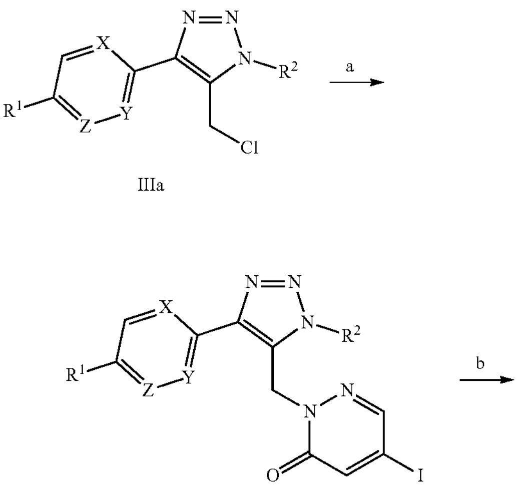

IIIa

IVa

-continued

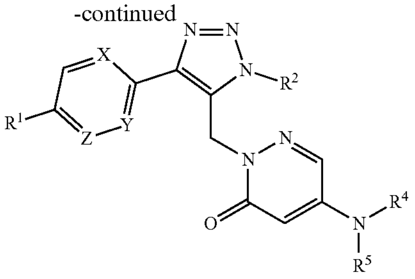

Ia a) To a mixture of alkyl chlorides (IIa) (8.53 mmol, 1 eq), 5-iodo-2,3-dihydropyridazin-3-one (9.38 mmol, 1.1 eq) and potassium carbonate (12.8 mmol, 1.5 eq) was added acetone (100 mL) and the reaction mixture was stirred at 50° C. for 16 h under an atmosphere of argon. The resulting suspension was filtered off and the filtrate was concentrated in vacuo. Purification by flash chromatography afforded aryl iodides (IVa).

b) Under an argon atmosphere, aryl iodides (IVa) (0.250 mmol, 1 eq), an amine (0.30 mmol, 1.2 eq) and cesium carbonate (0.610 mmol, 2.4 eq) were dissolved in 1,4-dioxane (5 mL). The reaction mixture was purged with a stream of argon for 10 min before addition of tris(dibenzylideneacetone)dipalladium(0) (0.012 mmol, 0.05 eq) and X-phos (0.024 mmol, 0.1 eq). The mixture was flushed with a stream of argon for 5 min then heated to 110° C. and stirred for 16 h. After cooling to room temperature the mixture was diluted with 10% methanol in dichloromethane (20 mL). The suspension was filtered off and the filtrate was concentrated in vacuo. Purification by flash chromatography afforded desired pyridazinones (Ia).

General method 7

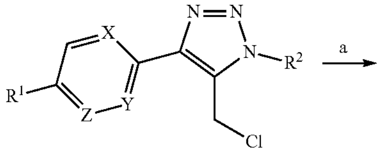

IIIa

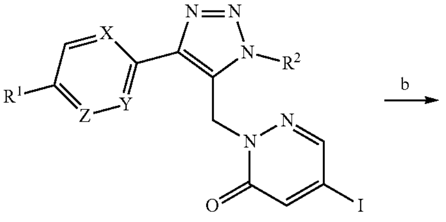

IVa

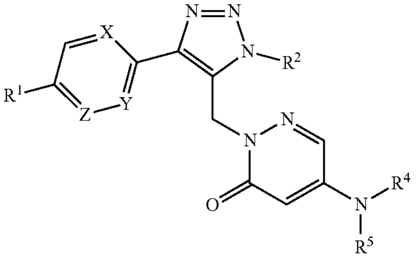

Ia

-continued

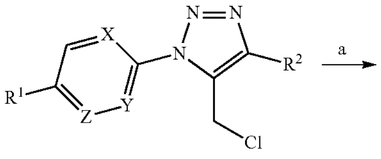

IIIb

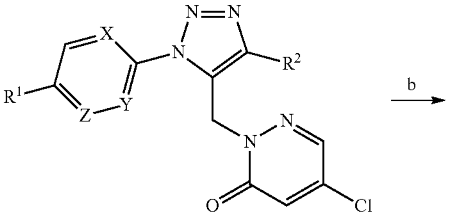

Vb

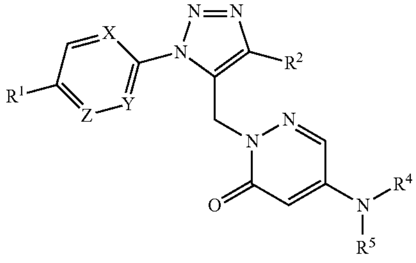

Ib a) To a solution of alkyl chlorides (IIa, IIIa) (2.13 mmol, 1 eq) in acetone (6 mL) was added a mixture of 5-chloropyridazin-3(2H)-one or 5-iodo-2,3-dihydropyridazin-3-one (2.77 mmol, 1.3 eq) and potassium carbonate (5.32 mmol, 2.5 eq). After 30 min, the resulting thick suspension was diluted with acetone (6 mL). The reaction mixture was stirred at room temperature for 20 h. The suspension was then filtered off and the filter cake was rinsed well with acetone. The filtrate was concentrated in vacuo and purified by flash chromatography to afford aryl iodides (IVa) or aryl chlorides (Vb).

b) To a solution of aryl iodides or chlorides (IVa, Vb) (0.282 mmol, 1 eq) in acetonitrile (1 mL) was added an amine as an hydrochloride or a free base (0.339 mmol, 1.2 eq) and potassium carbonate (1.41 mmol, 5.0 eq). The vial was capped and heated to 50° C. and stirred for 18 to 48 hours. After cooling to room temperature the reaction mixture was filtered off and the filter cake rinsed well with acetonitrile. The filtrate was concentrated in vacuo and purified by flash chromatography to afford desired pyridazinones (Ia, Ib).

General method 8

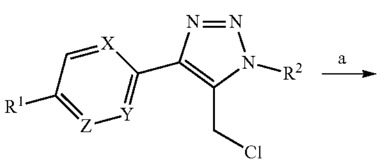

IIIa

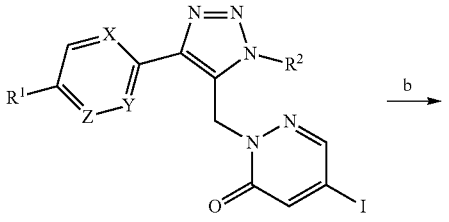

Va

-continued

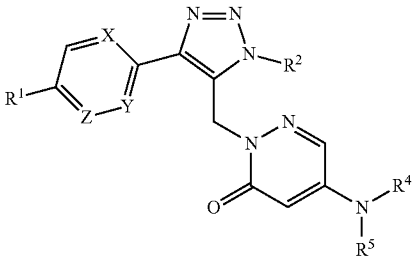

Ia a) To a suspension of alkyl chlorides (IIa) (3.00 g, 1 eq) in acetonitrile (50 mL) was added cesium carbonate (10 g, 2.5 eq) and 5-chloro-2H-pyridazine-3-one (1.7 g, 1.1 eq). The reaction mixture was heated to 90° C. and stirred for 1 h before being cooled to room temperature. The mixture was diluted with cold water, and the aqueous layer was extracted with ethyl acetate. The organic layer was washed with brine, dried ($Na_2SO_4$), filtered and concentrated in vacuo. Purification by flash chromatography afforded aryl chlorides (Va).

b) In analogy to experiment of general method 4, aryl chlorides (Va) were converted into desired pyridazinones (Ia).

General method 9

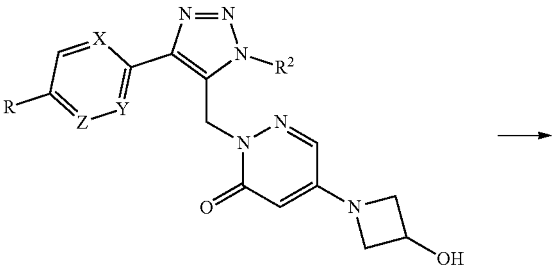

VIa

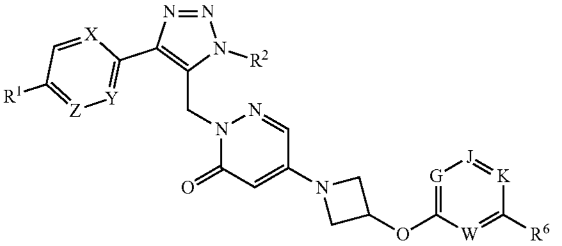

VIIa

To a solution of alcohols (VIa) (0.256 mmol, 1 eq) in dry 1,4-dioxane (7 mL) was added at 0° C. sodium hydride (60% dispersion in mineral oil) (0.384 mmol, 1.5 eq). After 15 min, a solution of an heteroaryl chloride (0.384 mmol, 1.5 eq) in 1,4-dioxane (2 mL) was added dropwise. The reaction mixture was allowed to warm to room temperature and stirred for 16 h before being quenched by addition of saturated aqueous $NH_4Cl$. The mixture was extracted with ethyl acetate (3×50 mL). The combined organic layers were washed with brine, dried ($Na_2SO_4$), and concentrated in vacuo. Purification by HPLC afforded the desired pyridazinones (VIa).

General method 10

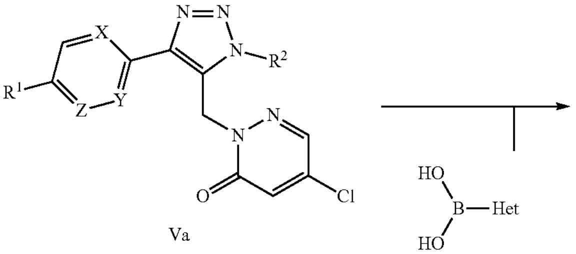

Va or

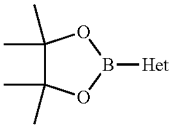

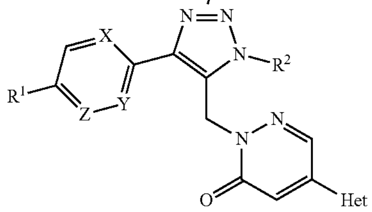

Ia

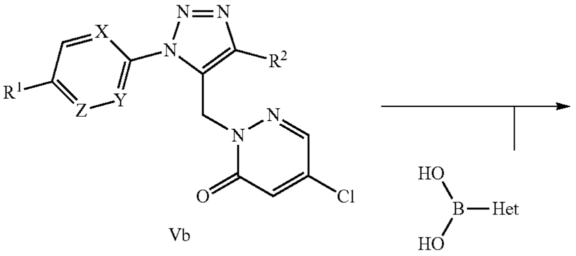

Vb or

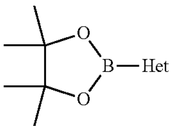

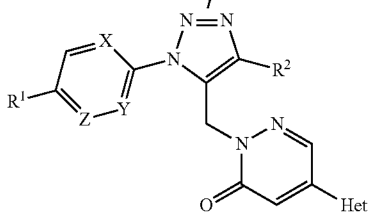

Ib

To a solution of aryl chlorides (Va, Vb) (0.19 mmol, 1 eq) at room temperature in 1,4-dioxane (4 ml) were added water (0.5 ml) and sodium carbonate (0.59 mmol, 3.1 eq). The mixture was purged with argon for 10 min, then an heteroaryl boronic acid or an heteroaryl boronic acid pinacol ester (0.49 mmol, 2.6 eq) and tetrakis(triphenylphosphine) palladium(0) (0.006 mmol, 0.03 eq) were added. The mixture was purged again with argon for 5 min. The vial was capped and heated to 100° C. and stirred for 16 hours. After cooling to room temperature the reaction mixture was filtered off through a celite pad and the filter cake was rinsed with ethyl acetate (10 ml). The filtrate was concentrated in vacuo and purified by preparative HPLC or by flash chromatography to afford desired pyridazinones (Ia, Ib).

Preparation of Amines and Heterocyclic Compounds (S)-5-Oxa-2-azaspiro[3,4]octan-7-ol 2,2,2-trifluoroacetic acid

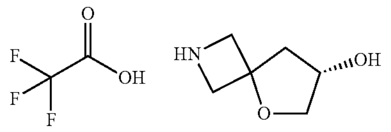 [SMILES: O=C(O)C(F)(F)F ; O[C@@H]1COC2(CNC2)C1]

a) tert-butyl 7-benzoyloxy-5-oxa-2-azaspiro[3.4]octane-2-carboxylate

To a solution of tert-butyl 7-hydroxy-5-oxa-2-azaspiro[3.4]octane-2-carboxylate (0.200 g, 0.872 mmol) in dichloromethane (3.4 mL) at 0° C., was added pyridine (0.22 mL, 2.72 mmol) followed by dropwise addition of benzoyl chloride (0.20 mL, 1.72 mmol). After 15 min, the ice bath was removed and the reaction mixture was stirred at room temperature for 2 h. The reaction was quenched by addition of aqueous HCl (1.0 M, 5 mL) and the mixture was extracted with dichloromethane (20 mL). The aqueous layer was back extracted with dichloromethane (20 mL). The organic layers were combined, dried ($Na_2SO_4$), filtered and concentrated in vacuo. Purification by flash chromatography (silica, 0% to 30% ethyl acetate in heptane) afforded the title compound (257 mg, 89%) as a white solid. MS (ESI): 278.2 ($[M-C_4H_8+H]^+$).

b) tert-butyl (7S)-7-benzoyloxy-5-oxa-2-azaspiro[3.4]octane-2-carboxylate and tert-butyl (7R)-7-benzoyloxy-5-oxa-2-azaspiro[3.4]octane-2-carboxylate tert-butyl 7-(benzoyloxy)-5-oxa-2-azaspiro[3.4]octane-2-carboxylate (1.160 g, 3.48 mmol) was separated by chiral preparative HPLC (Reprosil Chiral NR, 15% isopropanol in hetane, 220 nm), affording

- (−) enantiopure (S)-title compound (470 mg, 41%) as a colourless oil. MS (ESI): inconclusive.
- (+) enantiopure (R)-title compound (549 mg, 47%) as a colourless oil. MS (ESI): inconclusive.

c) (S)-tert-butyl 7-hydroxy-5-oxa-2-azaspiro[3.4]octane-2-carboxylate

In a sealed flask, (S)-tert-butyl 7-(benzoyloxy)-5-oxa-2-azaspiro[3.4]octane-2-carboxylate (465 mg, 1.39 mmol) was dissolved in a solution of ammonia in methanol (7.0 N, 8.0 mL, 56 mmol). The reaction mixture was stirred at room temperature for 16 h before being concentrated in vacuo. The residue was purified directly by flash chromatography (silica, 0% to 70% ethyl acetate in heptane) to afford the (+)-title compound (317 mg, 99%) as a colourless oil. MS (ESI): inconclusive.

$^1H$ NMR (300 MHz; $CDCl_3$): δ(ppm) 4.53 (1H, m), 4.08 (1H, d, J=9.5 Hz), 4.03 (2H, s), 3.96 (1H, dd, J=9.9, 4.2 Hz), 3.92 (1H, d, J=8.9 Hz), 3.84 (1H, app dt, 2.14, J=9.9, 1.2 Hz), 2.26 (1H, dq, J=13.7, 2.0, 1.0 Hz), 2.18 (1H, dd, J=13.7, 5.1 Hz), 1.61 (1H, d, J=3.8 Hz), 1.44 (9H, s).

d) (7S)-5-oxa-2-azaspiro[3.4]octan-7-ol; 2,2,2-trifluoroacetic acid (S)-tert-butyl 7-hydroxy-5-oxa-2-azaspiro[3.4]octane-2-carboxylate (0.210 g, 0.916 mmol) was dissolved in dichloromethane (2.4 mL) and the colourless solution was cooled to 0° C. before the dropwise addition of trifluoroacetic acid (0.38 mL, 4.93 mmol). After 15 min, the ice bath was removed and the reaction mixture was stirred at room temperature for 2 h. The resulting mixture was concentrated in vacuo to afford the title compound (342 mg, 92%) as a colourless oil. MS (ESI): 130.1 ($[M+H]^+$).

(7R)-5-oxa-2-azaspiro[3.4]octan-7-ol2,2,2-trifluoroacetic acid

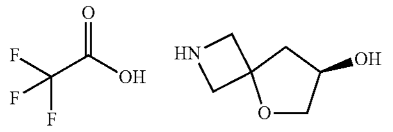 [SMILES: O=C(O)C(F)(F)F ; O[C@H]1COC2(CNC2)C1]

a) (R)-tert-butyl 7-hydroxy-5-oxa-2-azaspiro[3.4]octane-2-carboxylate

In analogy to experiment of (S)-tert-butyl 7-hydroxy-5-oxa-2-azaspiro[3.4]octane-2-carboxylate, (R)-tert-butyl 7-(benzoyloxy)-5-oxa-2-azaspiro[3.4]octane-2-carboxylate instead of (S)-tert-butyl 7-(benzoyloxy)-5-oxa-2-azaspiro[3.4]octane-2-carboxylate was converted into the (−)-title compound (326 mg, 87%) which was obtained as a colourless oil. MS (ESI): inconclusive.

$^1H$ NMR (300 MHz; $CDCl_3$): δ(ppm) 4.53 (1H, m), 4.08 (1H, d, J=9.5 Hz), 4.03 (2H, s), 3.96 (1H, dd, J=9.9, 4.2 Hz), 3.92 (1H, d, J=8.9 Hz), 3.84 (1H, app dt, 2.14, J=9.9, 1.2 Hz), 2.26 (1H, dq, J=13.7, 2.0, 1.0 Hz), 2.18 (1H, dd, J=13.7, 5.1 Hz), 1.61 (1H, d, J=3.8 Hz), 1.44 (9H, s).

b) (7R)-5-oxa-2-azaspiro[3.4]octan-7-ol; 2,2,2-trifluoroacetic acid

In analogy to experiment of (7S)-5-oxa-2-azaspiro[3.4]octan-7-ol; 2,2,2-trifluoroacetic acid, (R)-tert-Butyl 7-hydroxy-5-oxa-2-azaspiro[3.4]octane-2-carboxylate instead of (S)-tert-butyl 7-hydroxy-5-oxa-2-azaspiro[3.4]octane-2-carboxylate was converted into the title compound (367 mg, 94%) which was obtained as a colourless oil. MS (ESI): 130.1 ($[M+H]^+$).

(7R)-7-methoxy-5-oxa-2-azaspiro[3.4]octane hydrochloride

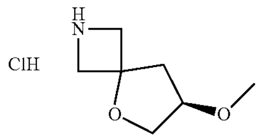

a) tert-butyl (7R)-7-methoxy-5-oxa-2-azaspiro[3.4]octane-2-carboxylate

To a solution of (R)-tert-butyl 7-hydroxy-5-oxa-2-azaspiro[3.4]octane-2-carboxylate (200 mg, 0.741 mmol) in a mixture of DMF (2 mL) and tetrahydrofuran (2 mL) was added at room temperature NaH (60% dispersion in mineral oil, 47.4 mg, 1.19 mmol). The reaction mixture was stirred at room temperature for 30 min before addition of iodomethane (0.93 mL, 1.48 mmol). After 16 h, the reaction mixture was quenched by addition of water (10 mL). The resulting mixture was extracted with ethyl acetate (2×50 mL). The combined organic layers were washed twice with water (10 mL) and brine (10 mL), dried ($Na_2SO_4$), filtered and concentrated in vacuo. Purification by flash chromatography (silica, 0% to 5% methanol in dichloromethane) afforded the title compound (124 mg, 65%) as a colourless oil.

$^1H$ NMR (300 MHz; $CDCl_3$): δ(ppm) 3.89-4.08 (7H, m), 3.30 (3H, s), 2.34 (1H, dd, J=13.6, 1.7 Hz), 2.05 (1H, dd, J=13.7, 5.4 Hz), 1.43 (9H, s).

b) (R)-7-methoxy-5-oxa-2-azaspiro[3.4]octane hydrochloride

To a stirred solution of (R)-tert-butyl 7-methoxy-5-oxa-2-azaspiro[3.4]octane-2-carboxylate (124 mg, 0.484 mmol) in 1,4-dioxane (2 mL) was added a solution of HCl in 1,4-dioxane (4.0 M, 1.82 mL, 7.26 mmol). The reaction mixture was stirred at room temperature overnight. The resulting precipitate was collected by filtration through a sintered funnel, washed with further 1,4-dioxane then dried under high vacuum to afford the title compound (95.8 mg, 99%) as a white solid. MS (ESI): 144.0 ($[M+H]^+$).

(7S)-7-methoxy-5-oxa-2-azaspiro[3.4]octane hydrochloride

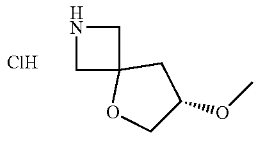

a) tert-butyl (7S)-7-methoxy-5-oxa-2-azaspiro[3.4]octane-2-carboxylate

To a solution of (S)-tert-butyl 7-hydroxy-5-oxa-2-azaspiro[3.4]octane-2-carboxylate (202 mg, 0.881 mmol) in a mixture of DMF (2 mL) and tetrahydrofuran (2 mL) was added at room temperature NaH (60% dispersion in mineral oil, 56.4 mg, 1.41 mmol). The reaction mixture was stirred at room temperature for 30 min before addition of iodomethane (0.110 mL, 1.76 mmol). After 16 h, the reaction mixture was quenched by addition of water (10 mL). The resulting mixture was extracted with ethyl acetate (2×50 mL). The combined organic layers were washed twice with water (10 mL) and brine (10 mL), dried ($Na_2SO_4$), filtered and concentrated in vacuo. Purification by flash chromatography (silica, 0% to 60% ethyl acetate in heptane) afforded the title compound (176 mg, 82%) as a colourless oil.

$^1H$ NMR (300 MHz; $CDCl_3$): δ(ppm) 3.89-4.08 (7H, m), 3.30 (3H, s), 2.34 (1H, dd, J=13.6, 1.7 Hz), 2.05 (1H, dd, J=13.7, 5.4 Hz), 1.43 (9H, s).

b) (S)-7-methoxy-5-oxa-2-azaspiro[3.4]octane hydrochloride

In analogy to experiment of (R)-7-methoxy-5-oxa-2-azaspiro[3.4]octane hydrochloride. tert-butyl (7S)-7-methoxy-5-oxa-2-azaspiro[3.4]octane-2-carboxylate instead of (R)-tert-butyl 7-methoxy-5-oxa-2-azaspiro[3.4]octane-2-carboxylate was converted into the title compound (132 mg, 71%) as a white solid. MS (ESI): 144.1 ($[M+H]^+$).

3-(2,2,2-trifluoroethoxy)azetidine 2,2,2-trifluoroacetic acid

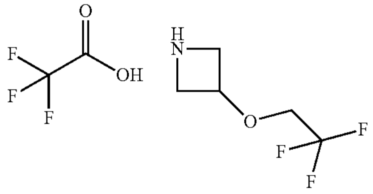

a) tert-butyl 3-(2,2,2-trifluoroethoxy)azetidine-1-carboxylate

To a solution of tert-butyl-3-hydroxyazetidine-1-carboxylate (500 mg, 2.89 mmol) in DMF (8.0 mL) was added at room temperature NaH (60% dispersion in mineral oil, 173 mg, 4.33 mmol). After 30 min, the reaction mixture was cooled to 0° C. and 2,2,2-trifluoroethyl trifluoromethanesulfonate (0.67 ml, 4.65 mmol) was added dropwise. After 15 min, the ice bath was removed and the reaction mixture was stirred at room temperature overnight. The reaction mixture was quenched with water then extracted with TBME (90 mL) and water (15 mL). The aqueous layer was back extracted with TBME (90 mL). The combined organic layers were washed with water (3×15 mL) and brine (15 mL), dried ($Na_2SO_4$), filtered and evaporated under reduced pressure. Purification by flash chromatography (silica, 0% to 30% ethyl acetate in heptane) afforded the title compound (428 mg, 58%) as a light yellow oil. MS (ESI): 256.3 ($[M+H]^+$).

$^1H$ NMR (300 MHz; $CDCl_3$): δ(ppm) 4.36 (1H, tt, J=6.3, 4.5 Hz), 4.07-4.15 (2H, m), 3.86-3.94 (2H, m), 3.80-3.85 (1H, m), 3.74-3.80 (1H, m), 1.44 (9H, s).

b) 3-(2,2,2-trifluoroethoxy)azetidine 2,2,2-trifluoroacetic acid

To a solution of tert-butyl 3-(2,2,2-trifluoroethoxy)azetidine-1-carboxylate (340 mg, 1.33 mmol) in dichloromethane (3.5 mL) under nitrogen at 0° C., was added trifluoroacetic acid (616 μl, 7.99 mmol). The reaction mixture was stirred at room temperature for 3 h. The reaction mixture was concentrated in vacuo to afford the title compound (463 mg, 91%) as a colourless oil. MS (ESI): 156.1 ($[M+H]^+$).

3-(2,2,2-trifluoro-1,1-dimethyl-ethoxy)azetidine hydrochloride

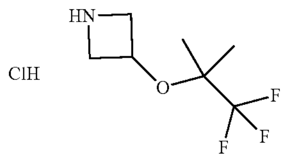

a) (1-benzhydrylazetidin-3-yl)methanesulfonate

To a solution of 1-(diphenylmethyl)-3-hydroxyazetidine (1.087 g, 4.54 mmol) in dichloromethane (6.0 mL) was added triethylamine (1.27 mL, 9.08 mmol). The mixture was cooled to 0° C. before the dropwise addition of methanesulfonyl chloride (0.425 mL, 5.45 mmol). The reaction mixture was stirred at 0° C. for 30 min then allowed to warm to room temperature and stirred for a further 1 h. The reaction mixture was poured into water (5 mL) and extracted with dichloromethane (2×10 mL). The combined organic layers were dried ($Na_2SO_4$), filtered and concentrated in vacuo to afford the title compound (1.563 g, 100%) as an off-white solid. MS (ESI): 318.2 ($[M+H]^+$).

b) 1-benzhydryl-3-(2,2,2-trifluoro-1,1-dimethyl-ethoxy)azetidine

To a solution of 1,1,1-trifluoro-2-methylpropan-2-ol (144 mg, 0.123 mL, 1.12 mmol) in DMF (1 mL) was added NaH (60% dispersion in mineral oil, 44.9 mg, 1.12 mmol). After stirring at room temperature for 30 min, 1-benzhydrylazetidin-3-yl methanesulfonate (178 mg, 0.561 mmol) was added in one portion. The suspension was heated to 70° C. for 18 h, then 110° C. for 2 h, and finally, at 130° C. for 4 h before being cooled to room temperature. The reaction mixture was poured into water (10 mL) and extracted with ethyl acetate (20 mL). The aqueous layer was back extracted with ethyl acetate (20 mL). The combined organic layers were washed with brine (20 mL), dried ($Na_2SO_4$), filtered and concentrated in vacuo. Purification by flash chromatography (silica, 0% to 40% ethyl acetate in heptane) afforded the title compound (71 mg, 36%) as a brown oil. MS (ESI): 350.2 ($[M+H]^+$).

c) 3-(2,2,2-trifluoro-1,1-dimethyl-ethoxy)azetidine hydrochloride

To a solution of 1-benzhydryl-3-((1,1,1-trifluoro-2-methylpropan-2-yl)oxy)azetidine (71 mg, 0.203 mmol) in methanol (4 mL) was added under nitrogen hydrochloric acid in 1,4-dioxane (4.0 M, 0.152 mL, 0.610 mmol) followed by Pd/C (10 wt. %, 35 mg, 32.9 μmol). The resulting suspension was purged by evacuation and then back filled with a stream of hydrogen (balloon) for three times. The reaction mixture was heated to 50° C. for 8 h under hydrogen atmosphere, then filtered directly through a pad of Hyflo®. The filter cake was rinsed with methanol (10 mL) and the filtrate concentrated in vacuo to afford the title compound (77.3 mg, 100%) as an off-white solid. MS (ESI): 184.1 ($[M+H]^+$).

(S)-7-fluoro-5-oxa-2-azaspiro[3.5]nonane hydrochloride

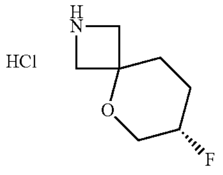

a) 2-fluoroprop-2-en-1-ol

To a mixture of $LiAlH_4$ (131.2 g, 3.46 mol) in diethyl ether (3 L) was carefully added $AlCl_3$ (63.0 mL, 1.15 mol) at −5° C. The mixture was stirred at −5° C. for 30 min, then methyl 2-fluoroprop-2-enoate (240 g, 2.31 mol) was added dropwise at −5° C. The mixture was stirred at −5° C. for other 3.5 h. Wet sodium sulfate was added at 0° C. and the mixture was filtered. The filtrate was isolated by atmospheric distillation at 50° C. affording the title compound (163.0 g, 46%) as colourless liquid in ether. $^1H$ NMR (400 MHz, $CDCl_3$): 4.63 (1H, dd, J=17.2, 2.8 Hz), 4.53 (1H, dd, J=51.6, 2.8 Hz), 4.08 (1H, dd, J=10.8, 3.2 Hz), 3.30 (1H, m).

b) 2-fluoroprop-2-enyl methanesulfonate

To a mixture of 2-fluoroprop-2-en-1-ol (160.0 g, 1.05 mol) and triethylamine (219 mL, 1.58 mol) in dichloromethane (400 mL) was added MsCl (97.6 mL, 1.26 mol) at −30° C. The mixture was stirred at −30° C. for 1 h. The mixture was diluted with dichloromethane (500 mL) and washed with water (3×700 mL). The organic phase was dried ($Na_2SO_4$), filtered and concentrated in vacuo to afford the title compound (119.3 g, crude) as a yellow oil. $^1H$ NMR (400 MHz, $CDCl_3$): 4.95 (1H, dd, J=15.2, 3.6 Hz), 4.86-4.70 (3H, m), 3.08 (3H, s).

c) tert-butyl 3-allyl-3-hydroxyazetidine-1-carboxylate

To a mixture of tert-butyl 3-oxoazetidine-1-carboxylate (150.0 g, 876 mmol) in tetrahydrofurane (1 L) was added allylmagnesium bromide (1.0 M, 876 mL) at −78° C. The mixture was stirred at −78° C. for 1.5 h, then quenched with saturated aqueous $NH_4Cl$ (10 L) and extracted with ethyl acetate (3×2 L). The combined organic phase was dried ($Na_2SO_4$), filtered and concentrated in vacuo to afford the title compound (192.5 g, crude) as an orange oil. MS (ESI): 158.1 ($[M-C_4H_8+H]^+$).

d) tert-butyl 3-allyl-3-((2-fluoroallyl)oxy)azetidine-1-carboxylate

To a mixture of tert-butyl 3-allyl-3-hydroxyazetidine-1-carboxylate (150.0 g, 703 mmol) in DMF (750 mL) was added sodium hydride (60% dispersion in mineral oil, 42.2 g, 1.05 mol) at 0° C. and stirred for 1 h. 2-Fluoroprop-2-enyl methanesulfonate (119.2 g, 773 mmol) was added to the mixture at 0° C. and stirred for 1 h. The mixture was quenched with saturated aqueous $NH_4Cl$ (1.5 L) and extracted with MTBE (3×800 mL). The combined organic phase was washed with water (3×500 mL), dried ($Na_2SO_4$), filtered and concentrated in vacuo. Purification by chromatography (silica, petroleum ether/ethyl acetate) afforded the title compound (80.0 g, crude) as an orange oil. The product was used for next step directly. $^1$H NMR (400 MHz, $CDCl_3$): 5.86-5.76 (1H, m), 5.25-5.20 (2H, m), 4.77 (1H, d, J=16.4 Hz), 4.62 (1H, d, J=48.4 Hz), 3.99-3.92 (4H, m), 3.80-3.73 (2H, m), 2.58-2.54 (2H, m), 1.47 (9H, s).

e) tert-butyl 7-fluoro-5-oxa-2-azaspiro[3.5]non-7-ene-2-carboxylate

To a solution of tert-butyl 3-allyl-3-((2-fluoroallyl)oxy) azetidine-1-carboxylate (1.51 g, 5.57 mmol) in dry degassed toluene (928 mL) under argon at room temperature, was added (1,3-dimesitylimidazolidin-2-ylidene)(2-isopropoxy-benzylidene)ruthenium(VI)chloride (349 mg, 557 μmol). The mixture was stirred at 100° C. for 1.5 hr, then filtered over dicalite. The filtrate was concentrated in vacuo. Purification by flash chromatography (silica, ethyl acetate/heptane) afforded the title compound (1.28 g, 95%) as a green oil. MS (ESI): 188.1 ($[M-C_4H_8+H]^+$).

f) tert-butyl 7-fluoro-5-oxa-2-azaspiro[3.5]nonane-2-carboxylate

To a solution of tert-butyl 7-fluoro-5-oxa-2-azaspiro[3.5] non-7-ene-2-carboxylate (1.26 g, 5.18 mmol) in methanol (51.8 mL) at room temperature was added Pd/C (10 wt. %, 276 mg, 0.259 mmol). The mixture was stirred under hydrogen atmosphere at room temperature for 18 h. The reaction mixture was filtered through a pad of dicalite and washed with methanol. The filtrate was concentrated in vacuo affording the title compound (1.18 g, 93%) as a green solid. MS (ESI): 190.1 ($[M-C_4H_8+H]^+$).

g) 7-fluoro-5-oxa-2-azaspiro[3.5]nonane hydrochloride

To a solution of tert-butyl 7-fluoro-5-oxa-2-azaspiro[3.5] nonane-2-carboxylate (1.18 g, 4.81 mmol) in dichloromethane (14.5 mL) at room temperature, was added HCl in 1,4-dioxane (4.0 M, 6.01 ml, 24.1 mmol). The mixture was stirred at room temperature for 24 h, concentrated in vacuo and dried to afford the title compound (845 mg, 97%) as an off-white solid. MS (ESI): 146.1 ($[M+H]^+$).

h) (S)-benzyl 7-fluoro-5-oxa-2-azaspiro[3.5]nonane-2-carboxylate and (R)-benzyl 7-fluoro-5-oxa-2-azaspiro[3.5]nonane-2-carboxylate To a suspension of 7-fluoro-5-oxa-2-azaspiro[3.5]nonane hydrochloride (4.43 g, 23.9 mmol) in dichloromethane (44.4 mL) at 0-5° C., was added triethylamine (10.4 ml, 74.6 mmol) and benzyl chloroformate (7.13 ml, 49.9 mmol). The mixture was stirred at room temperature. After 2 h, triethylamine (2.5 ml, 17.9 mmol) and benzyl chloroformate (1.71 ml, 12.0 mmol) were added. After 3 h stirring at room temperature, the reaction mixture was diluted with aqueous 1.0 M HCl. The aqueous layer was extracted with dichloromethane. The combined organic layers were dried ($Na_2SO_4$), filtered and concentrated in vacuo. The mixture was separated by chiral preparative HPLC (Chiralpak AD, 60:40 heptane/ethanol, 203 n), affording (+) enantiopure (R)-title compound (2.06 g, 31%) as an orange oil, MS (ESI): 280.2 ($[M+H]^+$).

(−) enantiopure (S)-title compound (2.07 g, 31%) as an orange oil, MS (ESI): 280.2 ($[M+H]^+$).

i) (S)-7-fluoro-5-oxa-2-azaspiro[3.5]nonane hydrochloride or enantiomer

To a solution of (S)-benzyl 7-fluoro-5-oxa-2-azaspiro [3.5]nonane-2-carboxylate (2 g, 7.16 mmol) in methanol (71.6 mL) at room temperature was added Pd/C (10 wt. %, 762 mg, 0.716 mmol) and aqueous HCl (4.0 M, 2.15 ml, 8.59 mmol). The mixture was stirred under hydrogen atmosphere at room temperature for 18 h. The reaction mixture was filtered through a pad of dicalite and washed with methanol. The filtrate was concentrated in vacuo affording the title compound (1.27 g, 97%) as an off-white solid. MS (ESI): 146.2 ($[M+H]^+$), specific optical rotation: −41.5° (methanol, 0.667 g/100 mL).

(R)-7-fluoro-5-oxa-2-azaspiro[3.5]nonane hydrochloride or enantiomer

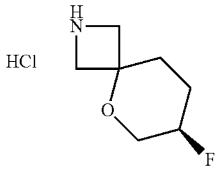

To a solution of (R)-benzyl 7-fluoro-5-oxa-2-azaspiro [3.5]nonane-2-carboxylate or enantiomer (2 g, 7.16 mmol) in methanol (71.6 mL) at room temperature was added Pd/C (10 wt. %, 762 mg, 0.716 mmol) and aqueous HCl (4.0 M, 2.15 ml, 8.59 mmol). The mixture was stirred under hydrogen atmosphere at room temperature for 19 h. The reaction mixture was filtered through a pad of dicalite and washed with methanol. The filtrate was concentrated in vacuo affording the title compound (1.10 g, 85%) as an off-white solid. MS (ESI): 146.2 ($[M+H]^+$), specific optical rotation: +38.6° (methanol, 0.667 g/100 mL).

(R)-7-methyl-5-oxa-2-azaspiro[3.5]nonane hydrochloride or enantiomer

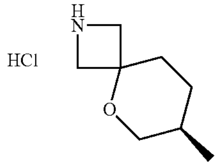

a) tert-butyl 3-allyl-3-((2-methylallyl)oxy)azetidine-1-carboxylate

In analogy to the experimental procedure of tert-butyl 3-allyl-3-((2-fluoroallyl)oxy)azetidine-1-carboxylate, 3-bromo-2-methylprop-1-ene instead of 2-fluoroprop-2-enyl methanesulfonate was converted into the title compound (1.05 g, 84%) which was obtained as a light yellow liquid. MS (ESI): 265.5 ($[M+H]^+$).

b) tert-butyl 7-methyl-5-oxa-2-azaspiro[3.5]non-7-ene-2-carboxylate

To a solution of tert-butyl 3-allyl-3-((2-methylallyl)oxy) azetidine-1-carboxylate (1.02 g, 3.82 mmol) in dry degassed dichloromethane (636 mL) under Argon at room temperature, was added Grubbs II (324 mg, 0.382 mmol). The mixture was stirred at 40° C. for 19 hr. The reaction mixture was concentrated in vacuo. Purification by flash chromatography (silica, ethyl acetate/heptane) afforded the title compound (859 mg, 94%) as a brown oil. MS (ESI): 184.4 ($[M-C_4H_8+H]^+$).

c) tert-butyl 7-methyl-5-oxa-2-azaspiro[3.5]nonane-2-carboxylate

In analogy to the experimental procedure of tert-butyl 7-fluoro-5-oxa-2-azaspiro[3.5]nonane-2-carboxylate, tert-butyl 7-methyl-5-oxa-2-azaspiro[3.5]non-7-ene-2-carboxylate instead of tert-butyl 7-fluoro-5-oxa-2-azaspiro[3.5]non-7-ene-2-carboxylate was converted into the title compound (807 mg, 100%) which was obtained as a colourless oil. MS (ESI): 186.5 ($[M-C_4H_8+H]^+$).

d) 7-methyl-5-oxa-2-azaspiro[3.5]nonane hydrochloride

In analogy to the experimental procedure of 7-fluoro-5-oxa-2-azaspiro[3.5]nonane hydrochloride, tert-butyl 7-methyl-5-oxa-2-azaspiro[3.5]nonane-2-carboxylate instead of tert-butyl 7-fluoro-5-oxa-2-azaspiro[3.5]nonane-2-carboxylate was converted into the title compound (592 mg, 100%) which was obtained as a light grey solid. MS (ESI): 142.3 ($[M+H]^+$).

e) (S)-benzyl 7-methyl-5-oxa-2-azaspiro[3.5]nonane-2-carboxylate and (R)-benzyl 7-methyl-5-oxa-2-azaspiro[3.5]nonane-2-carboxylate In analogy to the experimental procedure of (S)-benzyl 7-fluoro-5-oxa-2-azaspiro[3.5]nonane-2-carboxylate, 7-methyl-5-oxa-2-azaspiro[3.5]nonane hydrochloride instead of 7-fluoro-5-oxa-2-azaspiro[3.5]nonane hydrochloride was converted into benzyl 7-methyl-5-oxa-2-azaspiro[3.5]nonane-2-carboxylate. The mixture was separated by chiral SFC (AD-H, 10% Ethanol) affording (+) enantiopure (S)-title compound or enantiomer (8.60 g, 42%) as a yellow oil, MS (ESI): 276.0 ($[M+H]^+$), specific optical rotation: +31.6° (methanol, 0.1 g/1)

(−) enantiopure (R)-title compound or enantiomer (9.01 g, 44%) as a yellow oil, MS (ESI): 276.1 ($[M+H]^+$), specific optical rotation: −36.0° (methanol, 0.1 g/1).

f) (R)-7-methyl-5-oxa-2-azaspiro[3.5]nonane hydrochloride or enantiomer

In analogy to the experimental procedure of (S)-benzyl 7-fluoro-5-oxa-2-azaspiro[3.5]nonane-2-carboxylate, (R)-benzyl 7-methyl-5-oxa-2-azaspiro[3.5]nonane-2-carboxylate or enantiomer was converted into the title compound (5.82 g, 100%) which was obtained as a white solid. MS (ESI): 142.3 ($[M+H]^+$).

2-(azetidin-3-yloxy)-6-(trifluoromethyl)pyrazine hydrochloride

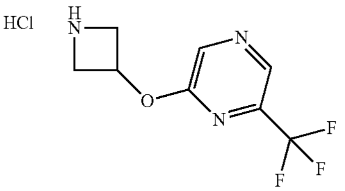 [SMILES: Cl ; FC(F)(F)c1cncc(OC2CNC2)n1]

a) tert-butyl 3-[6-(trifluoromethyl)pyrazin-2-yl]oxyazetidine-1-carboxylate

To a solution of 3-hydroxy-azetidine-1-carboxylic acid tert-butyl ester (500 mg, 2.89 mmol) in 1,4-dioxane (25 mL) was added sodium hydride (60% dispersion in mineral oil, 174 mg, 4.33 mmol) at 0° C. After stirring for 15 minutes, a solution of 2-chloro-6-trifluoromethyl-pyrazine (527 mg, 2.89 mmol) in 1,4-dioxane (5 mL) was added and the reaction mixture was stirred at 50° C. for 45 min. After cooling to room temperature the reaction mixture was quenched by addition of saturated aqueous $NH_4Cl$ and extracted with ethyl acetate (3×20 mL). The combined organic layers were washed with brine, dried ($Na_2SO_4$), filtered and concentrated in vacuo. Purification by flash chromatography (silica, 40% ethyl acetate in hexane) afforded the title compound (660 mg, 71%) as a colorless solid.

b) 2-(azetidin-3-yloxy)-6-(trifluoromethyl)pyrazine hydrochloride

A solution of tert-butyl 3-[6-(trifluoromethyl)pyrazin-2-yl]oxyazetidine-1-carboxylate (650 mg, 2.036 mmol) in hydrochloric acid in 1,4-dioxane (4.0 M, 5 mL) was stirred at room temperature for 5 h. The reaction mixture was concentrated in vacuo to afford the title compound as a light brown solid (380 mg, 73%). MS (ESI): 220.1 ($[M+H]^+$).

| Ex | Name | Structure | MS(ESI) ($[M + H]^+$) | Method | Building block |
|---|---|---|---|---|---|
| 1 | 5-(cis-2,6-dimethylmorpholin-4-yl)-2-((5-methyl-3-(6-methylpyridin-3-yl)triazol-4-yl)methyl)pyridazin-3-one | 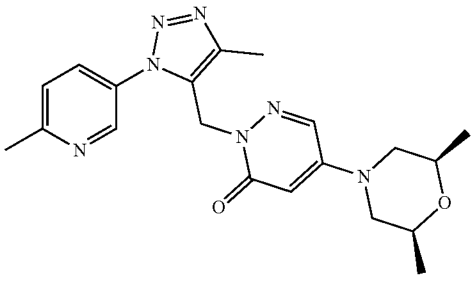 | 395.9 | 2 | C |

-continued

| Ex | Name | Structure | MS(ESI) ([M + H]+) | Method | Building block |
|---|---|---|---|---|---|
| 2 | 5-(cis-2,6-dimethylmorpholin-4-yl)-2-((3-methyl-5-(6-methylpyridin-3-yl)triazol-4-yl)methyl)pyridazin-3-one | 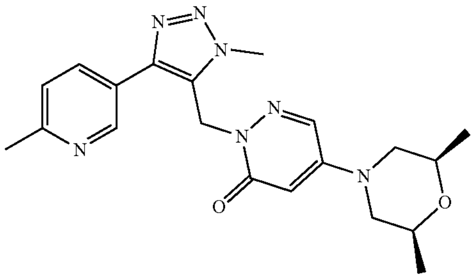 | 395.2 | 2 | D |
| 3 | 2-((5-(4-chloro-2-fluoro-phenyl)-3-methyl-triazol-4-yl)methyl)-5-(cis-2,6-dimethylmorpholin-4-yl)pyridazin-3-one | 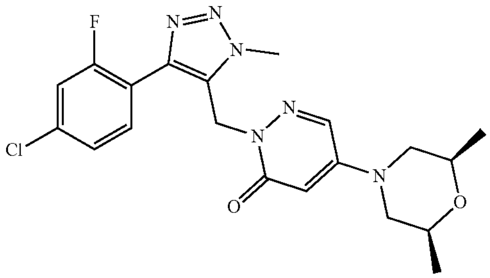 [SMILES: C[C@@H]1CN(c2cnn(Cc3c(-c4ccc(Cl)cc4F)nnn3C)c(=O)c2)C[C@H](C)O1] | 433.3 | 4 | E |
| 4 | 2-((3-(4-chloro-2-fluoro-phenyl)-5-methyl-triazol-4-yl)methyl)-5-morpholino-pyridazin-3-one | 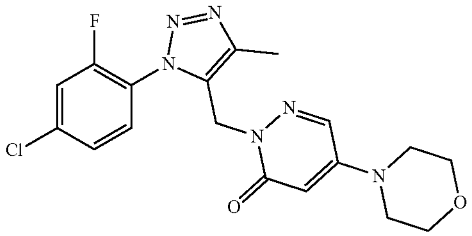 [SMILES: Cc1nnn(-c2ccc(Cl)cc2F)c1Cn1ncc(N2CCOCC2)cc1=O] | 405.2 | 4 | F |
| 5 | 2-((3-(4-chloro-2-fluoro-phenyl)-5-methyl-triazol-4-yl)methyl)-5-(dimethylamino) pyridazin-3-one | 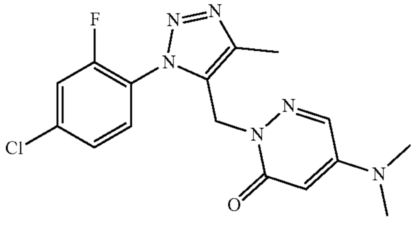 [SMILES: Cc1nnn(-c2ccc(Cl)cc2F)c1Cn1ncc(N(C)C)cc1=O] | 363.3 | 4 | F |
| 6 | 2-((3-(4-chloro-2-fluoro-phenyl)-5-methyl-triazol-4-yl)methyl)-5-(4-(cyclopropane-carbonyl)piperazin-1-yl)pyridazin-3-one | 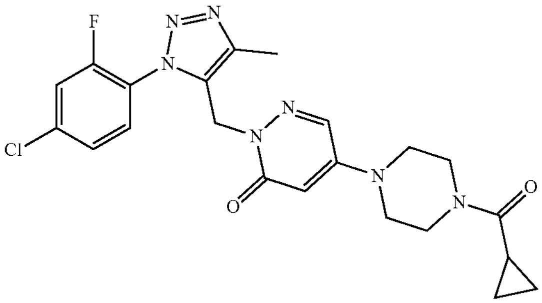 [SMILES: Cc1nnn(-c2ccc(Cl)cc2F)c1Cn1ncc(N2CCN(C(=O)C3CC3)CC2)cc1=O] | 472.0 | 4 | F |

-continued

| Ex | Name | Structure | MS(ESI) ([M + H]+) | Method | Building block |
|---|---|---|---|---|---|
| 7 | 2-((3-(4-chloro-2-fluoro-phenyl)-5-methyl-triazol-4-yl)methyl)-5-((2S,6R)-2,6-dimethylmorpholin-4-yl)pyridazin-3-one | 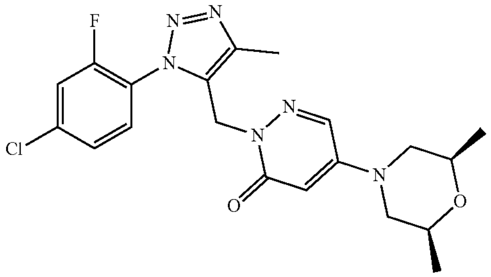 [SMILES: Cc1nnn(-c2ccc(Cl)cc2F)c1Cn1ncc(N2C[C@@H](C)O[C@@H](C)C2)cc1=O] | 433.0 | 4 | F |
| 8 | 2-((3-methyl-5-(6-methyl-3-pyridyl)triazol-4-yl)methyl)-5-pyrrolidin-1-yl-pyridazin-3-one | 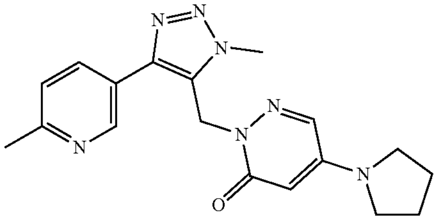 [SMILES: Cc1ccc(-c2nnn(C)c2Cn2ncc(N3CCCC3)cc2=O)cn1] | 352.2 | 6 | D |
| 9 | 2-[[3-methyl-5-(6-methyl-3-pyridyl)triazol-4-yl]methyl]-5-morpholino-pyridazin-3-one | 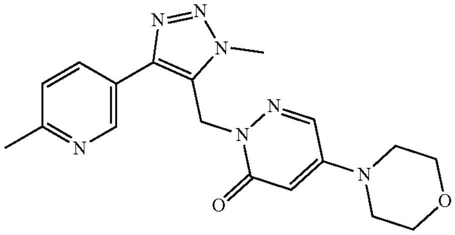 [SMILES: Cc1ccc(-c2nnn(C)c2Cn2ncc(N3CCOCC3)cc2=O)cn1] | 367.9 | 6 | D |
| 10 | 5-(3,3-dimethylpyrrolidin-1-yl)-2-[[3-methyl-5-(6-methyl-3-pyridyl)triazol-4-yl]methyl]pyridazin-3-one | 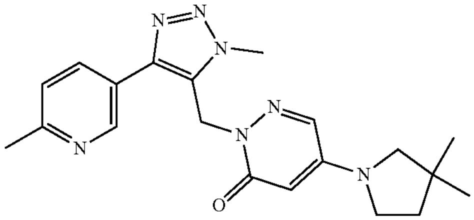 | 380.1 | 6 | D |
| 11 | 5-(2,2-dimethylmorpholin-4-yl)-2-[[3-methyl-5-(6-methyl-3-pyridyl)triazol-4-yl]methyl]pyridazin-3-one | 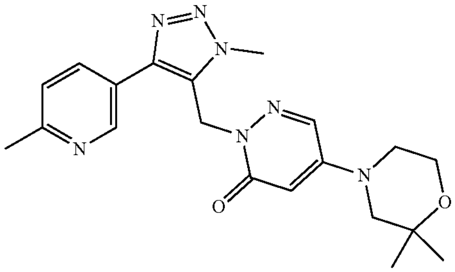 [SMILES: Cc1ccc(-c2nnn(C)c2Cn2ncc(N3CCOC(C)(C)C3)cc2=O)cn1] | 396.1 | 6 | D |
| 12 | 2-[[3-methyl-5-(6-methyl-3-pyridyl)triazol-4-yl]methyl]-5-[rac-(2S,6S)-2,6-dimethylmorpholin-4-yl]pyridazin-3-one | 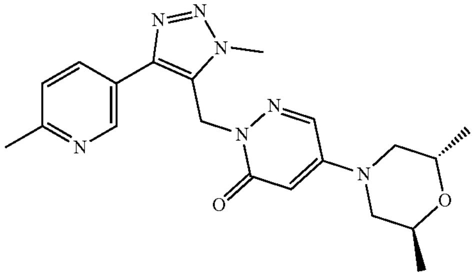 | 396.1 | 6 | D |

-continued

| Ex | Name | Structure | MS(ESI) ([M + H]$^+$) | Method | Building block |
|---|---|---|---|---|---|
| 13 | 2-[[3-(4-chlorophenyl)-5-methyl-triazol-4-yl]methyl]-5-(dimethylamino) pyridazin-3-one | 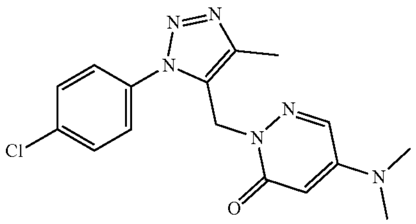 [SMILES: Cc1nnn(-c2ccc(Cl)cc2)c1Cn1ncc(N(C)C)cc1=O] | 345 | 4 | G |
| 14 | 2-[[3-(4-chlorophenyl)-5-methyl-triazol-4-yl]methyl]-5-piperazin-1-yl-pyridazin-3-one | 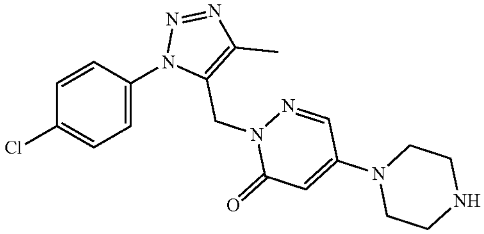 [SMILES: Cc1nnn(-c2ccc(Cl)cc2)c1Cn1ncc(N2CCNCC2)cc1=O] | 386 | 4 | G |
| 15 | 2-[[5-(4-chloro-2-fluoro-phenyl)-3-methyl-triazol-4-yl]methyl]-5-(dimethylamino) pyridazin-3-one | 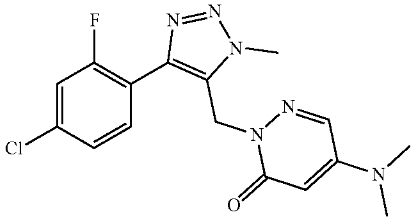 [SMILES: CN(C)c1cnn(Cc2c(-c3ccc(Cl)cc3F)nnn2C)c(=O)c1] | 363.0 | 4 | E |
| 16 | 2-[[5-(4-chloro-2-fluoro-phenyl)-3-methyl-triazol-4-yl]methyl]-5-morpholino-pyridazin-3-one | 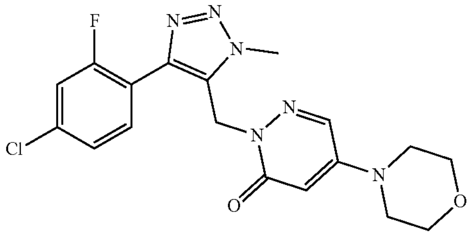 [SMILES: Cn1nnc(-c2ccc(Cl)cc2F)c1Cn1ncc(N2CCOCC2)cc1=O] | 404.9 | 4 | E |
| 17 | 2-[[5-(4-chloro-2-fluoro-phenyl)-3-methyl-triazol-4-yl]methyl]-5-(4-cyclopropyl-piperazin-1-yl)pyridazin-3-one | 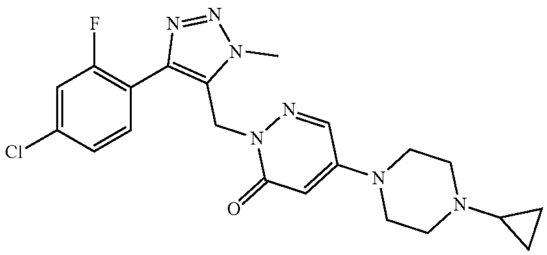 [SMILES: Cn1nnc(-c2ccc(Cl)cc2F)c1Cn1ncc(N2CCN(C3CC3)CC2)cc1=O] | 444.0 | 4 | E |
| 18 | 2-[[3-methyl-5-(6-methyl-3-pyridyl)triazol-4-yl]methyl]-5-[(2R)-2-methylpyrrolidin-1-yl]pyridazin-3-one | 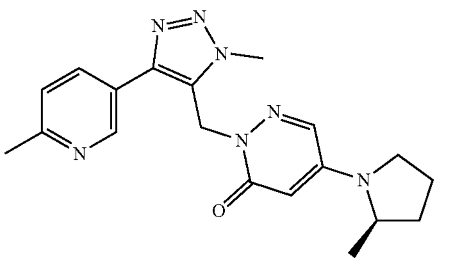 [SMILES: Cc1ccc(-c2nnn(C)c2Cn2ncc(N3CCC[C@H]3C)cc2=O)cn1] | 365.9 | 6 | D |

-continued

| Ex | Name | Structure | MS(ESI) ([M + H]$^+$) | Method | Building block |
|---|---|---|---|---|---|
| 19 | 5-[(2S)-2-(methoxymethyl) pyrrolidin-1-yl]-2-[[3-methyl-5-(6-methyl-3-pyridyl)triazol-4-yl]methyl]pyridazin-3-one | 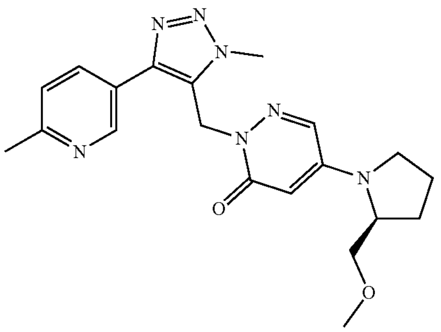 [SMILES: COC[C@@H]1CCCN1c1cnn(Cc2c(-c3ccc(C)nc3)nnn2C)c(=O)c1] | 396.0 | 6 | D |
| 20 | 2-[[3-(4-chlorophenyl)-5-methyl-triazol-4-yl]methyl]-5-[(2R,6S)-2,6-dimethylmorpholin-4-yl]pyridazin-3-one | 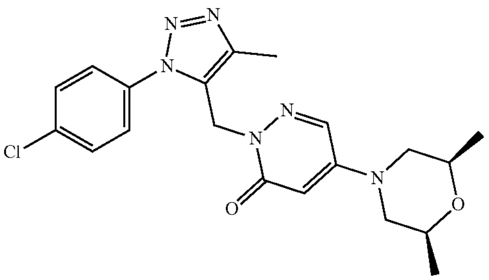 [SMILES: Cc1nnn(-c2ccc(Cl)cc2)c1Cn1ncc(N2C[C@@H](C)O[C@@H](C)C2)cc1=O] | 415 | 4 | G |
| 21 | 2-[[5-(4-chloro-2-fluoro-phenyl)-3-methyl-triazol-4-yl]methyl]-5-[4-(cyclopropanc-carbonyl)piperazin-1-yl]pyridazin-3-one | 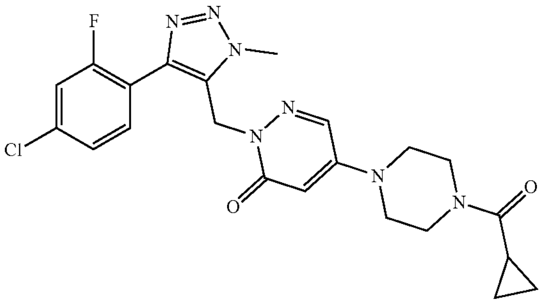 [SMILES: Cn1nnc(-c2ccc(Cl)cc2F)c1Cn1ncc(N2CCN(C(=O)C3CC3)CC2)cc1=O] | 471.9 | 4 | E |
| 22 | 2-[[5-(4-chloro-2-fluoro-phenyl)-3-methyl-triazol-4-yl]methyl]-5-(methylamino) pyridazin-3-one | 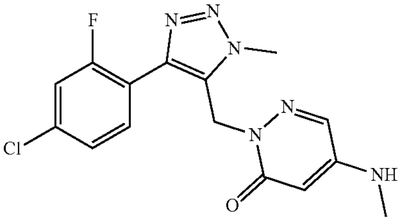 [SMILES: CNc1cnn(Cc2c(-c3ccc(Cl)cc3F)nnn2C)c(=O)c1] | 348.9 | 4 | E |
| 23 | 2-((1-(4-chloro-2-fluorophenyl)-4-methyl-1H-1,2,3-triazol-5-yl)methyl)-5-(3-ethoxyazetidin-1-yl)pyridazin-3(2H)-one | 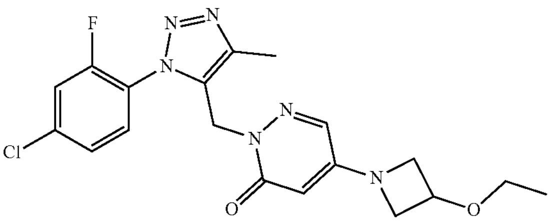 [SMILES: CCOC1CN(c2cnn(Cc3c(C)nnn3-c3ccc(Cl)cc3F)c(=O)c2)C1] | 419.2 | 7 | F |

-continued

| Ex | Name | Structure | MS(ESI) ([M + H]$^+$) | Method | Building block |
|---|---|---|---|---|---|
| 24 | 2-[[3-(4-chloro-2-fluoro-phenyl)-5-methyl-triazol-4-yl]methyl]-5-isoindolin-2-yl-pyridazin-3-one | 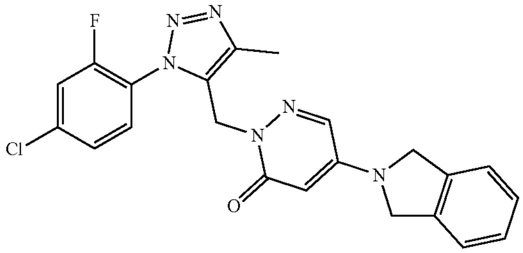 [SMILES: Cc1nnn(-c2ccc(Cl)cc2F)c1Cn1ncc(N2Cc3ccccc3C2)cc1=O] | 437.2 | 7 | F |
| 25 | 2-[[5-methyl-3-(6-methyl-3-pyridyl)triazol-4-yl]methyl]-5-[(2R)-2-methylpyrrolidin-1-yl]pyridazin-3-one | 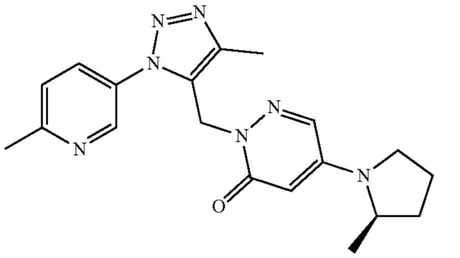 [SMILES: Cc1ccc(-n2nnc(C)c2Cn2ncc(N3CCC[C@H]3C)cc2=O)cn1] | 366.3 | 7 | C |
| 26 | 2-[[5-(4-chloro-2-fluoro-phenyl)-3-methyl-triazol-4-yl]methyl]-5-(3-methoxyazetidin-1-yl)pyridazin-3-one | 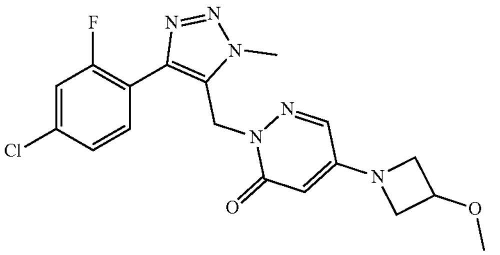 [SMILES: COC1CN(c2cnn(Cc3c(-c4ccc(Cl)cc4F)nnn3C)c(=O)c2)C1] | 405.3 | 1 | E |
| 27 | 2-[[5-(4-chloro-2-fluoro-phenyl)-3-methyl-triazol-4-yl]methyl]-5-(3-ethoxyazetidin-1-yl)pyridazin-3-one | 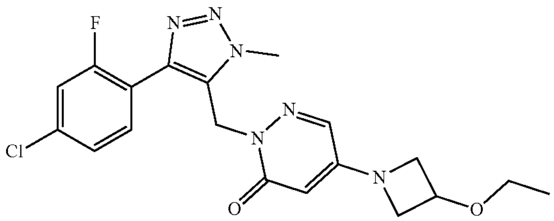 [SMILES: CCOC1CN(c2cnn(Cc3c(-c4ccc(Cl)cc4F)nnn3C)c(=O)c2)C1] | 419.3 | 1 | E |
| 28 | 2-[[5-(4-chloro-2-fluoro-phenyl)-3-methyl-triazol-4-yl]methyl]-5-[3-(cyclopropyl-methoxy)azetidin-1-yl]pyridazin-3-one | 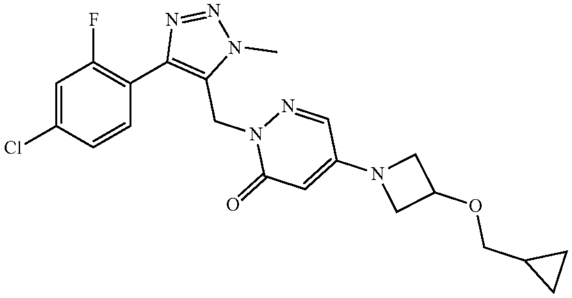 [SMILES: Cn1nnc(-c2ccc(Cl)cc2F)c1Cn1ncc(N2CC(OCC3CC3)C2)cc1=O] | 445.3 | 1 | E |
| 29 | 2-[[5-(4-chloro-2-fluoro-phenyl)-3-methyl-triazol-4-yl]methyl]-5-(5-oxa-2-azaspiro[3.4]octan-2-yl)pyridazin-3-one | 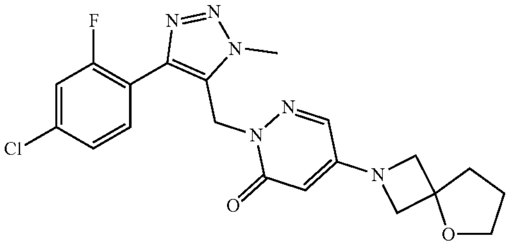 [SMILES: Cn1nnc(-c2ccc(Cl)cc2F)c1Cn1ncc(N2CC3(CCCO3)C2)cc1=O] | 431.3 | 1 | E |

-continued

| Ex | Name | Structure | MS(ESI) ([M + H]+) | Method | Building block |
|---|---|---|---|---|---|
| 30 | 2-[[5-(4-chlorophenyl)-3-methyl-triazol-4-yl]methyl]-5-[(2R,6S)-2,6-dimethylmorpholin-4-yl]pyridazin-3-one | 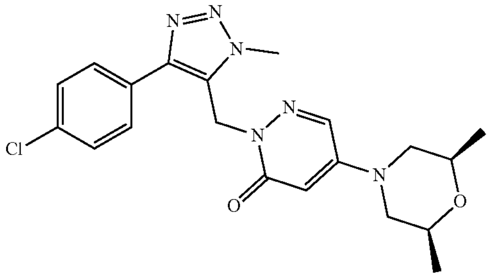 [SMILES: C[C@@H]1CN(c2cnn(Cc3c(-c4ccc(Cl)cc4)nnn3C)c(=O)c2)C[C@H](C)O1] | 414.8 | 4 | H |
| 31 | 2-[[5-(4-chlorophenyl)-3-methyl-triazol-4-yl]methyl]-5-(dimethylamino) pyridazin-3-one | 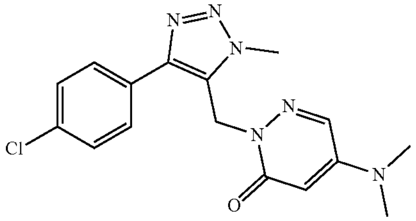 [SMILES: CN(C)c1cnn(Cc2c(-c3ccc(Cl)cc3)nnn2C)c(=O)c1] | 344.9 | 4 | H |
| 32 | (S)-2-((4-(4-chloro-2-fluorophenyl)-1-methyl-1H-1,2,3-triazol-5-yl)methyl)-5-(7-methoxy-5-oxa-2-azaspiro[3.4]octan-2-yl)pyridazin-3(2H)-one | 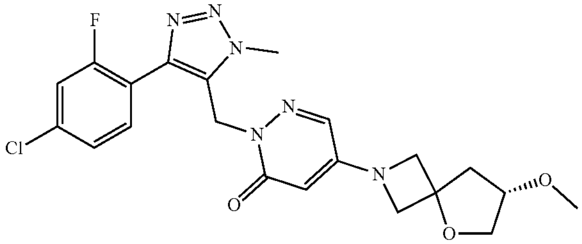 [SMILES: CO[C@@H]1COC2(C1)CN(c1cnn(Cc3c(-c4ccc(Cl)cc4F)nnn3C)c(=O)c1)C2] | 461.3 | 1 | E |
| 33 | (R)-2-((4-(4-chloro-2-fluorophenyl)-1-methyl-1H-1,2,3-triazol-5-yl)methyl)-5-(7-methoxy-5-oxa-2-azaspiro[3.4]octan-2-yl)pyridazin-3(2H)-one | 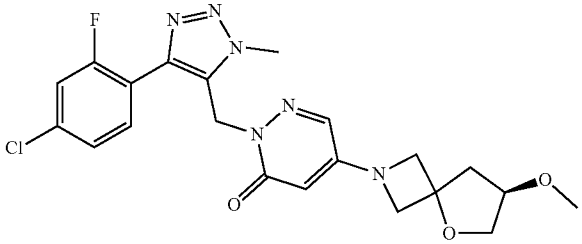 [SMILES: CO[C@H]1COC2(C1)CN(c1cnn(Cc3c(-c4ccc(Cl)cc4F)nnn3C)c(=O)c1)C2] | 461.3 | 1 | E |
| 34 | 2-[[3-(4-chloro-2-fluoro-phenyl)-5-methyl-triazol-4-yl]methyl]-5-[3-(2,2,2-trifluoro-ethoxy)azetidin-1-yl]pyridazin-3-one | 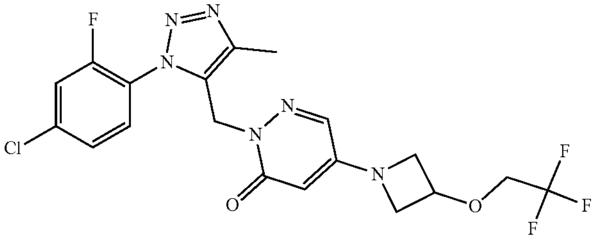 [SMILES: Cc1nnn(-c2ccc(Cl)cc2F)c1Cn1ncc(N2CC(OCC(F)(F)F)C2)cc1=O] | 473.5 | 4 | F |
| 35 | 2-[[3-(4-chloro-2-fluoro-phenyl)-5-methyl-triazol-4-yl]methyl]-5-[(2S)-2-methylmorpholin-4-yl]pyridazin-3-one | 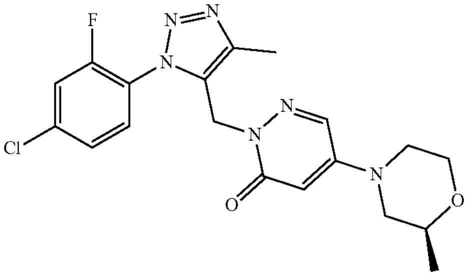 [SMILES: Cc1nnn(-c2ccc(Cl)cc2F)c1Cn1ncc(N2CCO[C@@H](C)C2)cc1=O] | 419.4 | 4 | F |

-continued

| Ex | Name | Structure | MS(ESI) ([M + H]+) | Method | Building block |
|---|---|---|---|---|---|
| 36 | 2-[[3-(4-chloro-2-fluoro-phenyl)-5-methyl-triazol-4-yl]methyl]-5-[(2R)-2-methylmorpholin-4-yl]pyridazin-3-one | 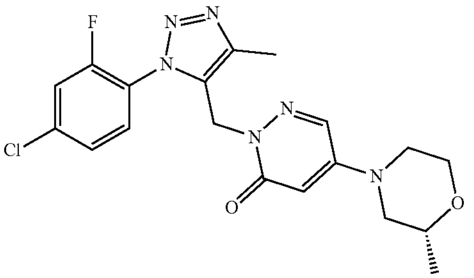 [SMILES: Cc1nnn(-c2ccc(Cl)cc2F)c1Cn1ncc(N2CCO[C@H](C)C2)cc1=O] | 419.4 | 4 | F |
| 37 | 2-[[3-(4-chloro-2-fluoro-phenyl)-5-methyl-triazol-4-yl]methyl]-5-[rac-(2S,6S)-2,6-dimethylmorpholin-4-yl]pyridazin-3-one | 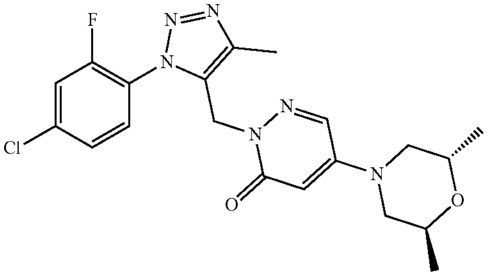 [SMILES: Cc1nnn(-c2ccc(Cl)cc2F)c1Cn1ncc(N2C[C@H](C)O[C@@H](C)C2)cc1=O] | 433.3 | 4 | F |
| 38 | 2-[[3-(4-chloro-2-fluoro-phenyl)-5-methyl-triazol-4-yl]methyl]-5-[4-(2-methylimidazol-1-yl)-1-piperidyl]pyridazin-3-one | 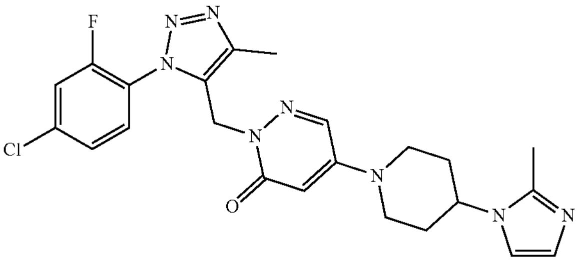 [SMILES: Cc1nnn(-c2ccc(Cl)cc2F)c1Cn1ncc(N2CCC(n3ccnc3C)CC2)cc1=O] | 483.1 | 4 | F |
| 39 | 2-[[3-(4-chloro-2-fluoro-phenyl)-5-methyl-triazol-4-yl]methyl]-5-[4-(2-methoxy-3-pyridyl)piperazin-1-yl]pyridazin-3-one | 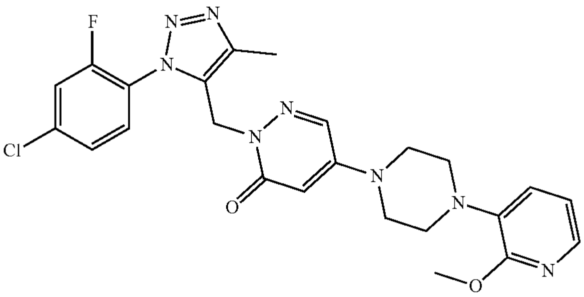 [SMILES: COc1ncccc1N1CCN(c2cnn(Cc3c(C)nnn3-c3ccc(Cl)cc3F)c(=O)c2)CC1] | 511.5 | 4 | F |
| 40 | 2-[[5-(4-chlorophenyl)-3-methyl-triazol-4-yl]methyl]-5-[(3S)-4-isopropyl-3-methyl-piperazin-1-yl]pyridazin-3-one | 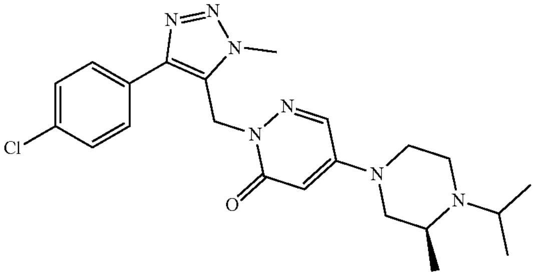 [SMILES: CC(C)N1CCN(c2cnn(Cc3c(-c4ccc(Cl)cc4)nnn3C)c(=O)c2)C[C@@H]1C] | 442.1 | 4 | H |

-continued

| Ex | Name | Structure | MS(ESI) ([M + H]+) | Method | Building block |
|---|---|---|---|---|---|
| 41 | 2-[[5-(4-chlorophenyl)-3-methyl-triazol-4-yl]methyl]-5-(3-ethoxyazetidin-1-yl)pyridazin-3-one | 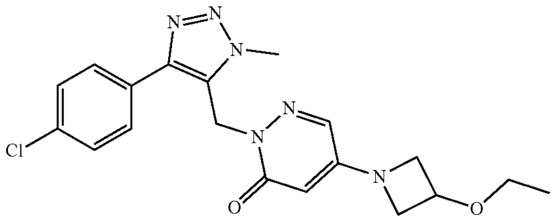 [SMILES: CCOC1CN(c2cnn(Cc3c(-c4ccc(Cl)cc4)nnn3C)c(=O)c2)C1] | 401.1 | 4 | H |
| 42 | 2-((5-(4-chloro-2-fluoro-phenyl)-3-methyl-triazol-4-yl)methyl)-5-((3R)-3-isopropoxy-pyrrolidin-1-yl)pyridazin-3-one | 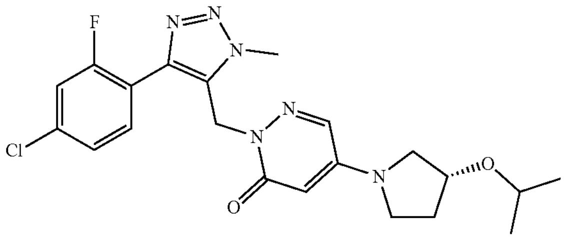 [SMILES: CC(C)O[C@@H]1CCN(c2cnn(Cc3c(-c4ccc(Cl)cc4F)nnn3C)c(=O)c2)C1] | 447.0 | 4 | E |
| 43 | 2-((5-(4-chloro-2-fluoro-phenyl)-3-methyl-triazol-4-yl)methyl)-5-(3-(2-pyridyl-oxy)azetidin-1-yl)pyridazin-3-one | 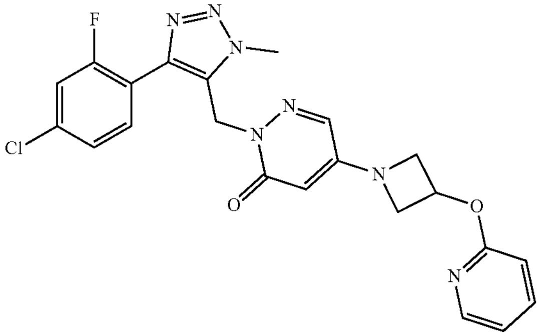 [SMILES: Cn1nnc(-c2ccc(Cl)cc2F)c1Cn1ncc(N2CC(Oc3ccccn3)C2)cc1=O] | 468.0 | 4 | E |
| 44 | 2-((5-(4-chloro-2-fluoro-phenyl)-3-methyl-triazol-4-yl)methyl)-5-((3S)-4-isopropyl-3-methyl-piperazin-1-yl)pyridazin-3-one | 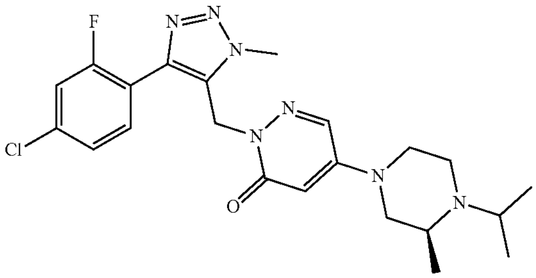 [SMILES: CC(C)N1CCN(c2cnn(Cc3c(-c4ccc(Cl)cc4F)nnn3C)c(=O)c2)C[C@@H]1C] | 460.1 | 4 | E |
| 45 | 2-((5-(4-chloro-2-fluoro-phenyl)-3-methyl-triazol-4-yl)methyl)-5-((2S)-2-methylmorpholin-4-yl)pyridazin-3-one | 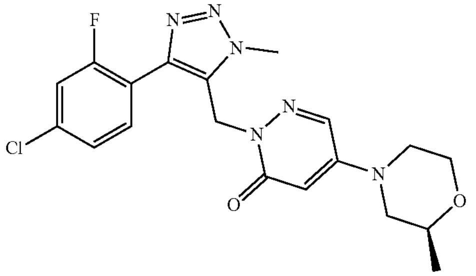 [SMILES: C[C@H]1CN(c2cnn(Cc3c(-c4ccc(Cl)cc4F)nnn3C)c(=O)c2)CCO1] | 419.1 | 4 | E |

-continued

| Ex | Name | Structure | MS(ESI) ([M + H]+) | Method | Building block |
|---|---|---|---|---|---|
| 46 | 2-((5-(4-chloro-2-fluoro-phenyl)-3-methyl-triazol-4-yl)methyl)-5-((2R)-2-methylmorpholin-4-yl)pyridazin-3-one | 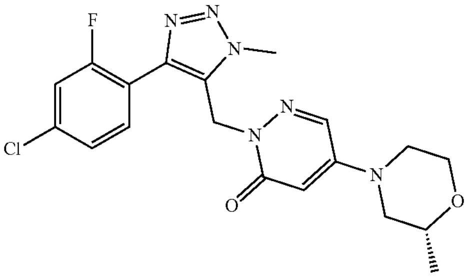 [SMILES: C[C@@H]1CN(c2cnn(Cc3c(-c4ccc(Cl)cc4F)nnn3C)c(=O)c2)CCO1] | 419.1 | 4 | E |
| 47 | 2-[[3-(4-chloro-2-fluoro-phenyl)-5-methyl-triazol-4-yl]methyl]-5-[4-(2-ethylimidazol-1-yl)-1-piperidyl]pyridazin-3-one | 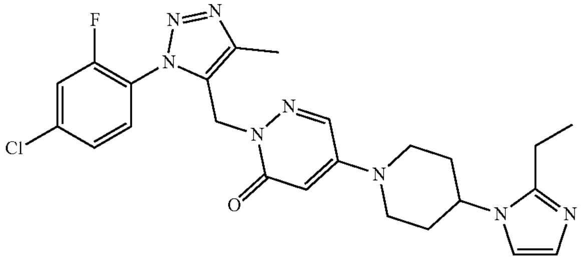 [SMILES: CCc1nccn1C1CCN(c2cnn(Cc3c(C)nnn3-c3ccc(Cl)cc3F)c(=O)c2)CC1] | 497.1 | 4 | F |
| 48 | 2-((5-(4-chloro-2-fluoro-phenyl)-3-methyl-triazol-4-yl)methyl)-5-(3-isopropoxyazetidin-1-yl)pyridazin-3-one | 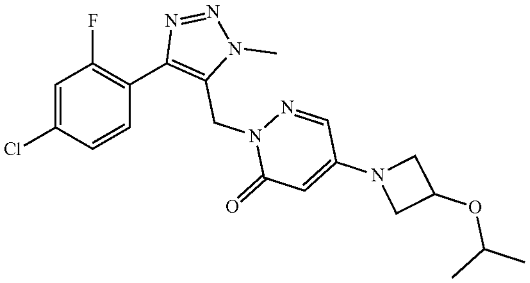 [SMILES: CC(C)OC1CN(c2cnn(Cc3c(-c4ccc(Cl)cc4F)nnn3C)c(=O)c2)C1] | 433.2 | 4 | E |
| 49 | 2-((5-(4-chloro-2-fluoro-phenyl)-3-methyl-triazol-4-yl)methyl)-5-(3-(cyclobutoxy) azetidin-1-yl)pyridazin-3-one | 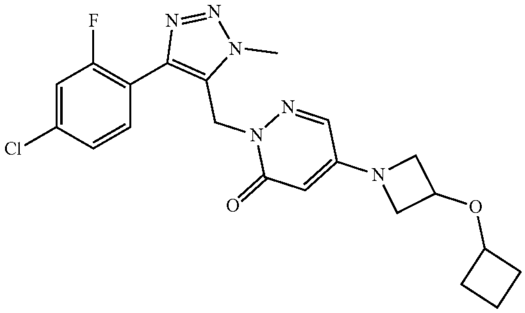 [SMILES: Cn1nnc(-c2ccc(Cl)cc2F)c1Cn1ncc(N2CC(OC3CCC3)C2)cc1=O] | 445.2 | 4 | E |
| 50 | 2-((5-(4-chloro-2-fluoro-phenyl)-3-methyl-triazol-4-yl)methyl)-5-(3-(2,2,2-trifluoro-ethoxy)azetidin-1-yl)pyridazin-3-one | 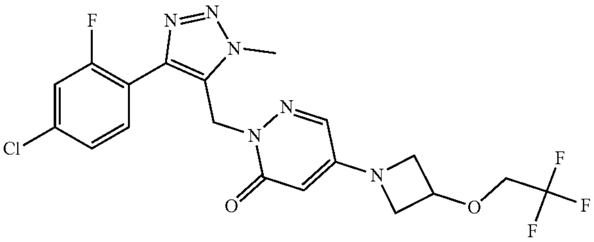 [SMILES: Cn1nnc(-c2ccc(Cl)cc2F)c1Cn1ncc(N2CC(OCC(F)(F)F)C2)cc1=O] | 473.2 | 4 | E |

-continued

| Ex | Name | Structure | MS(ESI) ([M + H]+) | Method | Building block |
|---|---|---|---|---|---|
| 51 | 2-((5-(4-chloro-2-fluoro-phenyl)-3-methyl-triazol-4-yl)methyl)-5-(3-propoxyazetidin-1-yl)pyridazin-3-one | 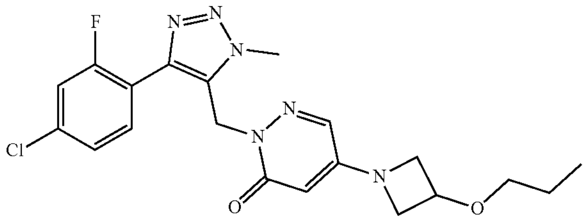 [SMILES: CCCOC1CN(c2cnn(Cc3c(-c4ccc(Cl)cc4F)nnn3C)c(=O)c2)C1] | 433.1 | 4 | E |
| 52 | 2-[[5-(4-chloro-2-fluoro-phenyl)-3-methyl-triazol-4-yl]methyl]-5-[3-[(6-chloro-3-pyridyl)oxy] azetidin-1-yl]pyridazin-3-one | 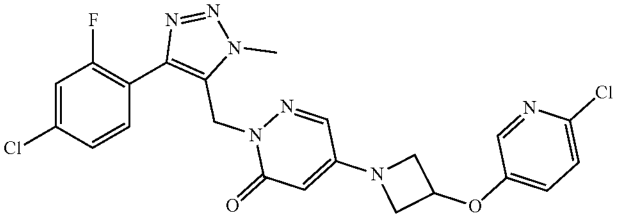 [SMILES: Cn1nnc(-c2ccc(Cl)cc2F)c1Cn1ncc(N2CC(Oc3ccc(Cl)nc3)C2)cc1=O] | 502.0 | 4 | E |
| 53 | 2-((5-(4-chloro-2-fluoro-phenyl)-3-methyl-triazol-4-yl)methyl)-5-(3-(difluoromethoxy) azetidin-1-yl)pyridazin-3-one | 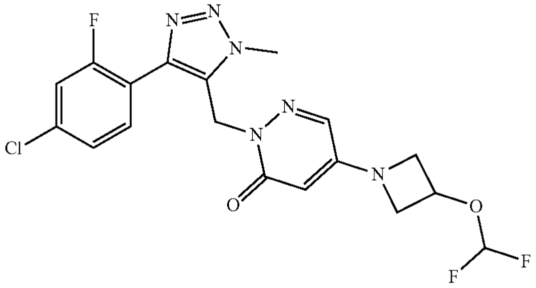 [SMILES: Cn1nnc(-c2ccc(Cl)cc2F)c1Cn1ncc(N2CC(OC(F)F)C2)cc1=O] | 441.0 | 4 | E |
| 54 | 2-[[5-(4-chloro-2-fluoro-phenyl)-3-methyl-triazol-4-yl]methyl]-5-[3-(2,2-difluoro-ethoxy)azetidin-1-yl]pyridazin-3-one | 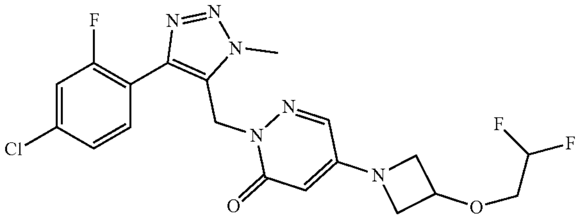 [SMILES: Cn1nnc(-c2ccc(Cl)cc2F)c1Cn1ncc(N2CC(OCC(F)F)C2)cc1=O] | 455.3 | 4 | E |
| 55 | 2-[[5-(4-chloro-2-fluoro-phenyl)-3-methyl-triazol-4-yl]methyl]-5-[3-[(2-chloro-4-pyridyl)oxy] azetidin-1-yl]pyridazin-3-one | 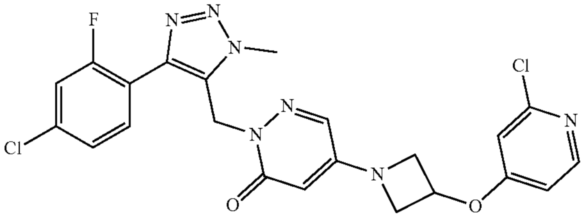 [SMILES: Cn1nnc(-c2ccc(Cl)cc2F)c1Cn1ncc(N2CC(Oc3ccnc(Cl)c3)C2)cc1=O] | 502.0 | 4 | E |
| 56 | 2-((3-(4-chloro-2-fluoro-phenyl)-5-methyl-triazol-4-yl)methyl)-5-(4-methoxyphenyl) pyridazin-3-one | 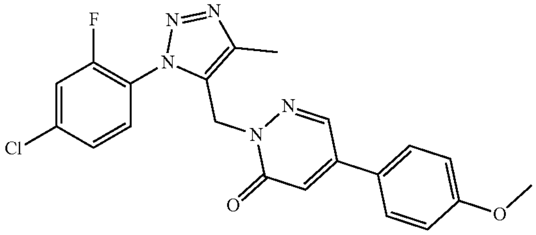 [SMILES: COc1ccc(-c2cnn(Cc3c(C)nnn3-c3ccc(Cl)cc3F)c(=O)c2)cc1] | 426.1 | 10 | F |

-continued

| Ex | Name | Structure | MS(ESI) ([M + H]+) | Method | Building block |
|---|---|---|---|---|---|
| 57 | 2-((3-(4-chloro-2-fluoro-phenyl)-5-methyl-triazol-4-yl)methyl)-5-(2-(trifluoromethyl)-4-pyridyl)pyridazin-3-one | 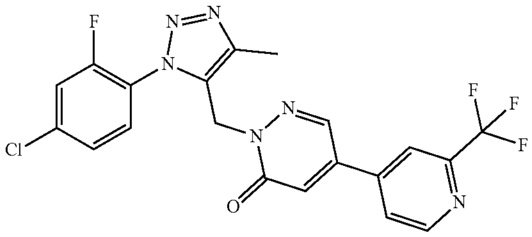 [SMILES: Cc1nnn(-c2ccc(Cl)cc2F)c1Cn1ncc(-c2ccnc(C(F)(F)F)c2)cc1=O] | 465.1 | 10 | F |
| 58 | 2-[[5-(2,4-difluorophenyl)-3-methyl-triazol-4-yl]methyl]-5-[(2R,6S)-2,6-dimethylmorpholin-4-yl]pyridazin-3-one | 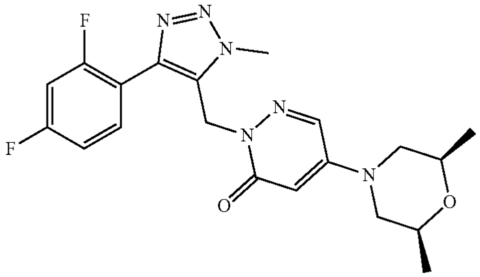 [SMILES: C[C@@H]1CN(c2cnn(Cc3c(-c4ccc(F)cc4F)nnn3C)c(=O)c2)C[C@H](C)O1] | 417.1 | 8 | I |
| 59 | 2-[[5-(4-chlorophenyl)-3-methyl-triazol-4-yl]methyl]-5-[3-(2,2,2-trifluoro-ethoxy)azetidin-1-yl]pyridazin-3-one | 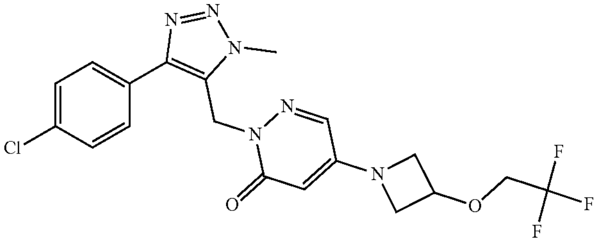 [SMILES: Cn1nnc(-c2ccc(Cl)cc2)c1Cn1ncc(N2CC(OCC(F)(F)F)C2)cc1=O] | 455.1 | 4 | H |
| 60 | 2-[[5-(4-chlorophenyl)-3-methyl-triazol-4-yl]methyl]-5-[3-(2,2-difluoro-ethoxy)azetidin-1-yl]pyridazin-3-one | 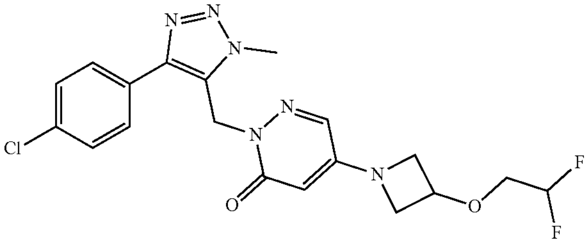 [SMILES: Cn1nnc(-c2ccc(Cl)cc2)c1Cn1ncc(N2CC(OCC(F)F)C2)cc1=O] | 437.1 | 4 | H |
| 61 | 2-((5-(4-chloro-2-fluoro-phenyl)-3-methyl-triazol-4-yl)methyl)-5-(4-methoxyphenyl)pyridazin-3-one | 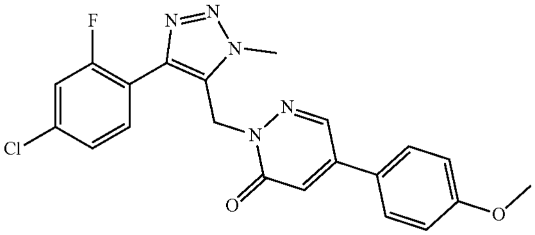 [SMILES: COc1ccc(-c2cnn(Cc3c(-c4ccc(Cl)cc4F)nnn3C)c(=O)c2)cc1] | 426.1 | 10 | E |
| 62 | 2-((5-(4-chloro-2-fluoro-phenyl)-3-methyl-triazol-4-yl)methyl)-5-(6-methoxy-3-pyridyl)pyridazin-3-one | 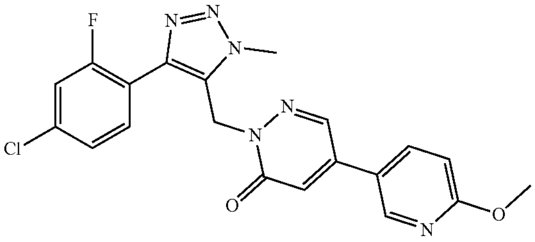 [SMILES: COc1ccc(-c2cnn(Cc3c(-c4ccc(Cl)cc4F)nnn3C)c(=O)c2)cn1] | 427.0 | 10 | E |

-continued

| Ex | Name | Structure | MS(ESI) ([M + H]+) | Method | Building block |
|---|---|---|---|---|---|
| 63 | 2-((5-(4-chloro-2-fluoro-phenyl)-3-methyl-triazol-4-yl)methyl)-5-(2-methoxy-4-pyridyl)pyridazin-3-one | 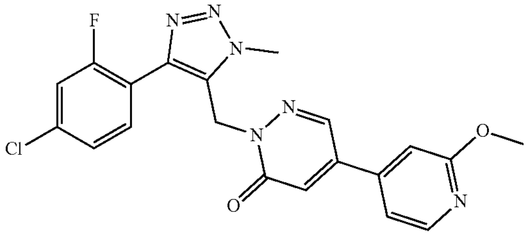 [SMILES: COc1cc(-c2cnn(Cc3c(-c4ccc(Cl)cc4F)nnn3C)c(=O)c2)ccn1] | 427.0 | 10 | E |
| 64 | 2-((5-(4-chloro-2-fluoro-phenyl)-3-methyl-triazol-4-yl)methyl)-5-(1-methylpyrazol-4-yl)pyridazin-3-one | 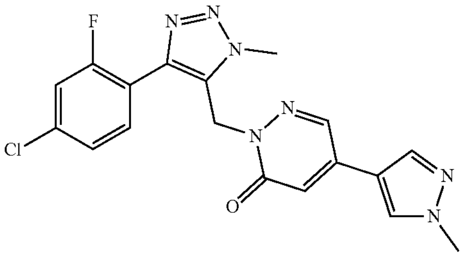 [SMILES: Cn1cc(-c2cnn(Cc3c(-c4ccc(Cl)cc4F)nnn3C)c(=O)c2)cn1] | 400.0 | 10 | E |
| 65 | 2-((3-(4-chloro-2-fluoro-phenyl)-5-methyl-triazol-4-yl)methyl)-5-(1-cyclopropylpyrazol-4-yl)pyridazin-3-one | 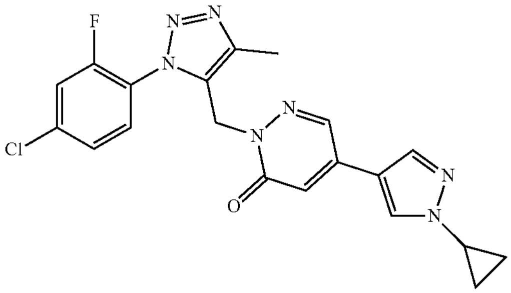 [SMILES: Cc1nnn(-c2ccc(Cl)cc2F)c1Cn1ncc(-c2cnn(C3CC3)c2)cc1=O] | 426.1 | 10 | F |
| 66 | 2-((5-(4-chloro-2-fluoro-phenyl)-3-methyl-triazol-4-yl)methyl)-5-(6-ethoxy-5-methyl-3-pyridyl)pyridazin-3-one | 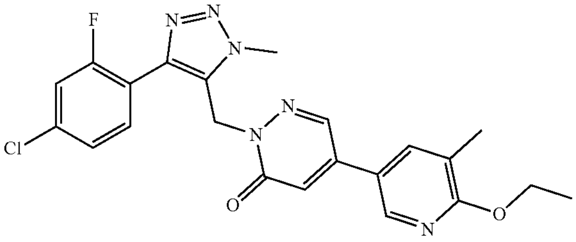 [SMILES: CCOc1ncc(-c2cnn(Cc3c(-c4ccc(Cl)cc4F)nnn3C)c(=O)c2)cc1C] | 455.1 | 10 | E |
| 67 | 2-((5-(4-chloro-2-fluoro-phenyl)-3-methyl-triazol-4-yl)methyl)-5-(1-cyclopropylpyrazol-4-yl)pyridazin-3-one | 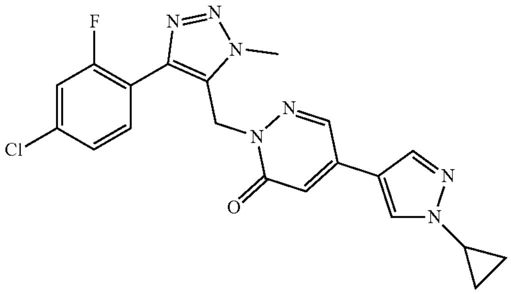 [SMILES: Cn1nnc(-c2ccc(Cl)cc2F)c1Cn1ncc(-c2cnn(C3CC3)c2)cc1=O] | 426.1 | 10 | E |

-continued

| Ex | Name | Structure | MS(ESI) ([M + H]+) | Method | Building block |
|---|---|---|---|---|---|
| 68 | 2-((3-(4-chloro-2-fluoro-phenyl)-5-methyl-triazol-4-yl)methyl)-5-(5-chloro-6-methoxy-3-pyridyl)pyridazin-3-one | 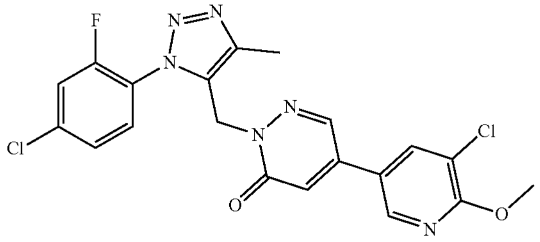 [SMILES: COc1ncc(-c2cnn(Cc3c(C)nnn3-c3ccc(Cl)cc3F)c(=O)c2)cc1Cl] | 461.0 | 10 | F |
| 69 | 2-((5-(4-chloro-2-fluoro-phenyl)-3-methyl-triazol-4-yl)methyl)-5-(5-chloro-6-methoxy-3-pyridyl)pyridazin-3-one | 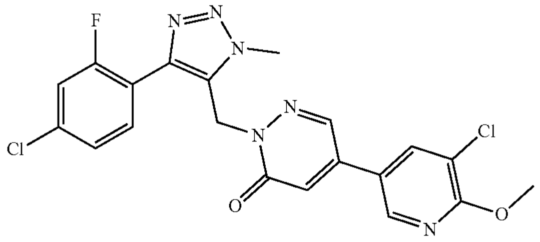 [SMILES: COc1ncc(-c2cnn(Cc3c(-c4ccc(Cl)cc4F)nnn3C)c(=O)c2)cc1Cl] | 461.0 | 10 | E |
| 70 | 2-[[5-[2-fluoro-4-(trifluoromethyl)phenyl]-3-methyl-triazol-4-yl]methyl]-5-(3-isopropoxyazetidin-1-yl)pyridazin-3-one | 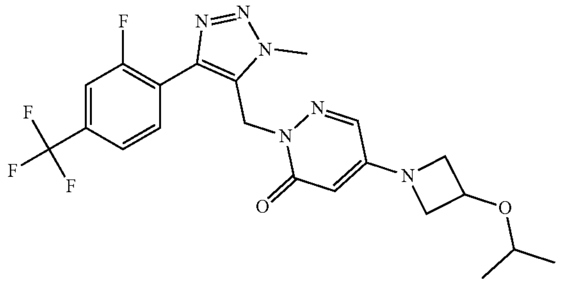 [SMILES: CC(C)OC1CN(c2cnn(Cc3c(-c4ccc(C(F)(F)F)cc4F)nnn3C)c(=O)c2)C1] | 467.1 | 8 | J |
| 71 | 5-[3-(difluoromethoxy)azetidin-1-yl]-2-[[5-[2-fluoro-4-(trifluoromethyl)phenyl]-3-methyl-triazol-4-yl]methyl]pyridazin-3-one | 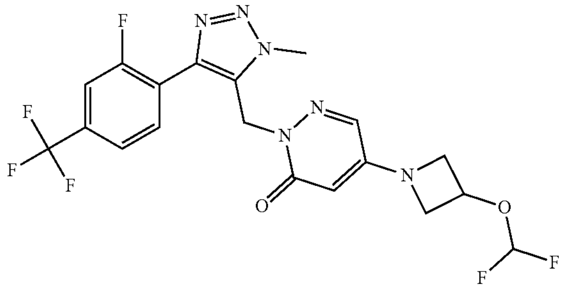 [SMILES: Cn1nnc(-c2ccc(C(F)(F)F)cc2F)c1Cn1ncc(N2CC(OC(F)F)C2)cc1=O] | 475.1 | 8 | J |
| 72 | 5-(3-ethoxyazetidin-1-yl)-2-[[5-[2-fluoro-4-(trifluoromethyl)phenyl]-3-methyl-triazol-4-yl]methyl]pyridazin-3-one | 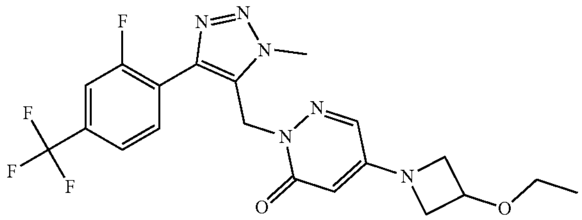 [SMILES: CCOC1CN(c2cnn(Cc3c(-c4ccc(C(F)(F)F)cc4F)nnn3C)c(=O)c2)C1] | 453.1 | 8 | J |
| 73 | 2-[[5-(4-chloro-2-fluoro-phenyl)-3-methyl-triazol-4-yl]methyl]-5-(3-pyrazin-2-yloxyazetidin-1-yl)pyridazin-3-one | 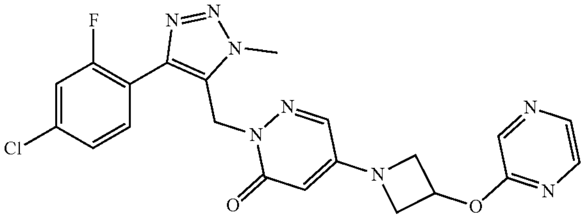 [SMILES: Cn1nnc(-c2ccc(Cl)cc2F)c1Cn1ncc(N2CC(Oc3cnccn3)C2)cc1=O] | 469.1 | 4 | E |

-continued

| Ex | Name | Structure | MS(ESI) ([M + H]+) | Method | Building block |
|---|---|---|---|---|---|
| 74 | 2-[[5-[2-fluoro-4-(trifluoromethyl)phenyl]-3-methyl-triazol-4-yl]methyl]-5-[3-(2,2,2-trifluoro-ethoxy)azetidin-1-yl]pyridazin-3-one | 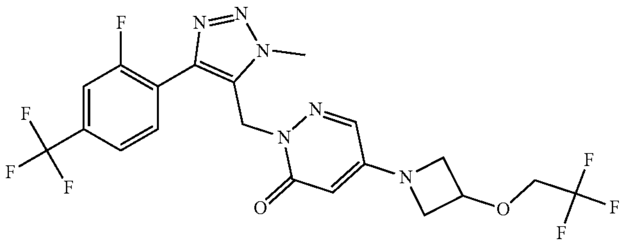 [SMILES: Cn1nnc(-c2ccc(C(F)(F)F)cc2F)c1Cn1ncc(N2CC(OCC(F)(F)F)C2)cc1=O] | 507.1 | 8 | J |
| 75 | 2-[[5-[2-fluoro-4-(trifluoromethyl)phenyl]-3-methyl-triazol-4-yl]methyl]-5-(5-oxa-2-azaspiro[3.4]octan-2-yl)pyridazin-3-one | 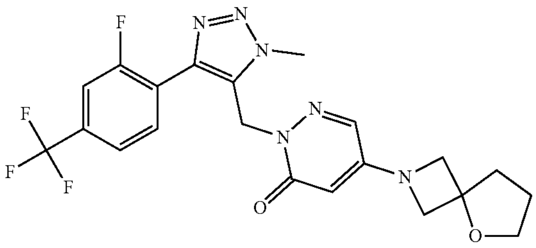 [SMILES: Cn1nnc(-c2ccc(C(F)(F)F)cc2F)c1Cn1ncc(N2CC3(CCCO3)C2)cc1=O] | 465.1 | 8 | J |
| 76 | 5-[3-(2,2-difluoroethoxy)azetidin-1-yl]-2-[[5-[2-fluoro-4-(trifluoromethyl)phenyl]-3-methyl-triazol-4-yl]methyl]pyridazin-3-one | 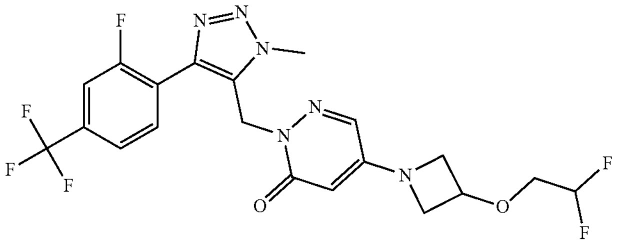 [SMILES: Cn1nnc(-c2ccc(C(F)(F)F)cc2F)c1Cn1ncc(N2CC(OCC(F)F)C2)cc1=O] | 489.1 | 8 | J |
| 77 | 5-[3-(cyclo-butoxy)azetidin-1-yl]-2-[[5-[2-fluoro-4-(trifluoro-methyl)phenyl]-3-methyl-triazol-4-yl]methyl]pyridazin-3-one | 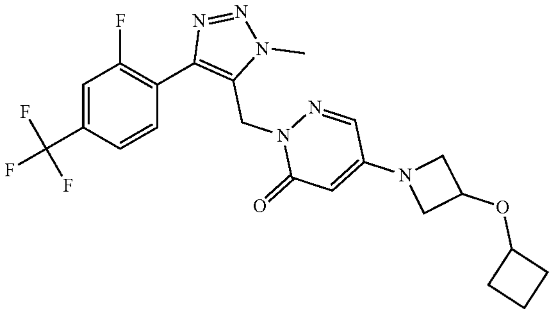 [SMILES: Cn1nnc(-c2ccc(C(F)(F)F)cc2F)c1Cn1ncc(N2CC(OC3CCC3)C2)cc1=O] | 479.1 | 8 | J |
| 78 | 2-[[5-(4-chloro-2-fluoro-phenyl)-3-methyl-triazol-4-yl]methyl]-5-(3-pyrimidin-4-yloxyazetidin-1-yl)pyridazin-3-one | 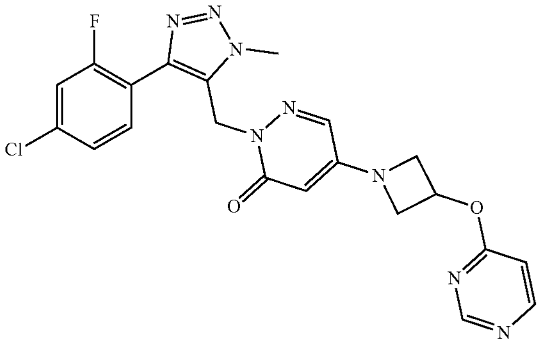 [SMILES: Cn1nnc(-c2ccc(Cl)cc2F)c1Cn1ncc(N2CC(Oc3ccncn3)C2)cc1=O] | 469.1 | 4 | E |

-continued

| Ex | Name | Structure | MS(ESI) ([M + H]+) | Method | Building block |
|---|---|---|---|---|---|
| 79 | 2-((5-(4-chloro-2-fluoro-phenyl)-3-methyl-triazol-4-yl)methyl)-5-(3-pyridazin-3-yloxyazetidin-1-yl)pyridazin-3-one | 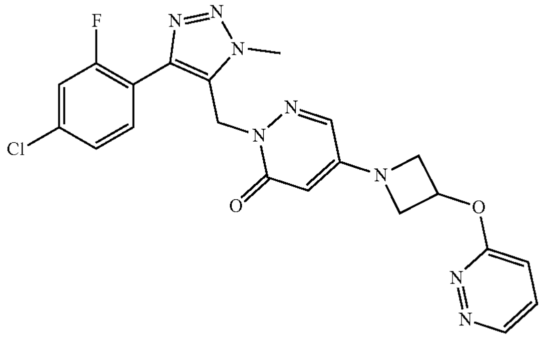 [SMILES: Cn1nnc(-c2ccc(Cl)cc2F)c1Cn1ncc(N2CC(Oc3cccnn3)C2)cc1=O] | 469.1 | 4 | E |
| 80 | 2-[[5-(4-chloro-2-fluoro-phenyl)-3-methyl-triazol-4-yl]methyl]-5-[3-[(5-chloro-2-pyridyl)oxy] azetidin-1-yl]pyridazin-3-one | 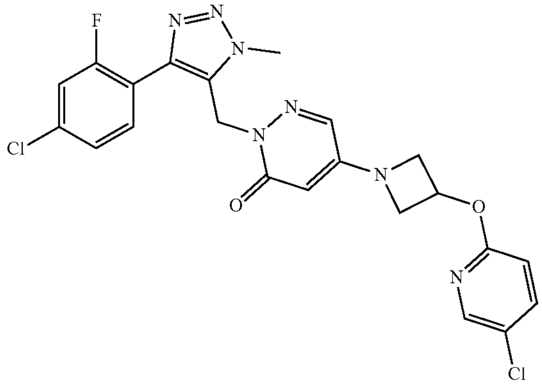 [SMILES: Cn1nnc(-c2ccc(Cl)cc2F)c1Cn1ncc(N2CC(Oc3ccc(Cl)cn3)C2)cc1=O] | 502.1 | 9 | E |
| 81 | 5-(2-methoxy-4-pyridyl)-2-((3-methyl-5-(6-methyl-3-pyridyl)triazol-4-yl)methyl)pyridazin-3-one | 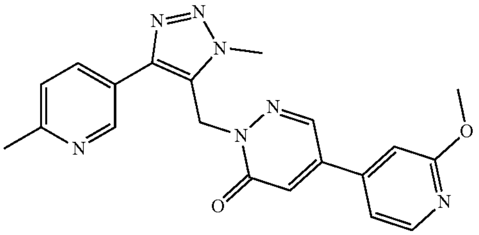 [SMILES: COc1cc(-c2cnn(Cc3c(-c4ccc(C)nc4)nnn3C)c(=O)c2)ccn1] | 390.2 | 10 | D |
| 82 | 5-(5-chloro-6-methoxy-3-pyridyl)-2-((3-methyl-5-(6-methyl-3-pyridyl)triazol-4-yl)methyl)pyridazin-3-one | 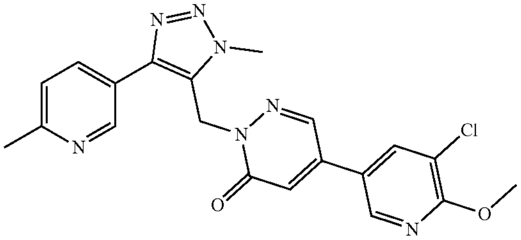 | 424.1 | 10 | D |
| 83 | 2-[[5-[2-fluoro-4-(trifluoromethyl) phenyl]-3-methyl-triazol-4-yl]methyl]-5-(3-pyridazin-3-yloxyazetidin-1-yl)pyridazin-3-one | 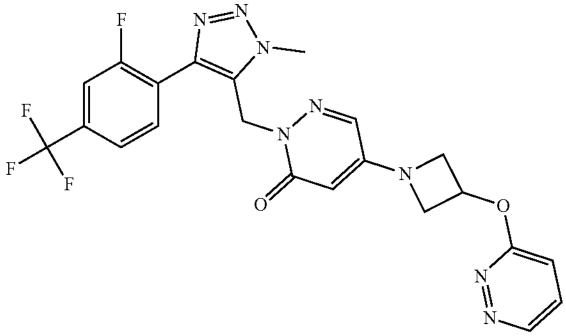 [SMILES: Cn1nnc(-c2ccc(C(F)(F)F)cc2F)c1Cn1ncc(N2CC(Oc3cccnn3)C2)cc1=O] | 503.2 | 8 | J |

-continued

| Ex | Name | Structure | MS(ESI) ([M + H]+) | Method | Building block |
|---|---|---|---|---|---|
| 84 | 2-[[5-[2-fluoro-4-(trifluoromethyl)phenyl]-3-methyl-triazol-4-yl]methyl]-5-[3-(2-pyridyloxy)azetidin-1-yl]pyridazin-3-one | 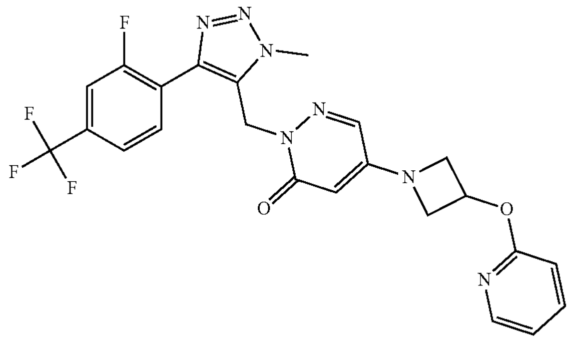 [SMILES: Cn1nnc(-c2ccc(C(F)(F)F)cc2F)c1Cn1ncc(N2CC(Oc3ccccn3)C2)cc1=O] | 502.1 | 8 | J |
| 85 | 2-[[5-(4-chloro-2-fluoro-phenyl)-3-ethyl-triazol-4-yl]methyl]-5-[3-(cyclobutoxy)azetidin-1-yl]pyridazin-3-one | 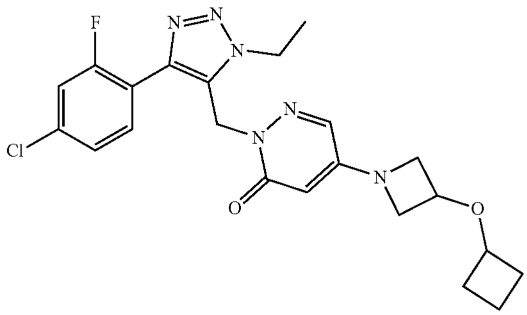 [SMILES: CCn1nnc(-c2ccc(Cl)cc2F)c1Cn1ncc(N2CC(OC3CCC3)C2)cc1=O] | 459.1 | 8 | K |
| 86 | 2-[[5-(4-chloro-2-fluoro-phenyl)-3-ethyl-triazol-4-yl]methyl]-5-[3-(2,2-difluoro-ethoxy)azetidin-1-yl]pyridazin-3-one | 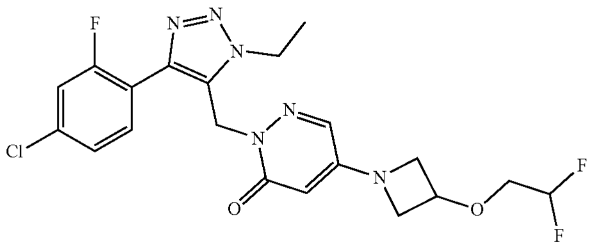 [SMILES: CCn1nnc(-c2ccc(Cl)cc2F)c1Cn1ncc(N2CC(OCC(F)F)C2)cc1=O] | 469.1 | 8 | K |
| 87 | 2-[[5-(4-chloro-2-fluoro-phenyl)-3-ethyl-triazol-4-yl]methyl]-5-[3-(2,2,2-trifluoro-ethoxy)azetidin-1-yl]pyridazin-3-one | 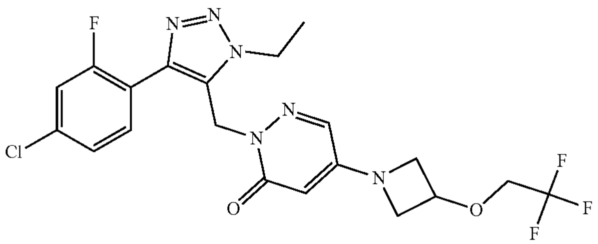 [SMILES: CCn1nnc(-c2ccc(Cl)cc2F)c1Cn1ncc(N2CC(OCC(F)(F)F)C2)cc1=O] | 487.1 | 8 | K |
| 88 | 2-[[5-(4-chloro-2-fluoro-phenyl)-3-ethyl-triazol-4-yl]methyl]-5-[3-(difluoromethoxy)azetidin-1-yl]pyridazin-3-one | 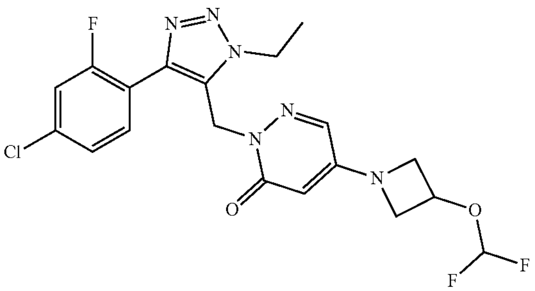 [SMILES: CCn1nnc(-c2ccc(Cl)cc2F)c1Cn1ncc(N2CC(OC(F)F)C2)cc1=O] | 455.1 | 8 | K |

-continued

| Ex | Name | Structure | MS(ESI) ([M + H]$^+$) | Method | Building block |
|---|---|---|---|---|---|
| 89 | 2-[[5-[2-fluoro-4-(trifluoromethyl)phenyl]-3-methyl-triazol-4-yl]methyl]-5-(3-pyrazin-2-yloxyazetidin-1-yl)pyridazin-3-one | 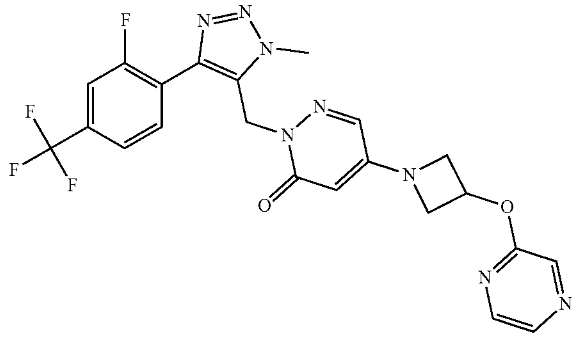 [SMILES: Cn1nnc(-c2ccc(C(F)(F)F)cc2F)c1Cn1ncc(N2CC(Oc3cnccn3)C2)cc1=O] | 503.2 | 8 | J |
| 90 | 2-[[5-(4-chloro-2-fluoro-phenyl)-3-ethyl-triazol-4-yl]methyl]-5-(3-isopropoxyazetidin-1-yl)pyridazin-3-one | 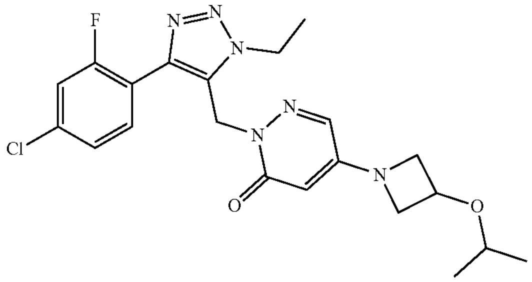 [SMILES: CCn1nnc(-c2ccc(Cl)cc2F)c1Cn1ncc(N2CC(OC(C)C)C2)cc1=O] | 447.1 | 8 | K |
| 91 | 2-[[5-(4-chloro-2-fluoro-phenyl)-3-ethyl-triazol-4-yl]methyl]-5-(3-ethoxyazetidin-1-yl)pyridazin-3-one | 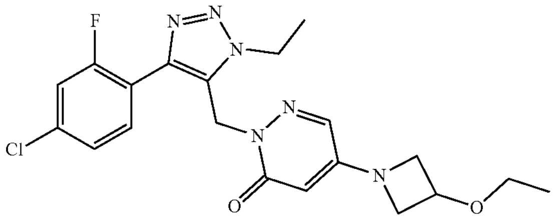 [SMILES: CCOC1CN(c2cnn(Cc3c(-c4ccc(Cl)cc4F)nnn3CC)c(=O)c2)C1] | 433.1 | 8 | K |
| 92 | 2-[[5-(4-chloro-2-fluoro-phenyl)-3-ethyl-triazol-4-yl]methyl]-5-[(3S)-4-isopropyl-3-methyl-piperazin-1-yl]pyridazin-3-one | 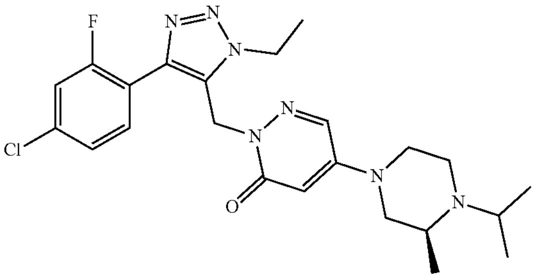 [SMILES: CCn1nnc(-c2ccc(Cl)cc2F)c1Cn1ncc(N2CCN(C(C)C)[C@@H](C)C2)cc1=O] | 474.1 | 8 | K |
| 93 | 5-[3-[(6-chloro-3-pyridyl)oxy]azetidin-1-yl]-2-[[5-[2-fluoro-4-(trifluoromethyl)phenyl]-3-methyl-triazol-4-yl]methyl]pyridazin-3-one | 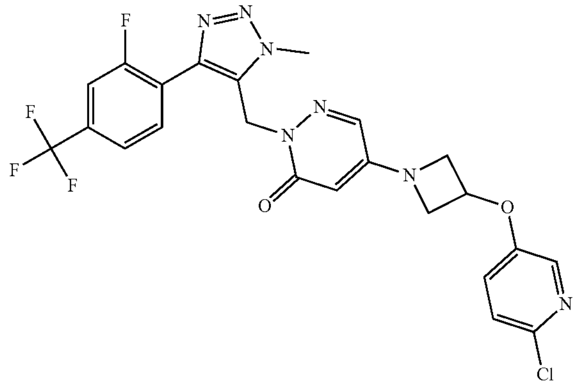 [SMILES: Cn1nnc(-c2ccc(C(F)(F)F)cc2F)c1Cn1ncc(N2CC(Oc3ccc(Cl)nc3)C2)cc1=O] | 536.2 | 8 | J |

-continued

| Ex | Name | Structure | MS(ESI) ([M + H]+) | Method | Building block |
|---|---|---|---|---|---|
| 94 | 2-[[5-[2-fluoro-4-(trifluoromethyl)phenyl]-3-methyl-triazol-4-yl]methyl]-5-[(3S)-4-isopropyl-3-methyl-piperazin-1-yl]pyridazin-3-one | 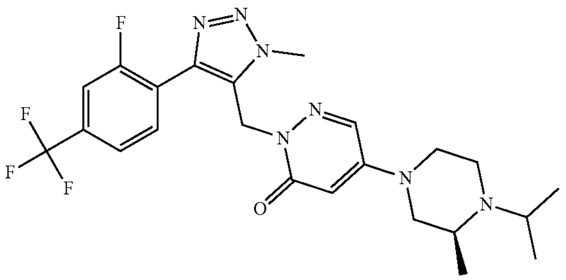 [SMILES: CC(C)N1CCN(c2cnn(Cc3c(-c4ccc(C(F)(F)F)cc4F)nnn3C)c(=O)c2)C[C@@H]1C] | 494.3 | 8 | J |
| 95 | 2-[[5-(4-chloro-2-fluoro-phenyl)-3-methyl-triazol-4-yl]methyl]-5-(5-oxa-2-azaspiro[3.5]nonan-2-yl)pyridazin-3-one | 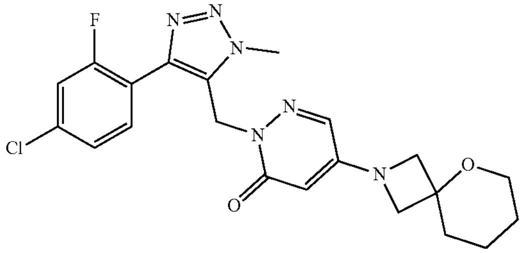 [SMILES: Cn1nnc(-c2ccc(Cl)cc2F)c1Cn1ncc(N2CC3(CCCCO3)C2)cc1=O] | 445.2 | 7 | E |
| 96 | 5-(3-tert-butoxyazetidin-1-yl)-2-[[5-(4-chloro-2-fluoro-phenyl)-3-methyl-triazol-4-yl]methyl]pyridazin-3-one | 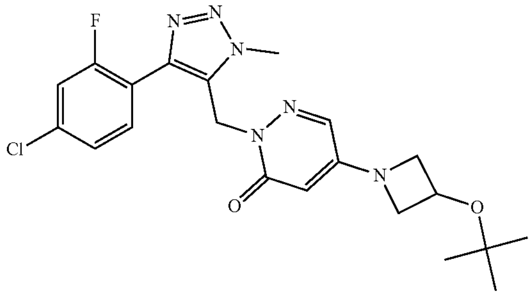 [SMILES: Cn1nnc(-c2ccc(Cl)cc2F)c1Cn1ncc(N2CC(OC(C)(C)C)C2)cc1=O] | 447.2 | 7 | E |
| 97 | 5-(3-tert-butoxyazetidin-1-yl)-2-[[5-(4-chloro-2-fluoro-phenyl)-3-ethyl-triazol-4-yl]methyl]pyridazin-3-one | 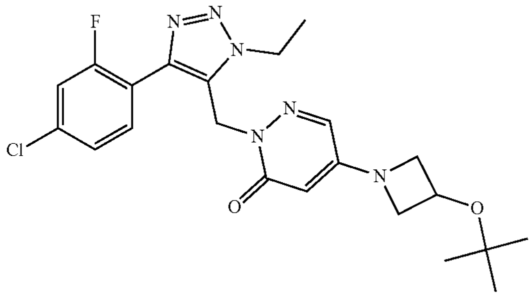 [SMILES: CCn1nnc(-c2ccc(Cl)cc2F)c1Cn1ncc(N2CC(OC(C)(C)C)C2)cc1=O] | 461.2 | 7 | K |
| 98 | 2-[[5-(4-chloro-2-fluoro-phenyl)-3-methyl-triazol-4-yl]methyl]-5-[3-[6-(trifluoromethyl)pyrazin-2-yl]oxyazetidin-1-yl]pyridazin-3-one | 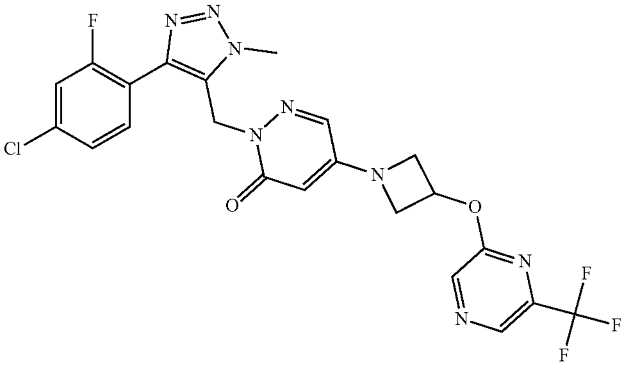 [SMILES: Cn1nnc(-c2ccc(Cl)cc2F)c1Cn1ncc(N2CC(Oc3cncc(C(F)(F)F)n3)C2)cc1=O] | 537.2 | 8 | E |

-continued

| Ex | Name | Structure | MS(ESI) ([M + H]+) | Method | Building block |
|---|---|---|---|---|---|
| 99 | 2-[[5-(4-chloro-2-fluoro-phenyl)-3-methyl-triazol-4-yl]methyl]-5-[3-(2-methylpyrimidin-4-yl)oxyazetidin-1-yl]pyridazin-3-one | 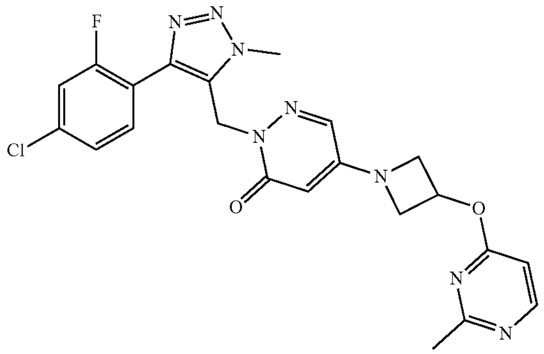 [SMILES: Cc1nccc(OC2CN(c3cnn(Cc4c(-c5ccc(Cl)cc5F)nnn4C)c(=O)c3)C2)n1] | 483.2 | 8 | E |
| 100 | 2-[[5-(4-chloro-2-fluoro-phenyl)-3-methyl-triazol-4-yl]methyl]-5-[3-[2-(trifluoromethyl) pyrimidin-4-yl]oxyazetidin-1-yl]pyridazin-3-one | 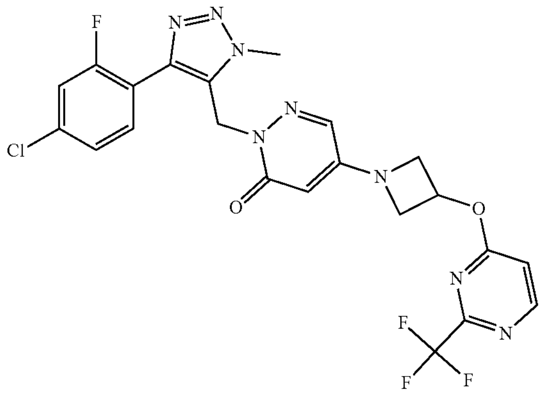 [SMILES: Cn1nnc(-c2ccc(Cl)cc2F)c1Cn1ncc(N2CC(Oc3ccnc(C(F)(F)F)n3)C2)cc1=O] | 537.2 | 8 | E |
| 101 | 2-[[5-(4-chloro-2-fluoro-phenyl)-3-ethyl-triazol-4-yl]methyl]-5-[3-[(6-chloro-3-pyridyl)oxy]azetidin-1-yl]pyridazin-3-one | 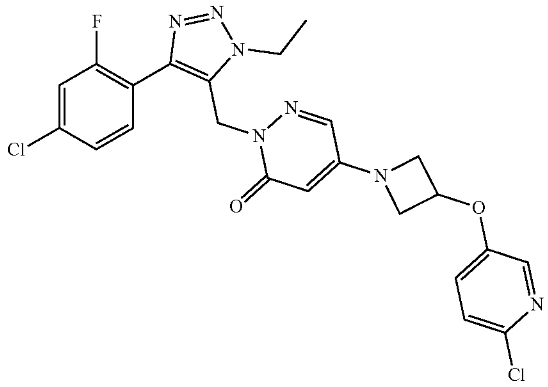 [SMILES: CCn1nnc(-c2ccc(Cl)cc2F)c1Cn1ncc(N2CC(Oc3ccc(Cl)nc3)C2)cc1=O] | 516.2 | 8 | K |
| 102 | 2-[[5-(4-chloro-2-fluoro-phenyl)-3-ethyl-triazol-4-yl]methyl]-5-(3-pyridazin-3-yloxyazetidin-1-yl)pyridazin-3-one | 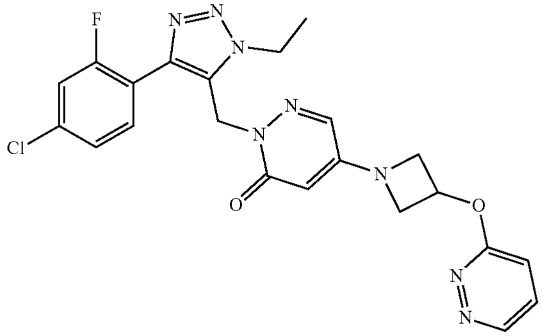 [SMILES: CCn1nnc(-c2ccc(Cl)cc2F)c1Cn1ncc(N2CC(Oc3cccnn3)C2)cc1=O] | 483.2 | 8 | K |

-continued

| Ex | Name | Structure | MS(ESI) ([M + H]+) | Method | Building block |
|---|---|---|---|---|---|
| 103 | 2-((5-(4-chloro-2-fluoro-phenyl)-3-methyl-triazol-4-yl)methyl)-5-(6-ethoxy-3-pyridyl)pyridazin-3-one | 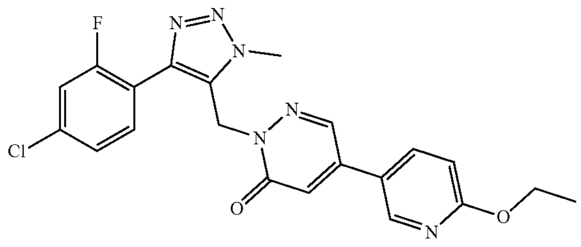 [SMILES: CCOc1ccc(-c2cnn(Cc3c(-c4ccc(Cl)cc4F)nnn3C)c(=O)c2)cn1] | 441.2 | 10 | E |
| 104 | 2-((5-(4-chloro-2-fluoro-phenyl)-3-methyl-triazol-4-yl)methyl)-5-(6-methoxy-5-methyl-3-pyridyl)pyridazin-3-one | 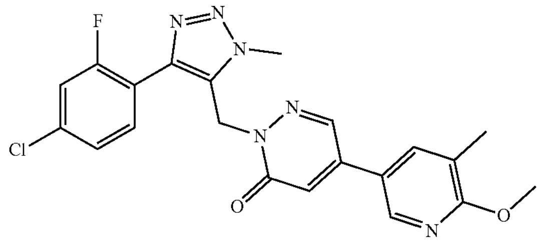 [SMILES: COc1ncc(-c2cnn(Cc3c(-c4ccc(Cl)cc4F)nnn3C)c(=O)c2)cc1C] | 441.2 | 10 | E |
| 105 | 2-((4-(4-chloro-2-fluorophenyl)-1-ethyl-1H-1,2,3-triazol-5-yl)methyl)-5-(1-cyclopropyl-1H-pyrazol-4-yl)pyridazin-3(2H)-one | 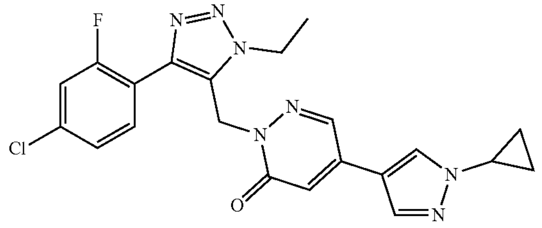 [SMILES: CCn1nnc(-c2ccc(Cl)cc2F)c1Cn1ncc(-c2cnn(C3CC3)c2)cc1=O] | 440.2 | 10 | K |
| 106 | 2-((5-(4-chloro-2-fluoro-phenyl)-3-methyl-triazol-4-yl)methyl)-5-(1-(2,2-difluoro-ethyl)pyrazol-4-yl)pyridazin-3-one | 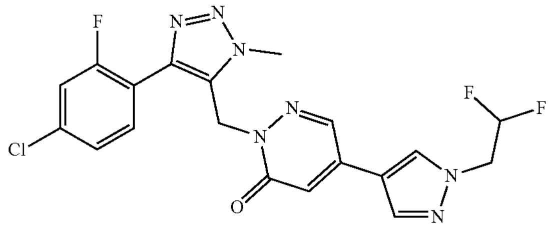 [SMILES: Cn1nnc(-c2ccc(Cl)cc2F)c1Cn1ncc(-c2cnn(CC(F)F)c2)cc1=O] | 450.2 | 10 | E |
| 107 | 6-(1-((5-(4-chloro-2-fluoro-phenyl)-3-methyl-triazol-4-yl)methyl)-6-oxo-pyridazin-4-yl)pyridine-2-carbonitrile | 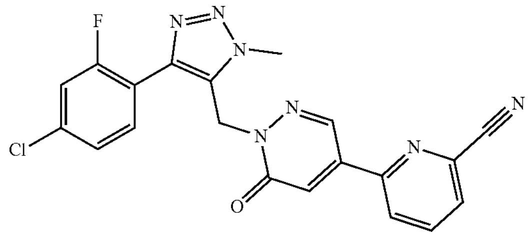 [SMILES: Cn1nnc(-c2ccc(Cl)cc2F)c1Cn1ncc(-c2cccc(C#N)n2)cc1=O] | 422.1 | 10 | E |
| 108 | 2-((5-(4-chloro-2-fluoro-phenyl)-3-methyl-triazol-4-yl)methyl)-5-(6-chloro-5-metlioxy-3-pyridyl)pyridazin-3-one | 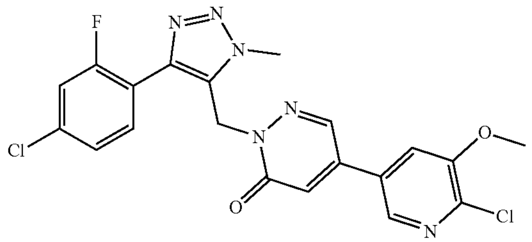 [SMILES: COc1cc(-c2cnn(Cc3c(-c4ccc(Cl)cc4F)nnn3C)c(=O)c2)cnc1Cl] | 461.1 | 10 | E |

-continued

| Ex | Name | Structure | MS(ESI) ([M + H]+) | Method | Building block |
|---|---|---|---|---|---|
| 109 | 2-[[5-(6-chloro-3-pyridyl)-3-methyl-triazol-4-yl]methyl]-5-[(2R)-2-methylpyrrolidin-1-yl]pyridazin-3-one | 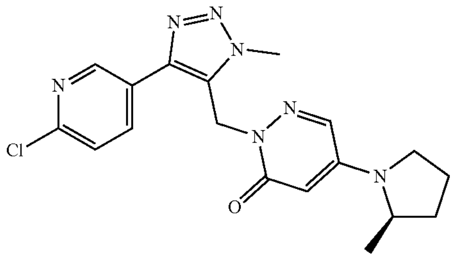 [SMILES: C[C@@H]1CCCN1c1cnn(Cc2c(-c3ccc(Cl)nc3)nnn2C)c(=O)c1] | 386.2 | 4 | L |
| 110 | 2-((4-(4-chloro-2-fluorophenyl)-1-ethyl-1H-1,2,3-triazol-5-yl)methyl)-5-(5-chloro-6-methoxypyridin-3-yl)pyridazin-3(2H)-one | 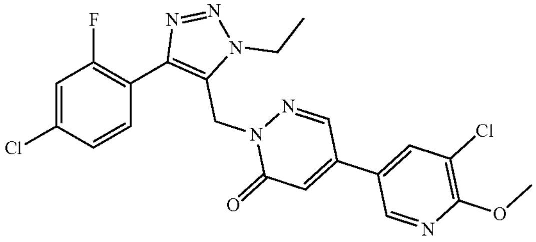 [SMILES: CCn1nnc(-c2ccc(Cl)cc2F)c1Cn1ncc(-c2cnc(OC)c(Cl)c2)cc1=O] | 475.3 | 10 | K |
| 111 | 6-(1-((4-(4-chloro-2-fluorophenyl)-1-ethyl-1H-1,2,3-triazol-5-yl)methyl)-6-oxo-1,6-dihydropyridazin-4-yl)picolinonitrile | 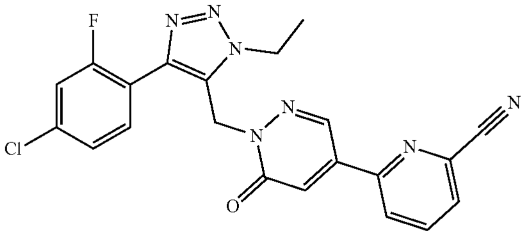 [SMILES: CCn1nnc(-c2ccc(Cl)cc2F)c1Cn1ncc(-c2cccc(C#N)n2)cc1=O] | 436.3 | 10 | K |
| 112 | 2-[[5-(6-chloro-3-pyridyl)-3-methyl-triazol-4-yl]methyl]-5-[(2S,6R)-2,6-dimethylmorpholin-4-yl]pyridazin-3-one | 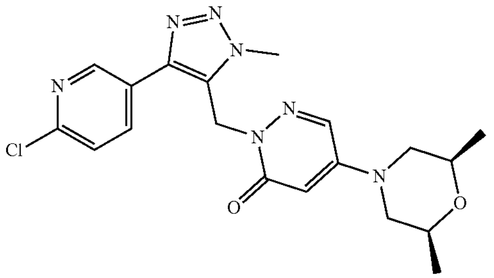 [SMILES: C[C@@H]1CN(c2cnn(Cc3c(-c4ccc(Cl)nc4)nnn3C)c(=O)c2)C[C@H](C)O1] | 416.3 | 4 | L |
| 113 | 2-[[5-(4-chloro-2-fluoro-phenyl)-3-methyl-triazol-4-yl]methyl]-5-[3-(5-methylpyrazol-1-yl)azetidin-1-yl]pyridazin-3-one | 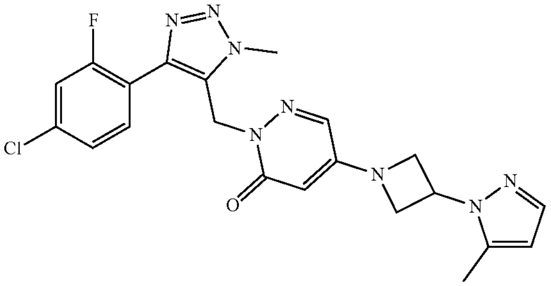 [SMILES: Cc1ccnn1C1CN(c2cnn(Cc3c(-c4ccc(Cl)cc4F)nnn3C)c(=O)c2)C1] | 455.3 | 7 | E |
| 114 | 5-(5-chloro-6-methoxy-3-pyridyl)-2-[[3-methyl-5-(6-methylpyridazin-3-yl)triazol-4-yl]methyl]pyridazin-3-one | 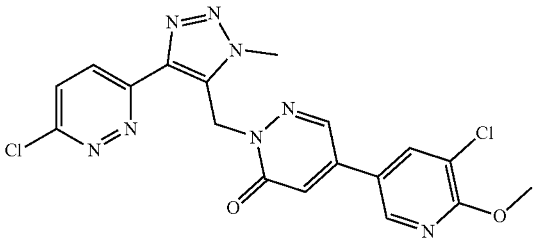 [SMILES: COc1ncc(-c2cnn(Cc3c(-c4ccc(Cl)nn4)nnn3C)c(=O)c2)cc1Cl] | 425.1 | 1 | O |

-continued

| Ex | Name | Structure | MS(ESI) ([M + H]+) | Method | Building block |
|---|---|---|---|---|---|
| 115 | 5-(3-ethoxyazetidin-1-yl)-2-[[3-methyl-5-[5-(trifluoromethyl)pyrimidin-2-yl]triazol-4-yl]methyl]pyridazin-3-one | 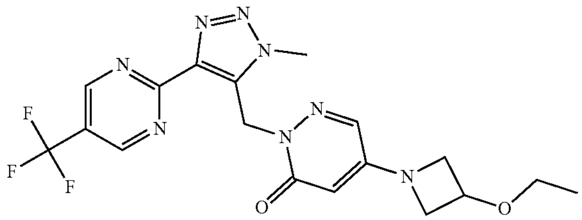 [SMILES: CCOC1CN(c2cnn(Cc3c(-c4ncc(C(F)(F)F)cn4)nnn3C)c(=O)c2)C1] | 437.1 | 8 | M |
| 116 | 5-(3-isopropoxyazetidin-1-yl)-2-[[3-methyl-5-[5-(trifluoromethyl)pyrimidin-2-yl]triazol-4-yl]methyl]pyridazin-3-one | 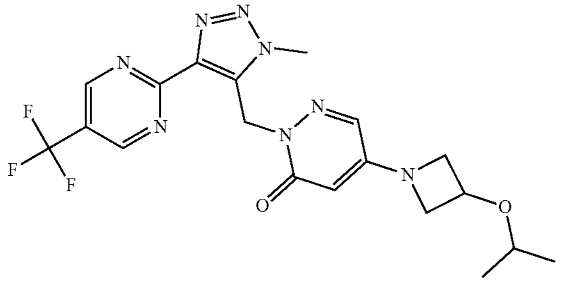 [SMILES: CC(C)OC1CN(c2cnn(Cc3c(-c4ncc(C(F)(F)F)cn4)nnn3C)c(=O)c2)C1] | 451.1 | 8 | M |
| 117 | 5-[3-(cyclo-butoxy)azetidin-1-yl]-2-[[3-methyl-5-[5-(trifluoromethyl)pyrimidin-2-yl]triazol-4-yl]methyl]pyridazin-3-one | 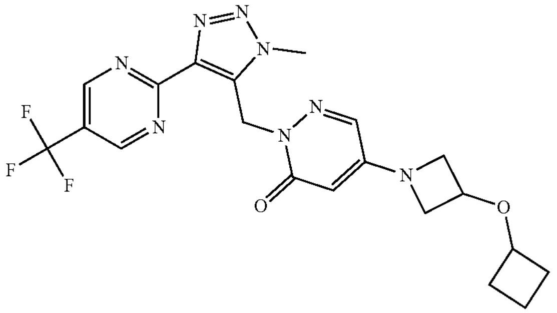 [SMILES: Cn1nnc(-c2ncc(C(F)(F)F)cn2)c1Cn1ncc(N2CC(OC3CCC3)C2)cc1=O] | 463.1 | 8 | M |
| 118 | 5-(5-chloro-6-methoxypyridin-3-yl)-2-((1-methyl-4-(5-(trifluoromethyl)pyrimidin-2-yl)-1H-1,2,3-triazol-5-yl)methyl)pyridazin-3(2H)-one | 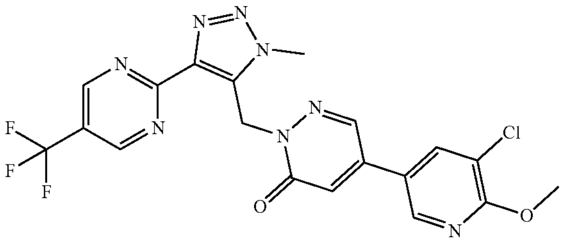 [SMILES: COc1ncc(-c2cnn(Cc3c(-c4ncc(C(F)(F)F)cn4)nnn3C)c(=O)c2)cc1Cl] | 479.1 | 10 | M |
| 119 | 5-[3-(2,2-difluoro-ethoxy)azetidin-1-yl]-2-[[3-methyl-5-[5-(trifluoromethyl)pyrimidin-2-yl]triazol-4-yl]methyl]pyridazin-3-one | 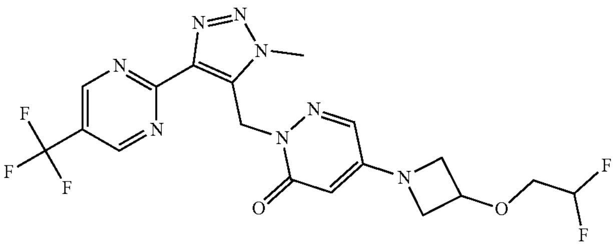 [SMILES: Cn1nnc(-c2ncc(C(F)(F)F)cn2)c1Cn1ncc(N2CC(OCC(F)F)C2)cc1=O] | 473.1 | 8 | M |

-continued

| Ex | Name | Structure | MS(ESI) ([M + H]+) | Method | Building block |
|---|---|---|---|---|---|
| 120 | 2-[[3-methyl-5-[5-(trifluoromethyl) pyrimidin-2-yl]triazol-4-yl]methyl]-5-[3-(2,2,2-trifluoro-ethoxy)azetidin-1-yl]pyridazin-3-one | 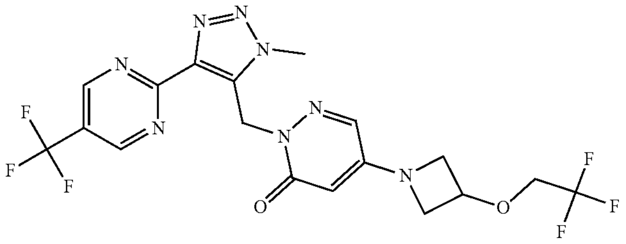 [SMILES: Cn1nnc(-c2ncc(C(F)(F)F)cn2)c1Cn1ncc(N2CC(OCC(F)(F)F)C2)cc1=O] | 491.1 | 8 | M |
| 121 | 5-[3-(difluoromethoxy) azetidin-1-yl]-2-[[3-methyl-5-[5-(trifluoromethyl) pyrimidin-2-yl]triazol-4-yl]methyl]pyridazin-3-one | 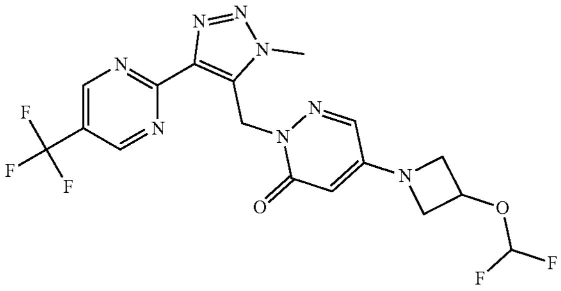 [SMILES: Cn1nnc(-c2ncc(C(F)(F)F)cn2)c1Cn1ncc(N2CC(OC(F)F)C2)cc1=O] | 459.1 | 8 | M |
| 122 | (R)-2-((4-(4-chloro-2-fluorophenyl)-1-ethyl-1H-1,2,3-triazol-5-yl)methyl)-5-(7-methyl-5-oxa-2-azaspiro[3.5]nonan-2-yl)pyridazin-3(2H)-one | 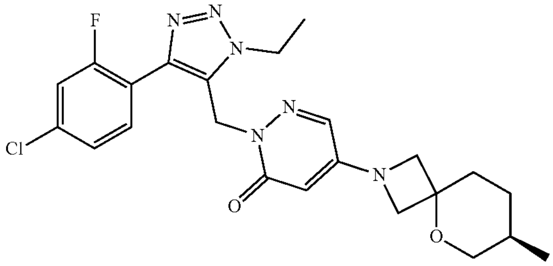 [SMILES: CCn1nnc(-c2ccc(Cl)cc2F)c1Cn1ncc(N2CC3(CC[C@@H](C)CO3)C2)cc1=O] | 473.7 | 8 | K |
| 123 | 5-(5-chloro-6-methoxypyridin-3-yl)-2-((1-methyl-4-(6-(trifluoro-methyl)pyridazin-3-yl)-1H-1,2,3-triazol-5-yl)methyl)pyridazin-3(2H)-one | 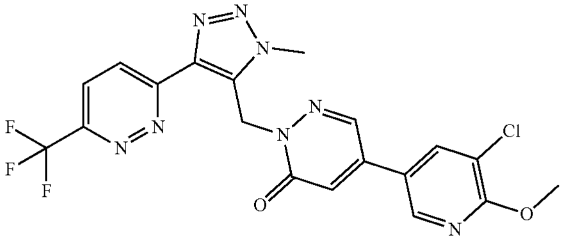 [SMILES: COc1ncc(-c2cnn(Cc3c(-c4ccc(C(F)(F)F)nn4)nnn3C)c(=O)c2)cc1Cl] | 479.0 | 1 | N |
| 124 | (S)-2-((4-(4-chloro-2-fluorophenyl)-1-ethyl-1H-1,2,3-triazol-5-yl)methyl)-5-(7-fluoro-5-oxa-2-azaspiro[3.5]nonan-2-yl)pyridazin-3(2H)-one | 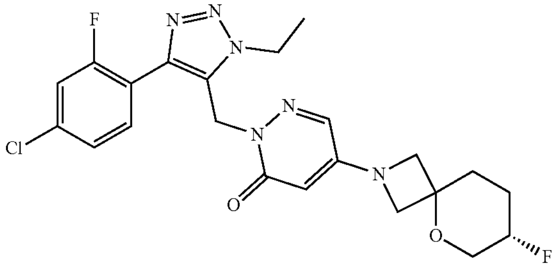 [SMILES: CCn1nnc(-c2ccc(Cl)cc2F)c1Cn1ncc(N2CC3(CC[C@H](F)CO3)C2)cc1=O] | 477.7 | 8 | K |

-continued
| Ex | Name | Structure | MS(ESI) ([M + H]+) | Method | Building block |
|---|---|---|---|---|---|
| 125 | (R)-2-((4-(4-chloro-2-fluorophenyl)-1-ethyl-1H-1,2,3-triazol-5-yl)methyl)-5-(7-fluoro-5-oxa-2-azaspiro[3.5]nonan-2-yl)pyridazin-3(2H)-one | 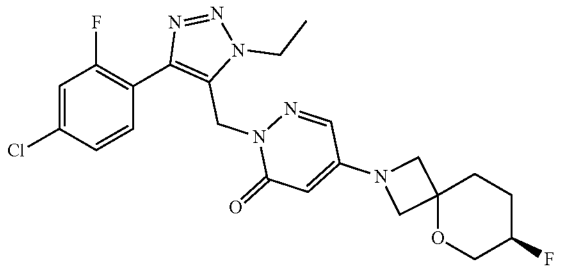 [SMILES: CCn1nnc(-c2ccc(Cl)cc2F)c1Cn1ncc(N2CC3(CC[C@@H](F)CO3)C2)cc1=O] | 477.7 | 8 | K |
| 126 | (S)-2-((4-(4-chloro-2-fluorophenyl)-1-methyl-1H-1,2,3-triazol-5-yl)methyl)-5-(7-fluoro-5-oxa-2-azaspiro[3.5]nonan-2-yl)pyridazin-3(2H)-one | 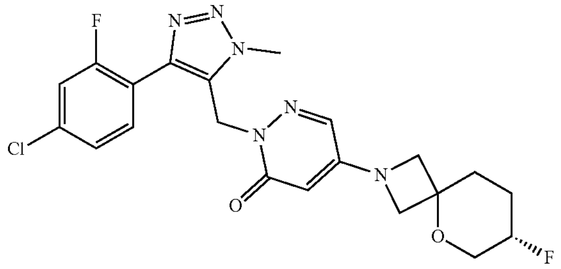 [SMILES: Cn1nnc(-c2ccc(Cl)cc2F)c1Cn1ncc(N2CC3(CC[C@H](F)CO3)C2)cc1=O] | 463.6 | 8 | E |
The invention claimed is:
1. A compound selected from the group consisting of:
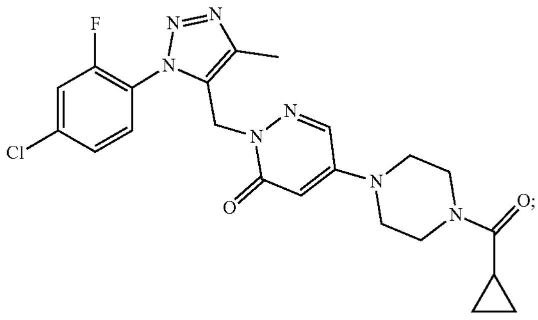
;
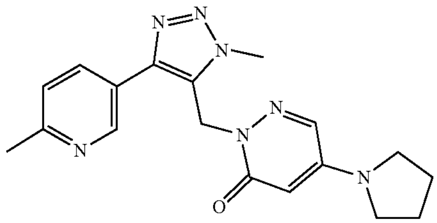
;
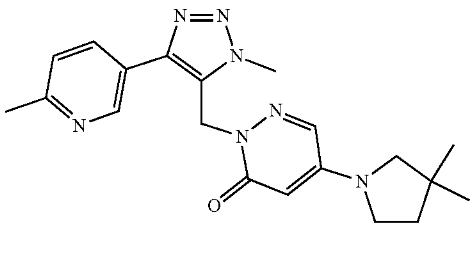
;
-continued
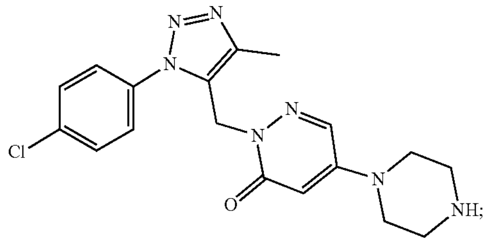
;
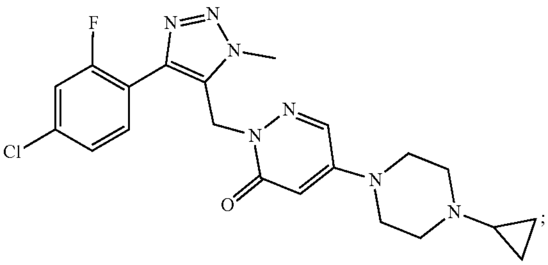
;
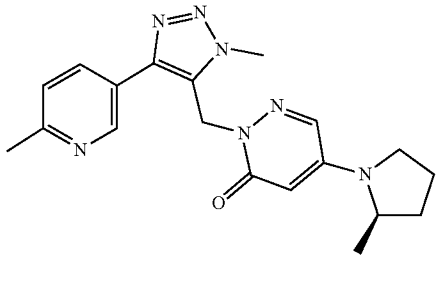
;

-continued
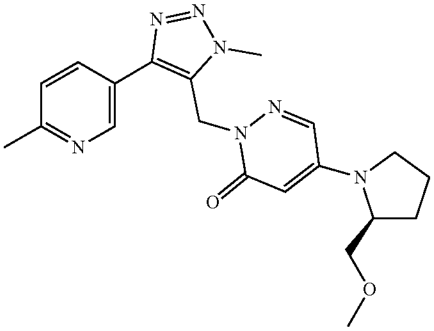
;
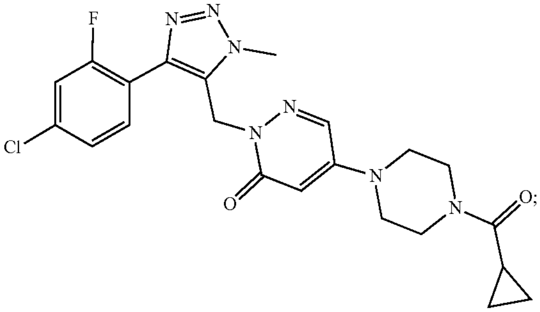
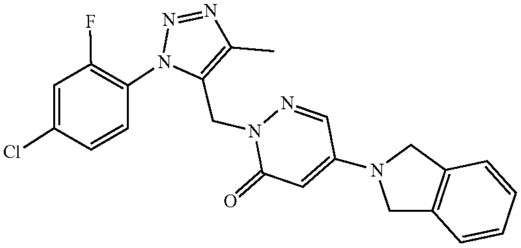
;
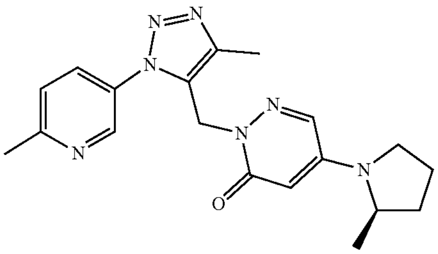
;
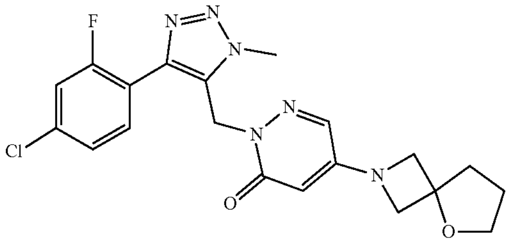
;
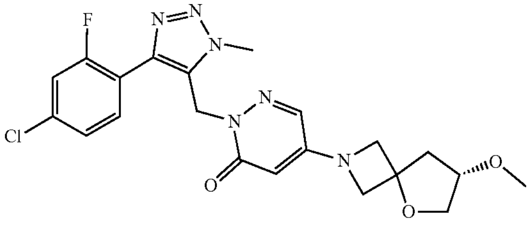
;
-continued
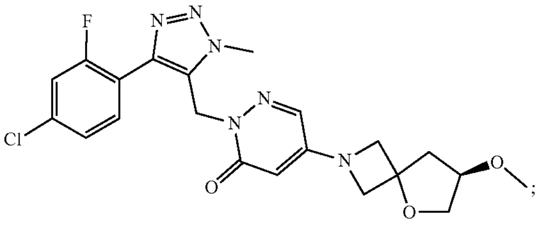
;
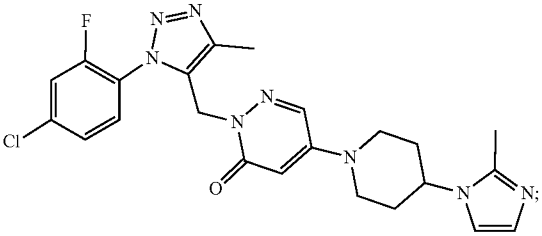
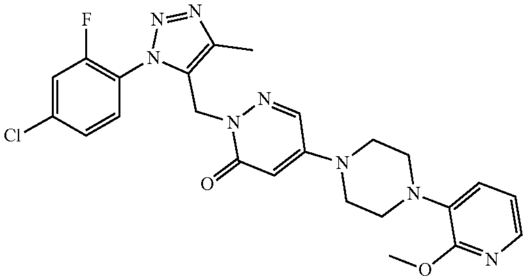
;
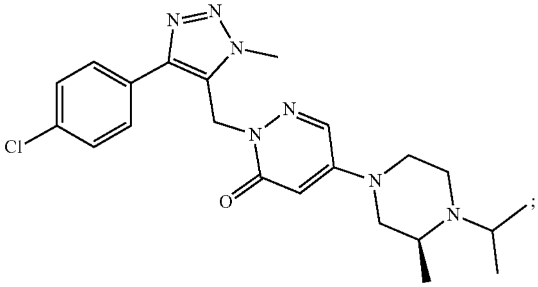
;
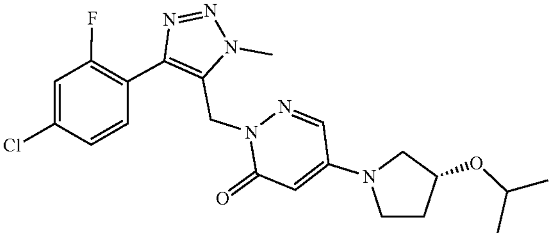
;
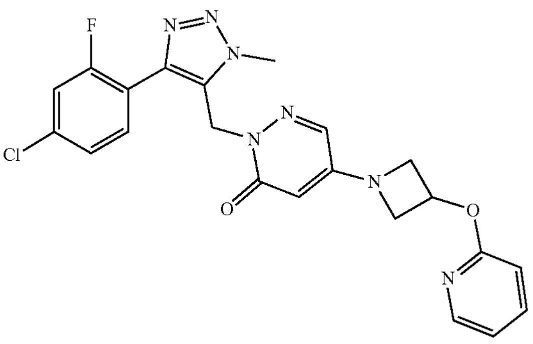
;

-continued
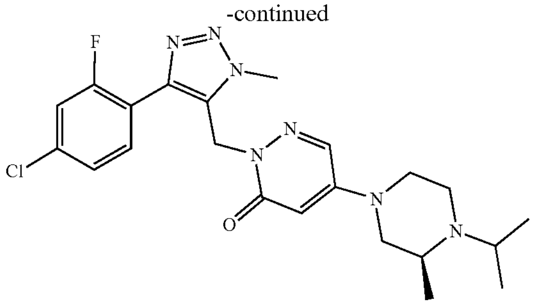
;
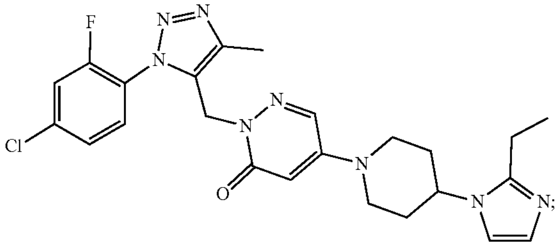
;
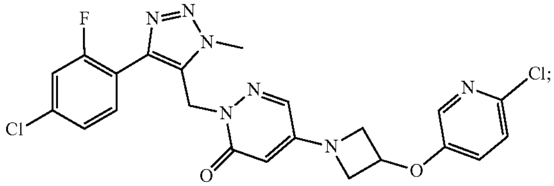
;
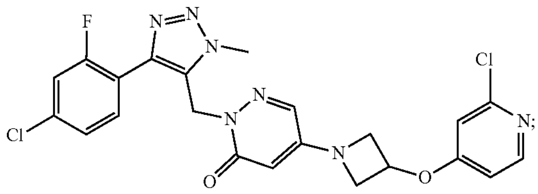
;
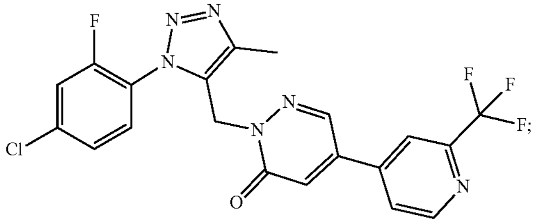
;
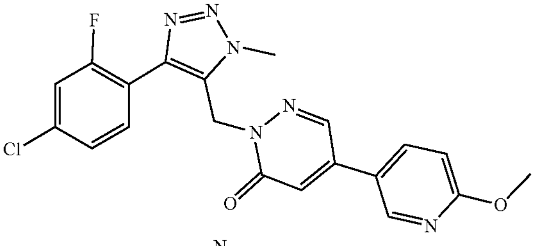
;
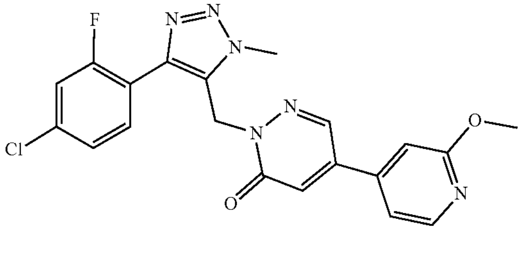
;
-continued
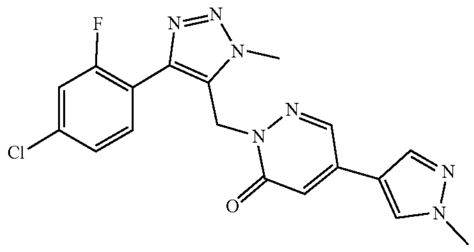
;
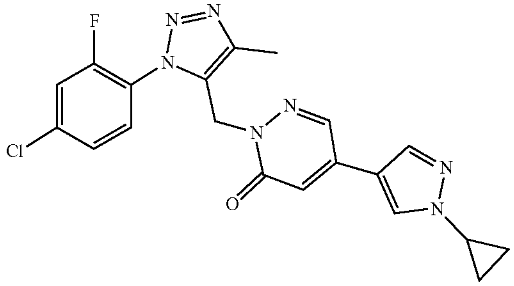
;
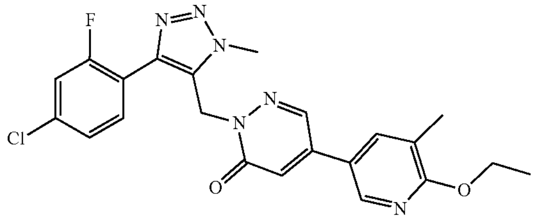
;
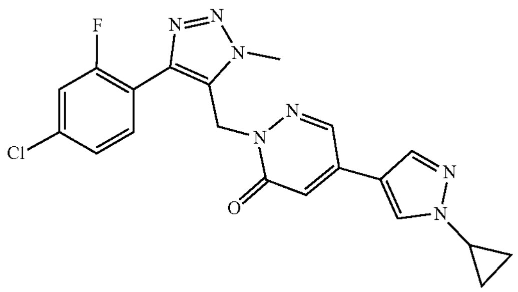
;
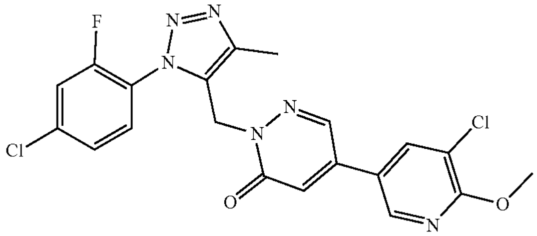
;
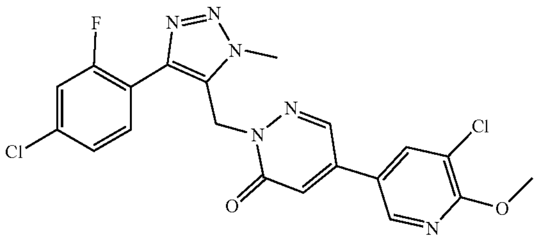
;
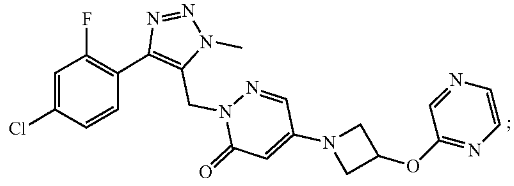
;

-continued
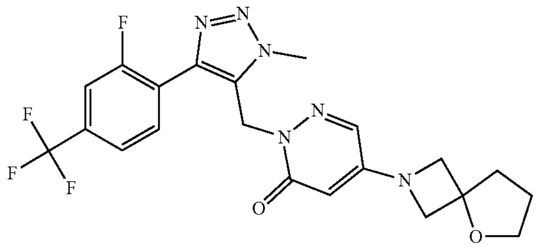
;
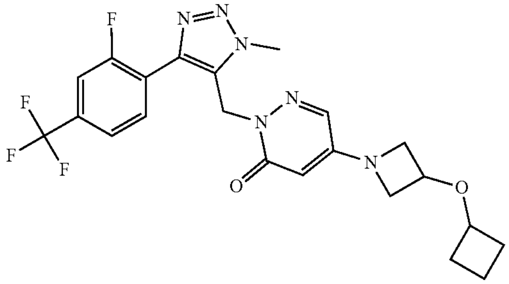
;
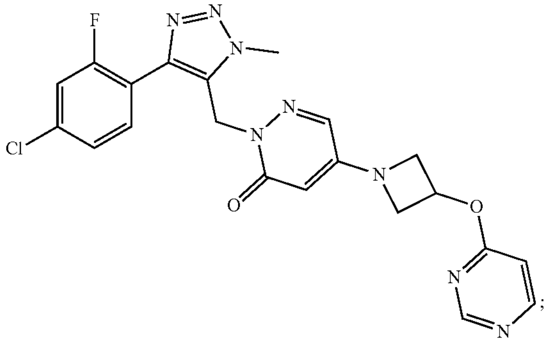
;
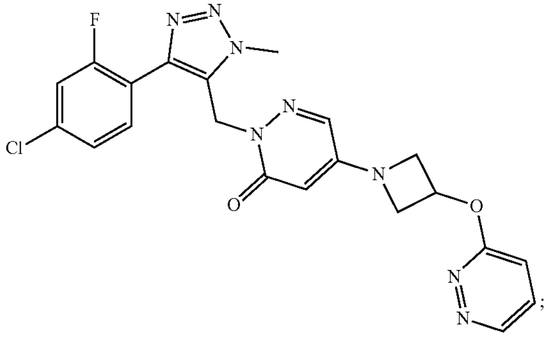
;
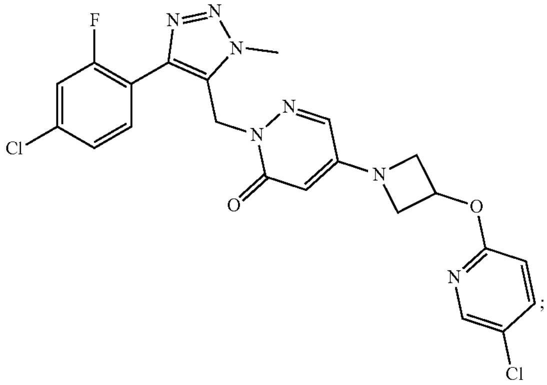
;
-continued
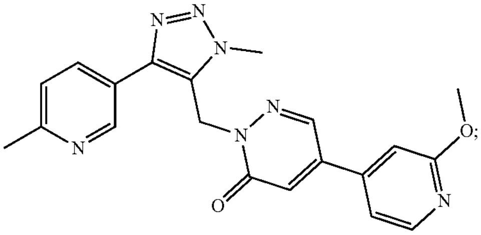
;
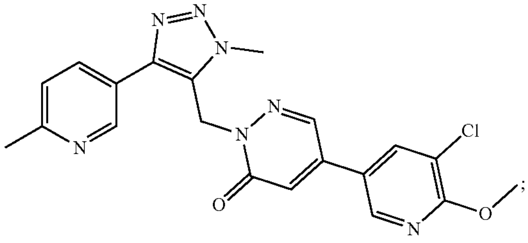
;
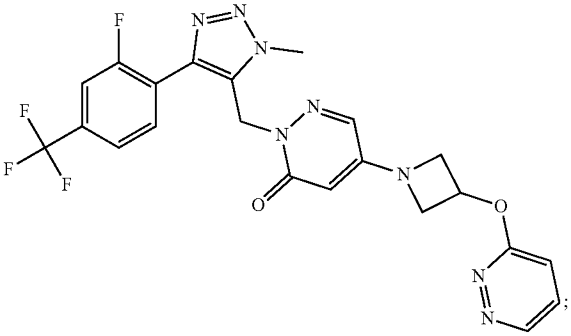
;
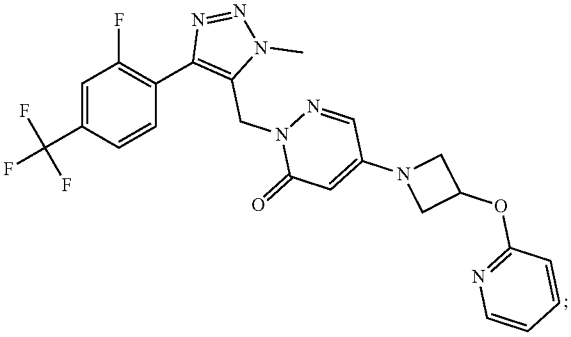
;
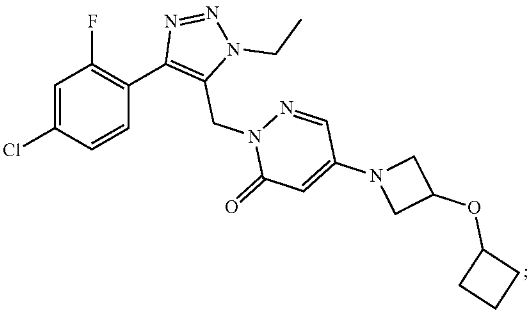
;

-continued
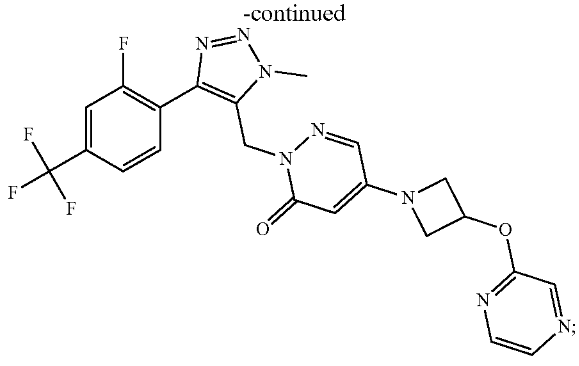
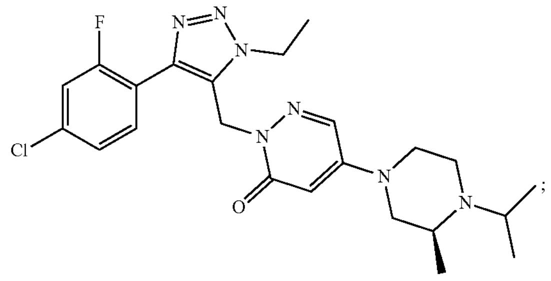
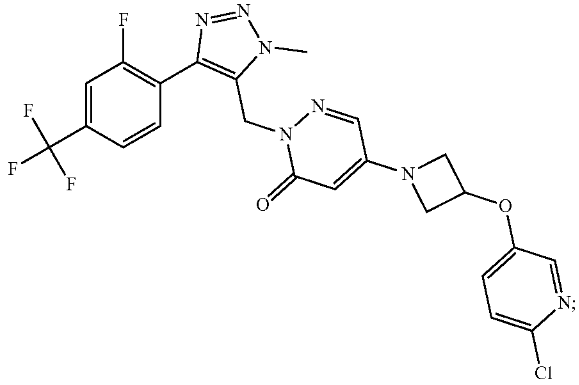
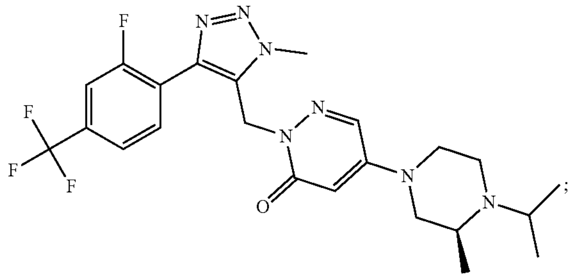
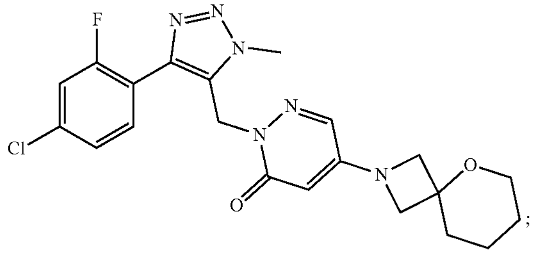
-continued
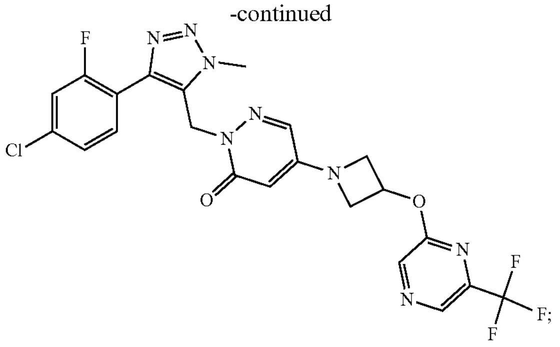
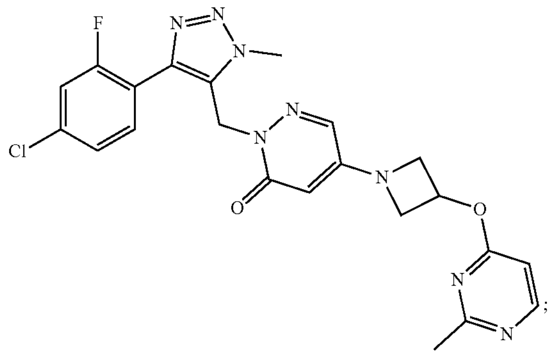
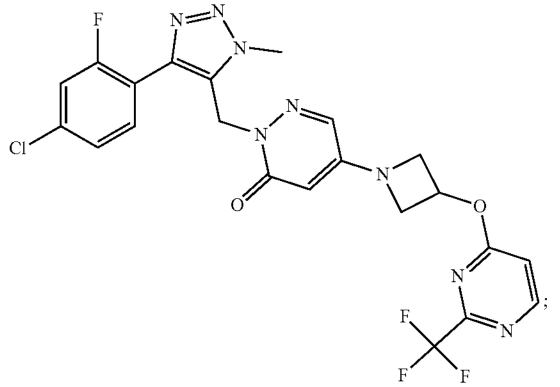
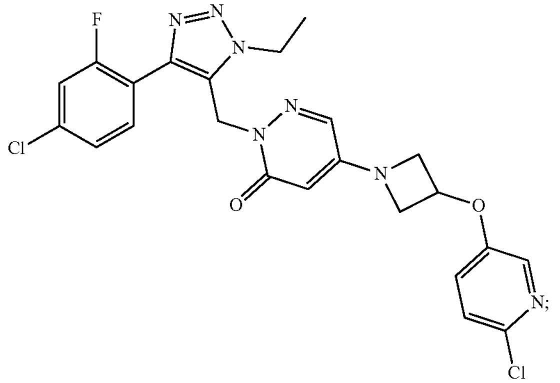

-continued
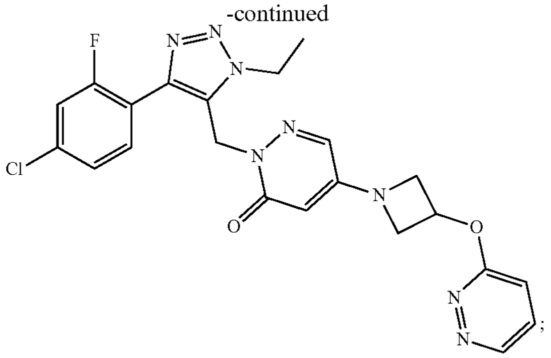
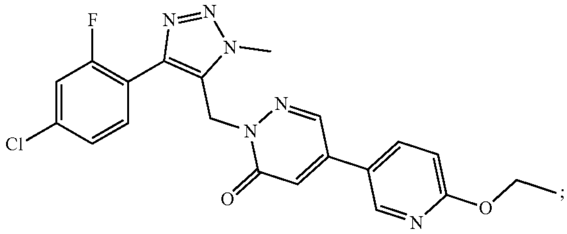
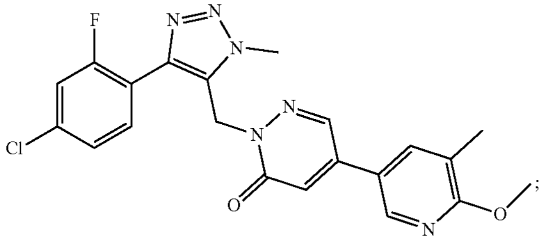
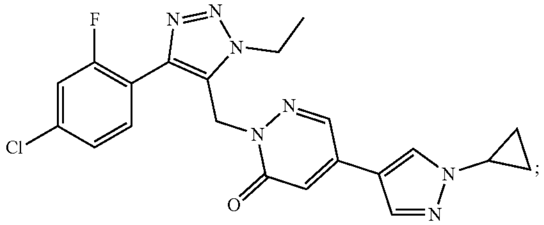
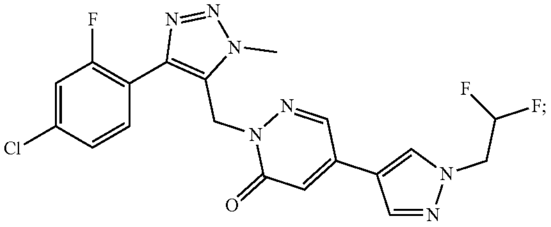
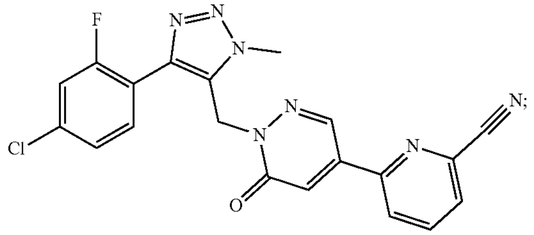
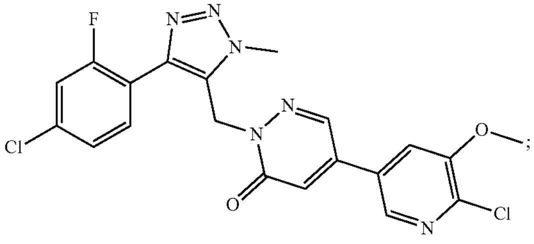
-continued
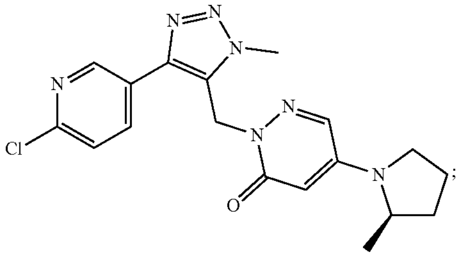
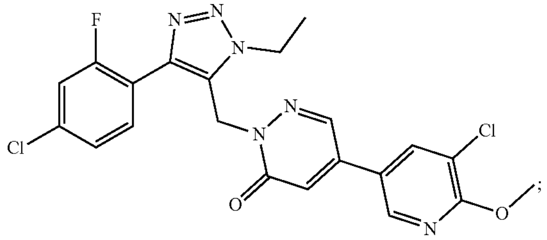
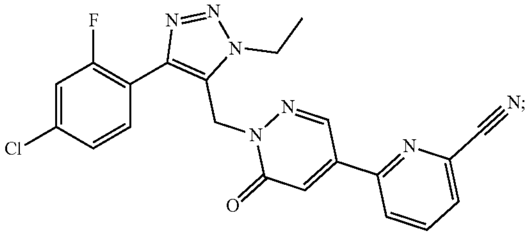
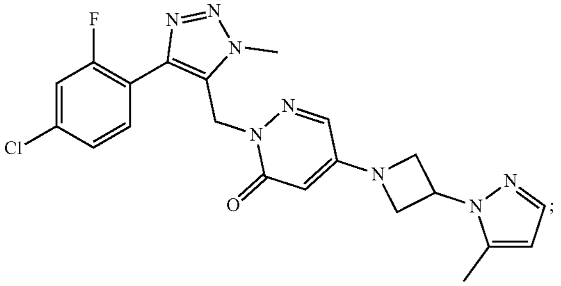
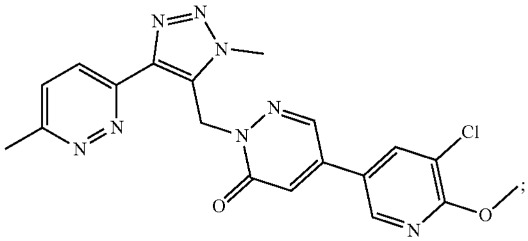
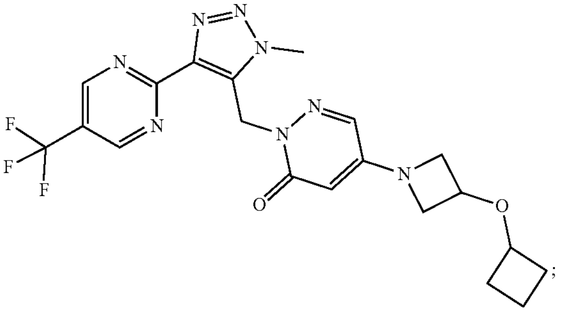

-continued

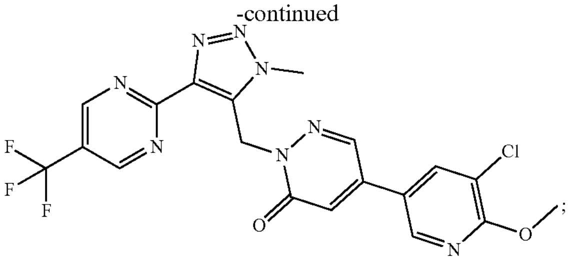

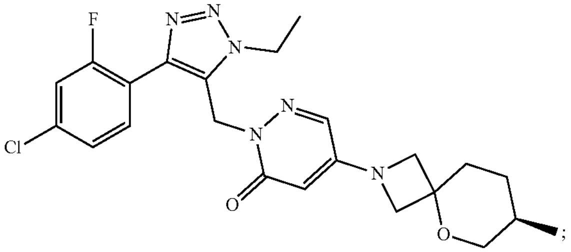

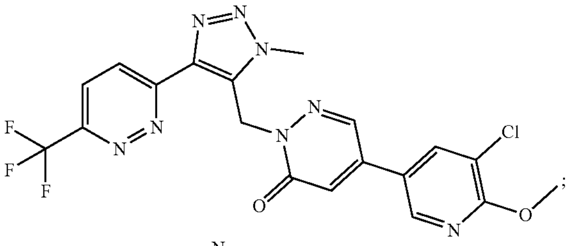

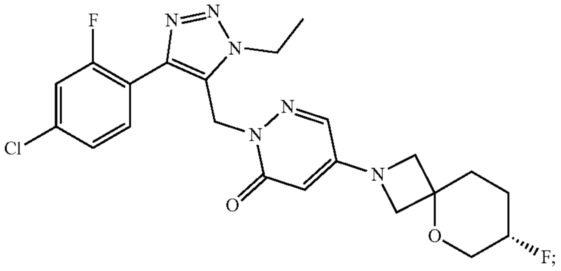

-continued

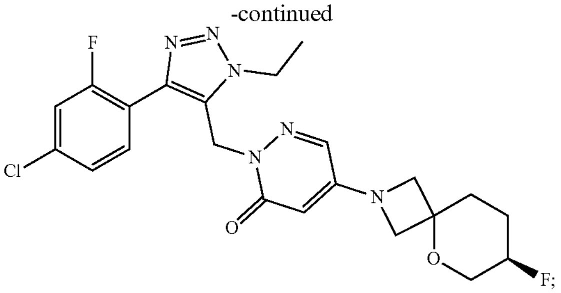

and

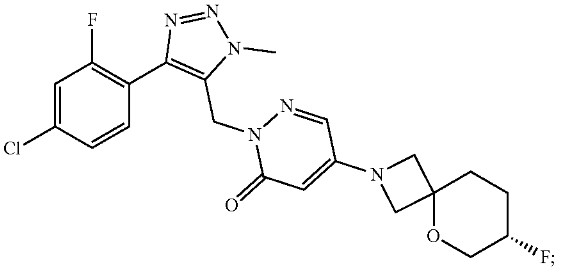

or a stereoisomer or a pharmaceutical salt thereof.

2. A pharmaceutical composition comprising a compound according to claim 1 or pharmaceutically acceptable salts thereof, and a therapeutically inert carrier.

3. A method the treatment or prophylaxis of Alzheimer's disease, mild cognitive impairment, age-related cognitive decline, negative and/or cognitive symptoms associated with schizophrenia, bipolar disorders, autism spectrum disorder, Angelman syndrome, Rett syndrome, Prader-Willi syndrome, epilepsy, post-traumatic stress disorder, amyotrophic lateral sclerosis, fragile-X disorder, the method comprising admininstering an effective amount of a compound according to claim 1 to a patient in need thereof.

* * * * *